US012622609B2

(12) United States Patent　　(10) Patent No.:　US 12,622,609 B2
Ritsher et al.　　(45) Date of Patent:　May 12, 2026

(54) WEARABLE SYSTEMS, DEVICES AND METHODS FOR MEASUREMENT AND ANALYSIS OF BODY FLUIDS

(71) Applicant: Nix, Inc., Boston, MA (US)

(72) Inventors: Kenneth Ritsher, Lowell, MA (US); Shawn Mishra, Lawrence, MA (US); Brett Cochran, Boston, MA (US); Daniel Tonderys, Cambridge, MA (US); Michael Roberts, Medford, MA (US); Meridith Unger Cass, Medford, MA (US)

(73) Assignee: Nix, Inc., Medford, MA (US)

( * ) Notice: Subject to any disclaimer, the term of this patent is extended or adjusted under 35 U.S.C. 154(b) by 1204 days.

(21) Appl. No.: 17/319,477

(22) Filed: May 13, 2021

(65) Prior Publication Data

US 2021/0259589 A1　　Aug. 26, 2021

Related U.S. Application Data

(63) Continuation of application No. PCT/US2019/061301, filed on Nov. 13, 2019.

(Continued)

(51) Int. Cl.
*A61B 5/145*　　　(2006.01)
*A61B 5/00*　　　(2006.01)
(Continued)

(52) U.S. Cl.
CPC ............ *A61B 5/14517* (2013.01); *A61B 5/01* (2013.01); *A61B 5/0531* (2013.01); *A61B 5/265* (2021.01); *A61B 5/4875* (2013.01);

*A61B 5/68335* (2017.08); *A61B 5/746* (2013.01); *A61B 2562/0219* (2013.01); *A61B 2562/0271* (2013.01)

(58) Field of Classification Search
None
See application file for complete search history.

(56) References Cited

U.S. PATENT DOCUMENTS 3,139,085 A　　6/1964　Custance et al.
4,190,056 A　　2/1980　Tapper et al.
(Continued)

FOREIGN PATENT DOCUMENTS

CA　　2780747 A1　　5/2010
CA　　2769402 A1　　2/2011
(Continued)

OTHER PUBLICATIONS

Dickson et al. "The effects of dehydration on brain volume-preliminary results." International Journal of Sports Medicine. Jul. 2005;26(06):481-5.

(Continued)

*Primary Examiner* — Lore R Jarrett
(74) *Attorney, Agent, or Firm* — COOLEY LLP

(57)　　　ABSTRACT

Systems, devices and methods are described herein for various embodiments of a sample analysis system that is worn by a user, the sample analysis system configured to collect a sample of bodily fluid, and measure and analyze the bodily fluid to determine a property of the bodily fluid and/or a health parameter (e.g., degree of hydration, electrolyte losses, perspiration rate, etc.) of the user.

19 Claims, 48 Drawing Sheets

Related U.S. Application Data

(60) Provisional application No. 62/760,202, filed on Nov. 13, 2018.

(51) Int. Cl.

| | |
|---|---|
| *A61B 5/01* | (2006.01) |
| *A61B 5/0531* | (2021.01) |
| *A61B 5/265* | (2021.01) |

(56) References Cited

U.S. PATENT DOCUMENTS

| | | | |
|---|---|---|---|
| 4,190,060 | A | 2/1980 | Greenleaf et al. |
| 4,195,641 | A | 4/1980 | Joines et al. |
| 4,203,450 | A | 5/1980 | Kegel |
| 4,266,556 | A | 5/1981 | Barlow et al. |
| 4,542,751 | A | 9/1985 | Webster et al. |
| 4,638,512 | A | 1/1987 | Frankel |
| 4,756,314 | A | 7/1988 | Eckenhoff et al. |
| 5,131,390 | A | 7/1992 | Sakaguchi et al. |
| 5,174,656 | A | 12/1992 | Dotan |
| 5,757,278 | A | 5/1998 | Itsumi |
| 5,976,499 | A | 11/1999 | Rubenstein et al. |
| 6,132,975 | A | 10/2000 | Kanan et al. |
| 6,198,953 | B1 | 3/2001 | Webster et al. |
| 6,269,265 | B1 | 7/2001 | Anderson |
| 6,276,155 | B2 | 8/2001 | Siman-Tov et al. |
| 6,309,535 | B1 | 10/2001 | Williams et al. |
| 6,332,225 | B1 | 12/2001 | Casey |
| D453,985 | S | 3/2002 | Casey |
| 6,443,892 | B1 | 9/2002 | Kidwell |
| 6,517,497 | B2 | 2/2003 | Rymut et al. |
| 6,585,986 | B2 | 7/2003 | Matsuzaki et al. |
| 6,726,818 | B2 | 4/2004 | Cui et al. |
| 6,780,307 | B2 | 8/2004 | Kidwell |
| 6,943,662 | B2 | 9/2005 | Tanimura |
| 7,783,344 | B2 | 8/2010 | Lackey et al. |
| 7,964,409 | B1 | 6/2011 | Kennedy |
| 8,215,192 | B2 | 7/2012 | Erez et al. |
| 8,273,021 | B2 | 9/2012 | Jang et al. |
| 8,372,726 | B2 | 2/2013 | de Graff et al. |
| 8,551,608 | B2 | 10/2013 | Kawakami et al. |
| 8,934,954 | B2 | 1/2015 | Brunswick et al. |
| 9,113,559 | B2 | 8/2015 | Heikenfeld et al. |
| 9,200,165 | B2 | 12/2015 | Imokawa et al. |
| 9,226,730 | B2 | 1/2016 | Briscoe et al. |
| 9,339,225 | B2 | 5/2016 | Kennedy |
| 9,456,650 | B1 | 10/2016 | Boyce |
| D781,270 | S | 3/2017 | Li et al. |
| 9,603,560 | B2 | 3/2017 | Monty et al. |
| 9,625,705 | B2 | 4/2017 | Dean et al. |
| 9,662,069 | B2 | 5/2017 | De Graff et al. |
| 9,677,919 | B2 | 6/2017 | Kielb et al. |
| 9,704,908 | B2 | 7/2017 | Graff et al. |
| 9,723,122 | B2 | 8/2017 | Ghaffari et al. |
| D797,379 | S | 9/2017 | Patel et al. |
| 9,757,050 | B2 | 9/2017 | Ghaffari et al. |
| 9,801,557 | B2 | 10/2017 | Ghaffari et al. |
| 11,123,011 | B1 | 9/2021 | Mishra et al. |
| 2003/0127706 | A1 | 7/2003 | Tanimura |
| 2003/0199743 | A1 | 10/2003 | Berlin |
| 2005/0101252 | A1 | 5/2005 | Carvalho et al. |
| 2006/0029991 | A1 | 2/2006 | Hagino et al. |
| 2006/0249389 | A1 | 11/2006 | Fenn et al. |
| 2006/0253011 | A1 | 11/2006 | Edmonson et al. |
| 2007/0056101 | A1 | 3/2007 | Mahajan et al. |
| 2008/0166029 | A1 | 7/2008 | Presura |
| 2008/0275310 | A1 | 11/2008 | Kim |
| 2009/0269003 | A1 | 10/2009 | Scully et al. |
| 2010/0063372 | A1 | 3/2010 | Potts et al. |
| 2010/0130843 | A1 | 5/2010 | Caceres Galvez et al. |
| 2010/0179403 | A1 | 7/2010 | Martinsen et al. |
| 2010/0302004 | A1 | 12/2010 | Winstead et al. |
| 2011/0152718 | A1 | 6/2011 | Revol-Cavalier |
| 2011/0215931 | A1 | 9/2011 | Callsen et al. |
| 2012/0042666 | A1 | 2/2012 | Besore |
| 2012/0065937 | A1 | 3/2012 | de Graff et al. |
| 2012/0252046 | A1 | 10/2012 | Fei et al. |
| 2013/0033476 | A1 | 2/2013 | Dean et al. |
| 2013/0092543 | A1 | 4/2013 | Heikenfeld |
| 2013/0125643 | A1 | 5/2013 | Batty et al. |
| 2013/0144136 | A1 | 6/2013 | Rymut |
| 2013/0192356 | A1 | 8/2013 | de Graff et al. |
| 2013/0245388 | A1 | 9/2013 | Rafferty et al. |
| 2013/0248380 | A1 | 9/2013 | Cui |
| 2013/0332114 | A1 | 12/2013 | Dasu et al. |
| 2014/0001058 | A1 | 1/2014 | Ghaffari et al. |
| 2014/0018641 | A1 | 1/2014 | Yoshino et al. |
| 2014/0022746 | A1 | 1/2014 | Hsu |
| 2014/0221792 | A1 | 8/2014 | Miller et al. |
| 2014/0257064 | A1 | 9/2014 | Einck et al. |
| 2015/0057515 | A1 | 2/2015 | Hagen et al. |
| 2015/0067066 | A1 | 3/2015 | Radhakrishnan |
| 2015/0108341 | A1 | 4/2015 | Shishika et al. |
| 2015/0112164 | A1 | 4/2015 | Heikenfeld et al. |
| 2015/0112165 | A1 | 4/2015 | Heikenfeld |
| 2015/0141775 | A1 | 5/2015 | Macaluso et al. |
| 2015/0165206 | A1 | 6/2015 | Venkatesan et al. |
| 2015/0289775 | A1 | 10/2015 | Chon et al. |
| 2015/0289820 | A1 | 10/2015 | Miller et al. |
| 2015/0305675 | A1 | 10/2015 | Miller et al. |
| 2015/0335254 | A1 | 11/2015 | Fastert et al. |
| 2015/0359469 | A1 | 12/2015 | Jacobs et al. |
| 2016/0051191 | A1 | 2/2016 | Miller et al. |
| 2016/0132732 | A1 | 5/2016 | Gunther et al. |
| 2016/0213424 | A1 | 7/2016 | Ghaffari et al. |
| 2016/0228640 | A1 | 8/2016 | Pindado et al. |
| 2016/0232807 | A1 | 8/2016 | Ghaffari et al. |
| 2016/0235374 | A1 | 8/2016 | Miller et al. |
| 2016/0240061 | A1* | 8/2016 | Li .................... A61B 5/6833 |
| 2016/0249847 | A1 | 9/2016 | Kennedy |
| 2016/0287148 | A1 | 10/2016 | Pizer et al. |
| 2016/0294789 | A1 | 10/2016 | Houghton et al. |
| 2016/0309594 | A1 | 10/2016 | Hsu |
| 2016/0371957 | A1 | 12/2016 | Ghaffari et al. |
| 2016/0374598 | A1 | 12/2016 | Heikenfeld et al. |
| 2017/0014043 | A1 | 1/2017 | Mcdonnell |
| 2017/0014067 | A1 | 1/2017 | Peppou et al. |
| 2017/0048975 | A1 | 2/2017 | Johnson et al. |
| 2017/0049397 | A1 | 2/2017 | Sun et al. |
| 2017/0071518 | A1 | 3/2017 | Xavier Da Silveira et al. |
| 2017/0079589 | A1 | 3/2017 | Ghaffari et al. |
| 2017/0083312 | A1 | 3/2017 | Pindado et al. |
| 2017/0086715 | A1 | 3/2017 | Iuele et al. |
| 2017/0086749 | A1 | 3/2017 | Ghaffari et al. |
| 2017/0095183 | A1 | 4/2017 | Heikenfeld |
| 2017/0095184 | A1 | 4/2017 | Heikenfeld |
| 2017/0095732 | A1 | 4/2017 | Ghaffari et al. |
| 2017/0100102 | A1 | 4/2017 | Heikenfeld |
| 2017/0105795 | A1 | 4/2017 | Lee et al. |
| 2017/0110417 | A1 | 4/2017 | Arora et al. |
| 2017/0143232 | A1 | 5/2017 | Yamaji |
| 2017/0156641 | A1 | 6/2017 | Nyberg et al. |
| 2017/0172470 | A1 | 6/2017 | Begtrup et al. |
| 2017/0172484 | A1 | 6/2017 | Sonner et al. |
| 2017/0173262 | A1 | 6/2017 | Veltz |
| 2017/0181659 | A1 | 6/2017 | Rafferty et al. |
| 2017/0186727 | A1 | 6/2017 | Dalal et al. |
| 2017/0188942 | A1 | 7/2017 | Ghaffari et al. |
| 2017/0191521 | A1 | 7/2017 | Hopkins |
| 2017/0200670 | A1 | 7/2017 | Rafferty et al. |
| 2017/0215773 | A1 | 8/2017 | Heikenfeld et al. |
| 2017/0220772 | A1 | 8/2017 | Vleugels et al. |
| 2017/0223844 | A1 | 8/2017 | Pizer et al. |
| 2017/0238854 | A1 | 8/2017 | Henshaw |
| 2017/0243464 | A1 | 8/2017 | Diaz |
| 2017/0244285 | A1 | 8/2017 | Raj et al. |
| 2017/0245788 | A1 | 8/2017 | Heikenfeld |
| 2017/0296114 | A1 | 10/2017 | Ghaffari et al. |
| 2017/0303788 | A1 | 10/2017 | Xavier da Silveira et al. |
| 2018/0020966 | A1 | 1/2018 | Begtrup et al. |
| 2018/0064377 | A1 | 3/2018 | Rogers et al. |
| 2018/0220967 | A1* | 8/2018 | Wang .................. A61B 5/1477 |
| 2018/0256137 | A1 | 9/2018 | Heikenfeld et al. |
| 2019/0008448 | A1 | 1/2019 | Begtrup et al. |

(56) References Cited

U.S. PATENT DOCUMENTS

| | | | |
|---|---|---|---|
| 2019/0117170 A1 | 4/2019 | Begtrup et al. | |
| 2019/0192001 A1 | 6/2019 | Heikenfeld et al. | |
| 2019/0192009 A1 | 6/2019 | Reifman et al. | |
| 2019/0227022 A1 | 7/2019 | Harley-Trochimczyk et al. | |
| 2019/0231236 A1 | 8/2019 | Heikenfeld et al. | |
| 2019/0290186 A1 | 9/2019 | Adachi et al. | |
| 2020/0205895 A1* | 7/2020 | Butterworth | A61B 18/1815 |
| 2021/0077019 A1 | 3/2021 | Kendall et al. | |
| 2021/0145325 A1* | 5/2021 | Matsumoto | A61B 5/681 |
| 2021/0290156 A1 | 9/2021 | Mishra et al. | |
| 2023/0172541 A1 | 6/2023 | Mishra et al. | |

FOREIGN PATENT DOCUMENTS

| | | | |
|---|---|---|---|
| CA | 2913483 A1 | 12/2014 | |
| CA | 2927213 A1 | 4/2015 | |
| CA | 2950594 A1 | 12/2015 | |
| CA | 2959699 A1 | 4/2016 | |
| CA | 2965658 A1 | 5/2016 | |
| CA | 2910385 C | 11/2017 | |
| CN | 105997071 A | 10/2016 | |
| CN | 108451502 A | 8/2018 | |
| CN | 108471940 A | 8/2018 | |
| EP | 1397940 B1 | 4/2005 | |
| EP | 1700147 B1 | 10/2009 | |
| EP | 2385914 A2 | 11/2011 | |
| EP | 2587240 A2 | 5/2013 | |
| EP | 2902294 A2 | 8/2015 | |
| EP | 3364183 A1 | 8/2018 | |
| EP | 2938982 B1 | 11/2018 | |
| EP | 2834007 B1 | 6/2019 | |
| EP | 3148415 B1 | 10/2019 | |
| JP | 2004254995 A | 9/2004 | |
| JP | 2009247440 A | 10/2009 | |
| JP | 2013090894 A | 5/2013 | |
| JP | 2013192650 A | 9/2013 | |
| JP | 2014-138645 A | 7/2014 | |
| JP | 2015154928 A | 8/2015 | |
| JP | 2015200671 A | 11/2015 | |
| JP | 2016006880 A | 1/2016 | |
| JP | 2016154017 A | 8/2016 | |
| JP | 2016213515 A | 12/2016 | |
| JP | 2017035505 A | 2/2017 | |
| JP | 2017108160 A | 6/2017 | |
| JP | 3212682 U | 9/2017 | |
| JP | 2017533440 A | 11/2017 | |
| JP | 2018013395 A | 1/2018 | |
| WO | WO-2002073708 A2 | 9/2002 | |
| WO | WO-2005002006 A2 | 1/2005 | |
| WO | WO-2005114740 A1 | 12/2005 | |
| WO | WO-2006017129 A2 | 2/2006 | |
| WO | WO-2006121597 A2 | 11/2006 | |
| WO | WO-2008039832 A2 | 4/2008 | |
| WO | WO-2010042957 A2 | 4/2010 | |
| WO | WO-2010102310 A2 | 9/2010 | |
| WO | WO-2010104606 A1 | 9/2010 | |
| WO | WO-2011127331 A2 | 10/2011 | |
| WO | WO-2012091776 A2 | 7/2012 | |
| WO | WO-2013010171 A1 | 1/2013 | |
| WO | WO-2013049716 A1 | 4/2013 | |
| WO | WO-2013152087 A2 | 10/2013 | |
| WO | WO-2014039794 A2 | 3/2014 | |
| WO | WO-2014165071 A1 | 10/2014 | |
| WO | WO-2014197443 A1 | 12/2014 | |
| WO | WO-2015020367 A1 | 2/2015 | |
| WO | WO-2015054312 A1 | 4/2015 | |
| WO | WO-2015054506 A2 | 4/2015 | |
| WO | WO-2015058055 A1 | 4/2015 | |
| WO | WO-2015077559 A1 | 5/2015 | |
| WO | WO-2015080991 A1 | 6/2015 | |
| WO | WO-2015102951 A2 | 7/2015 | |
| WO | WO-2015103483 A1 | 7/2015 | |
| WO | WO-2015103580 A2 | 7/2015 | |
| WO | WO-2015138712 A2 | 7/2015 | |
| WO | WO-2015127458 A1 | 8/2015 | |
| WO | WO-2015134588 A1 | 9/2015 | |
| WO | WO-2015184072 A1 | 12/2015 | |
| WO | WO-2015184084 A2 | 12/2015 | |
| WO | WO-2015184097 A2 | 12/2015 | |
| WO | WO-2016003482 A1 | 1/2016 | |
| WO | WO-2016007944 A2 | 1/2016 | |
| WO | WO-2016030869 A1 | 3/2016 | |
| WO | WO-2016048888 A1 | 3/2016 | |
| WO | WO-2016073395 A1 | 5/2016 | |
| WO | WO-2016089957 A1 | 6/2016 | |
| WO | WO-2016130905 A1 | 8/2016 | |
| WO | WO-2016134235 A1 | 8/2016 | |
| WO | WO-2016134306 A1 | 8/2016 | |
| WO | WO-2016138087 A1 | 9/2016 | |
| WO | WO-2016140961 A1 | 9/2016 | |
| WO | WO-2016142359 A1 | 9/2016 | |
| WO | WO-2016144529 A1 | 9/2016 | |
| WO | WO-2016187536 A1 | 11/2016 | |
| WO | WO-2016191594 A1 | 12/2016 | |
| WO | WO-2016197085 A1 | 12/2016 | |
| WO | WO-2016197116 A1 | 12/2016 | |
| WO | WO-2016205385 A1 | 12/2016 | |
| WO | WO-2017015000 A1 | 1/2017 | |
| WO | WO-2017019573 A1 | 2/2017 | |
| WO | WO-2017019602 A1 | 2/2017 | |
| WO | WO-2017031393 A1 | 2/2017 | |
| WO | WO-2017044617 A1 | 3/2017 | |
| WO | WO-2017044731 A1 | 3/2017 | |
| WO | WO-2017051679 A1 | 3/2017 | |
| WO | WO-2017053919 A1 | 3/2017 | |
| WO | WO-2017058806 A1 | 4/2017 | |
| WO | WO-2017062508 A1 | 4/2017 | |
| WO | WO-2017070640 A1 | 4/2017 | |
| WO | WO-2017070641 A1 | 4/2017 | |
| WO | WO-2017075402 A1 | 5/2017 | |
| WO | WO-2017095861 A1 | 6/2017 | |
| WO | WO-2017112023 A2 | 6/2017 | |
| WO | WO-2017123954 A1 | 7/2017 | |
| WO | WO-2017147052 A1 | 8/2017 | |
| WO | WO-2017189612 A1 | 11/2017 | |
| WO | WO-2017190049 A1 | 11/2017 | |
| WO | WO-2018071895 A1 | 4/2018 | |
| WO | WO-2018186748 A1 | 10/2018 | |
| WO | WO-2020102439 A1 | 5/2020 | |
| WO | WO-2021/194987 A1 | 9/2021 | |

OTHER PUBLICATIONS

International Preliminary Report on Patentability for International Patent Application No. PCT/US2021/023518, Sep. 22, 2022, 7 pages.

International Preliminary Report on Patentability for International Patent Application No. PCT/US2019/061301, May 18, 2021, 10 pages.

Baker, L.B. et al. (2019) "Exercise intensity effects on total sweat electrolyte losses and regional vs. whole-body sweat [Na+], [Cl−], and [K+]" Eur J Appl Physiol, 119:361-375.

Del Coso, J. et al. (2013) "Influence of body mass loss and myoglobinuria on the development of muscle fatigue after a marathon in a warm environment" Appl Physiol Nutr Metab, 38:286-291.

Gopinathan, P.M. et al. "Role of Dehydration in Heat Stress-Induced Variations in Mental Performance" Archives of Environmental Health, 43(1):15-17.

Holmes, N. et al. (2016) "The Effect of Exercise Intensity on Sweat Rate and Sweat Sodium and Potassium Losses in Trained Endurance Athletes" Ann Sports Med Res, 3(2):1063, 4 pages.

International Search Report and Written Opinion, mailed Feb. 5, 2020, in International Patent Application No. PCT/US2019/061301, filed Nov. 13, 2019 by Nix, Inc.; 17 pages.

International Search Report and Written Opinion, mailed Jun. 4, 2021, in International Patent Application No. PCT/US2021/023518, filed Mar. 22, 2021 by Nix, Inc.; 15 pages.

Judelson, D.A. et al. (2007) "Hydration and Muscular Performance Does Fluid Balance Affect Strength, Power and High-Intensity Endurance?" Sports Med, 37(10):907-921.

(56)                 References Cited

OTHER PUBLICATIONS

Liu, G. et al (Dec. 15, 2015) "A wearable conductivity sensor for wireless real-time sweat monitoring" Sensors and Actuators B: Chemical, 227:35-42.
Martin, A. et al. (Dec. 22, 2017) "Epidermal Microfluidic Electrochemical Detection System: Enhanced Sweat Sampling and Metabolite Detection" ACS Sensors, 2(12):1860-1868.
Maughan, R.J. (2003) "Impact of mild dehydration on wellness and on exercise performance" Eur J Clin Nutr, 57(Suppl 2):S19-S23.
Niedermann, R. et al. (2014) "Prediction of human core body temperature using non-invasive measurement methods" Int J Biometerol, 58:7-15.
Nyein, H.Y.Y. et al. (May 9, 2018) "A Wearable Microfluidic Sensing Patch for Dynamic Sweat Secretion Analysis" ACS Sensors, 3(5):944-952.
Summers, R.L. et al. (2010) "Ultrasound measurements of lower extremity soft tissue and interstitial fluid thickness may be used as an early indicator of dehydration" Crit Ultrasound, 2:43-45.

* cited by examiner

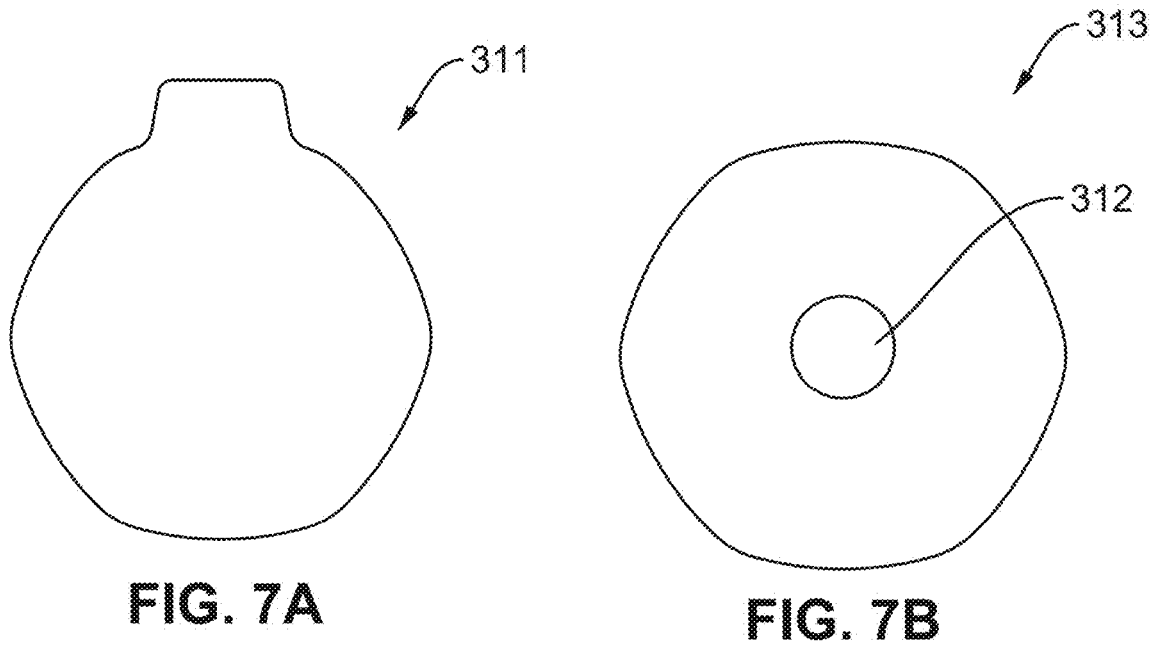
—311
FIG. 7A
—313
—312
FIG. 7B
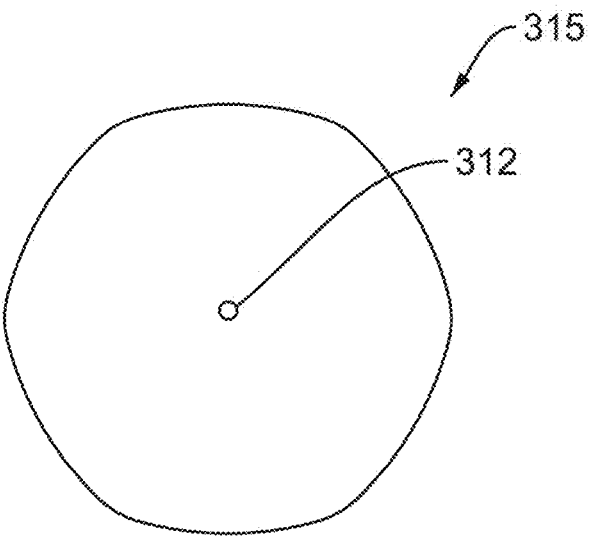
—315
—312
FIG. 7C

315

320

321

323

320b

320b

320a

318

320a

316

324

330

342

330

330

14          14

330

330

510

710

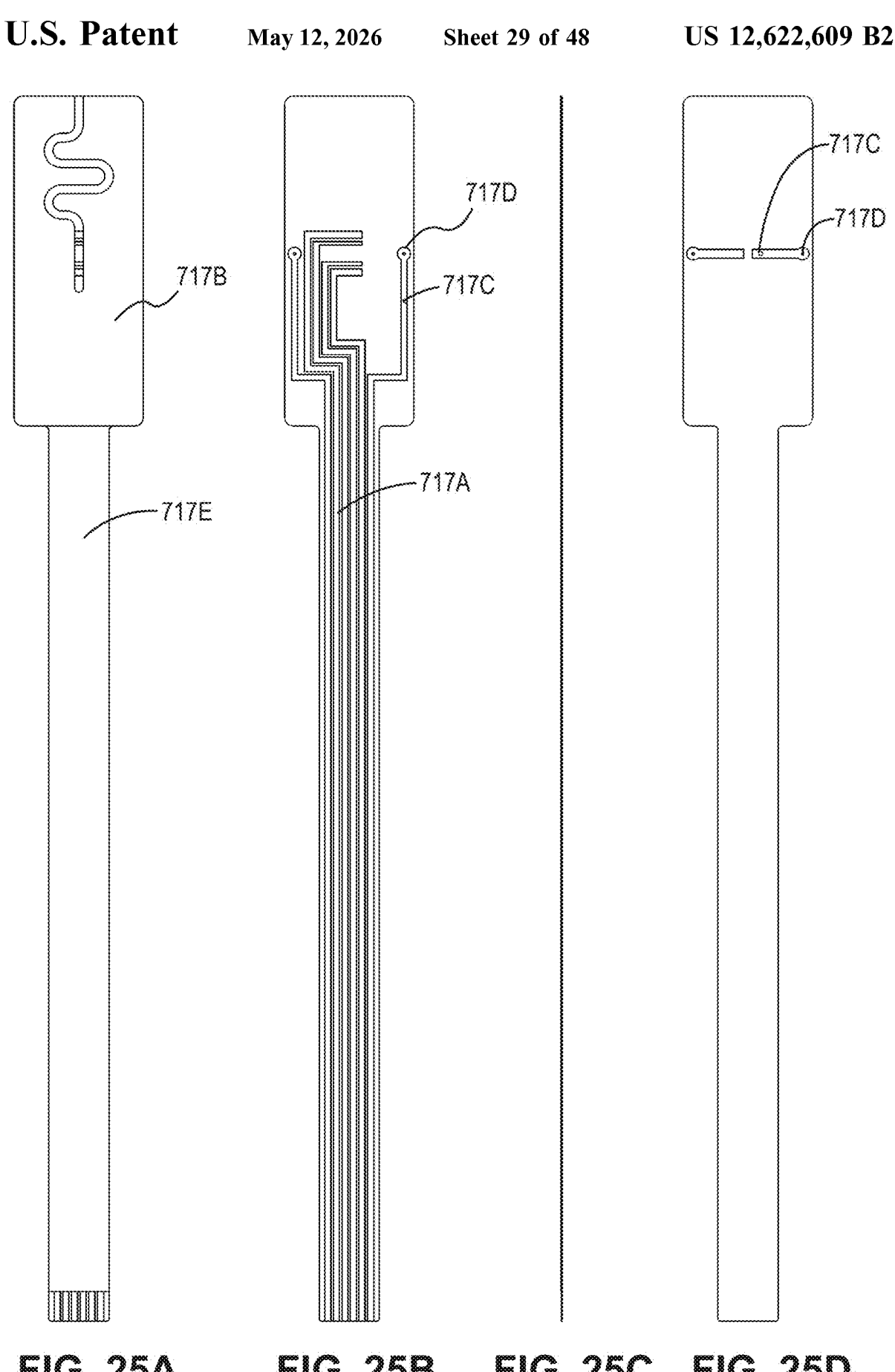
FIG. 25A     FIG. 25B     FIG. 25C     FIG. 25D

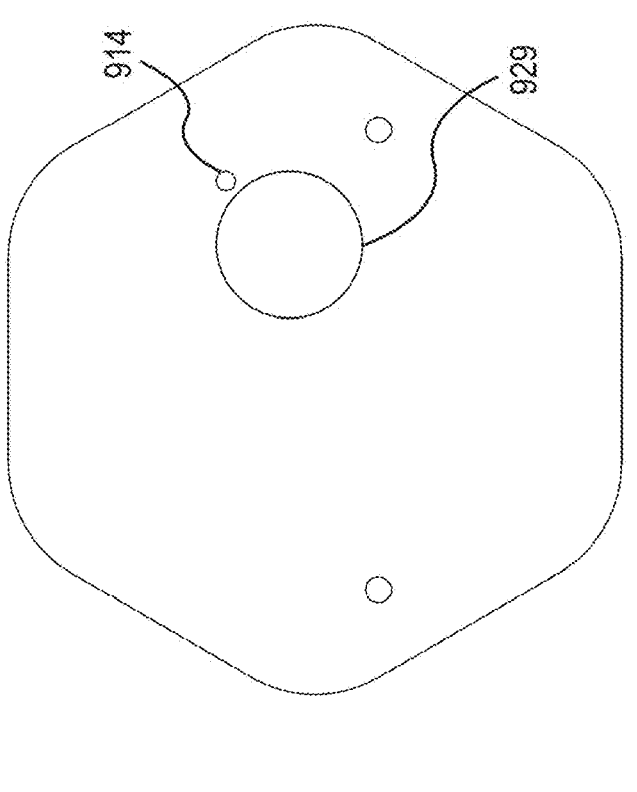
FIG. 36C
FIG. 36B
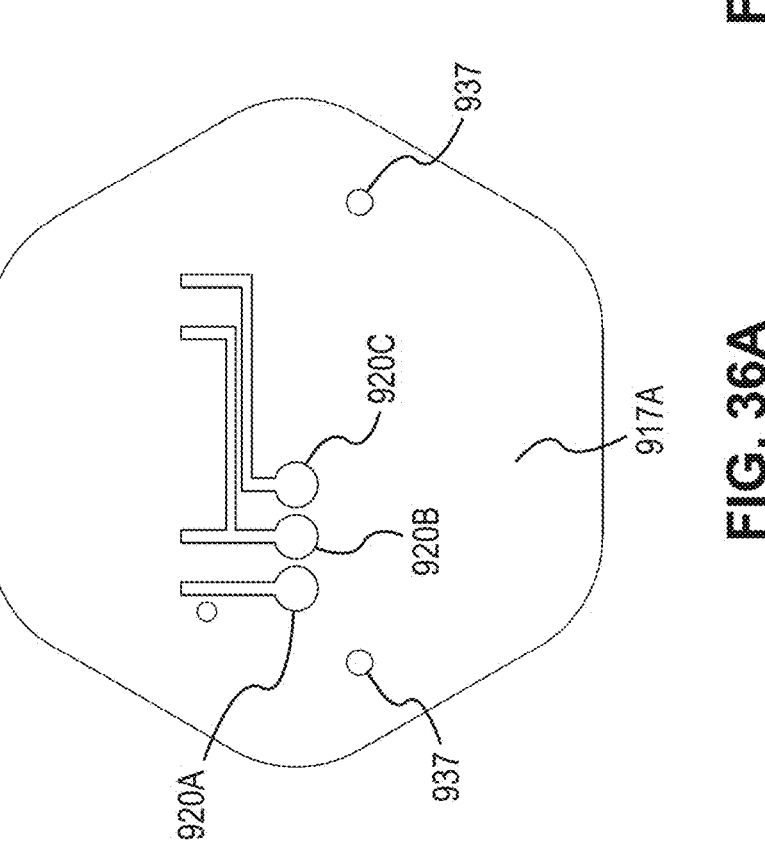
FIG. 36A

WEARABLE SYSTEMS, DEVICES AND METHODS FOR MEASUREMENT AND ANALYSIS OF BODY FLUIDS

CROSS-REFERENCE TO RELATED APPLICATIONS

This application is a continuation of International Patent Application No. PCT/US2019/061301, entitled "Wearable systems, devices, and methods for measurement and analysis of body fluids," filed Nov. 13, 2019, which claims priority to and the benefit of U.S. Provisional Application No. 62/760,202, entitled "Wearable systems, devices, and methods for measurement and analysis of body fluids", filed Nov. 13, 2018, the entire contents of which are hereby expressly incorporated by reference for all purposes.

TECHNICAL FIELD

Embodiments described herein relate to systems, devices, and methods for use in the near instantaneous measurement and analysis of body fluids and potential analytes contained therein. Embodiments described herein also relate to the implementation of a real-time hydration detection system and hydration strategizing system for use during activity.

SUMMARY

Systems, devices and methods are described herein for various embodiments of a sample analysis system that is worn by a user, the sample analysis system configured to collect a sample of bodily fluid, and measure and analyze the bodily fluid to determine a property of the bodily fluid and/or a health parameter (e.g., degree of hydration, electrolyte losses, perspiration rate, etc.) of the user.

BRIEF DESCRIPTION OF THE FIGURES

FIG. 7A-7C schematically illustrate the component layers of the sample handling device of FIGS. 5A, 5B, and 6.

FIG. 25A is a schematic illustration of a bottom view of an electrode and channel layer of the sample handling device of FIG. 21, according to an implementation.

FIG. 25B-25D are schematic illustrations of a top view, side view, and bottom view, respectively, of an electrode layer of the sample handling device of FIG. 21, according to an implementation.

FIG. 31 is a schematic illustration of a top view of a sample handling device that can be used with an example SA system, according to an embodiment.

FIG. 32 is a schematic illustration of a top view of the sample handling device of FIG. 31, mounted on a snap ring interface, to be used with an example SA system, according to an embodiment.

FIG. 36A-36C are schematic illustrations of a top view of an electrode layer, a side view of the electrode layer, and a bottom view including a spacer portion of an electrode layer of the sample handling device of FIG. 31, according to an implementation.

DETAILED DESCRIPTION

Figure 1:
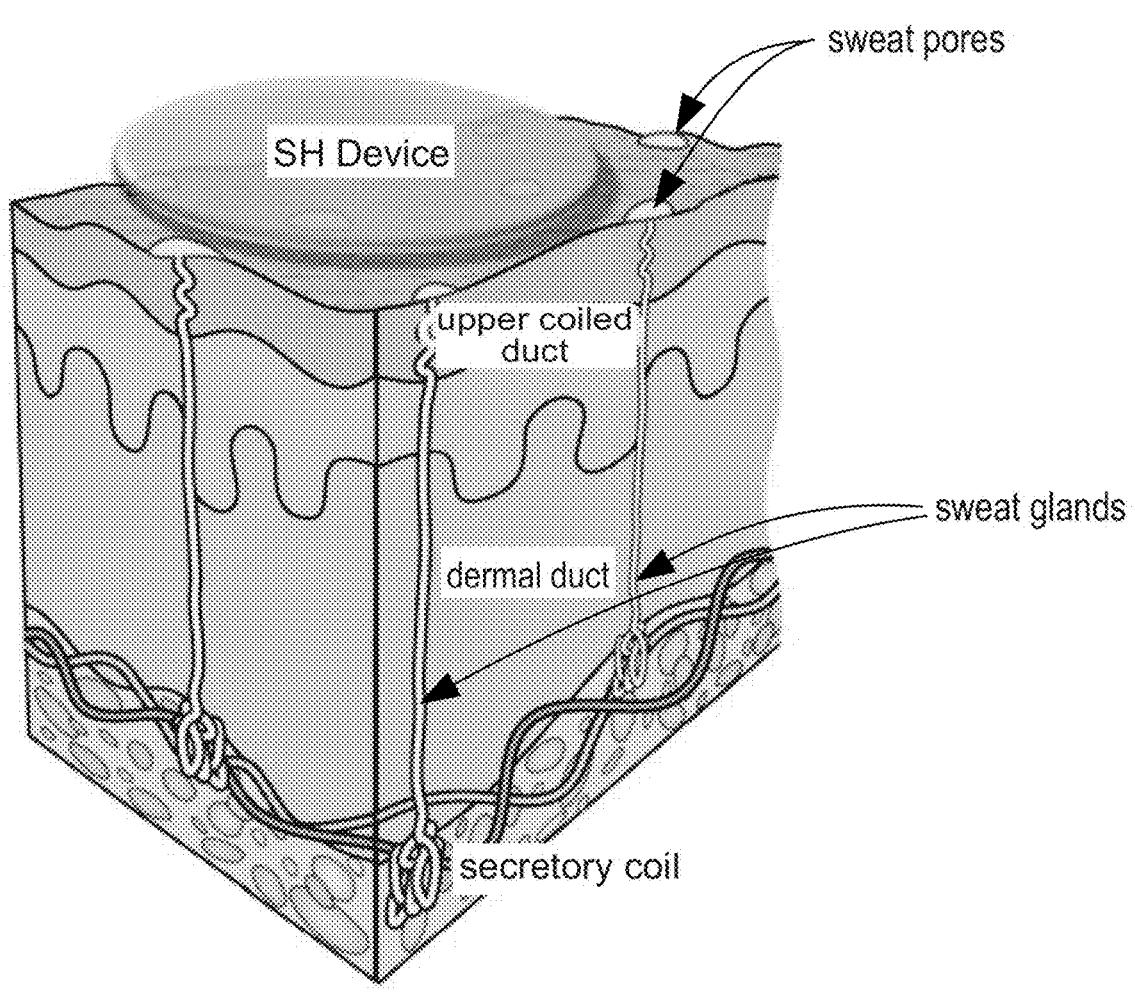
FIG. 1 is a schematic illustration of an example use of a sample handling device on a skin surface of a user, according to an embodiment.

Embodiments disclosed relate generally to systems, devices, and methods for use in the near instantaneous measurement and analysis of body fluids and potential analytes contained therein. Embodiments described herein also relate to the implementation of a real-time hydration detection system and hydration strategizing system for use during activity.

In one embodiment, a method is disclosed comprising collecting a sample of bodily fluid in a sample collection region of a wearable device from a source of bodily fluid, and directing a portion of the sample of bodily fluid from the sample collection region to a set of electrodes. The set of electrodes can include an excitation electrode and a sensing electrode. The method comprises applying an excitation signal through the portion of the sample of bodily fluid, and sensing a response signal in response to the excitation signal. The method further comprises measuring an impedance associated with the portion of the sample of bodily fluid, based on the response signal, and determining, based on the impedance, a property of the source of bodily fluid.

In one embodiment, a wearable apparatus is disclosed comprising a sample collection region, having an inlet and configured to receive, via the inlet, an initial volume of bodily fluid. The wearable apparatus includes an access port in fluidic communication with the sample collection region, and a flow channel, in fluid communication with the access port. The flow channel is configured to direct a portion of the initial volume of bodily fluid towards a set of electrodes. The set of electrodes include an excitation electrode and a sensing electrode. The excitation electrode is configured to apply an excitation signal to the portion of the initial volume of bodily fluid, and the sensing electrode is configured to receive a response signal from the portion of the initial volume of bodily fluid in response to the excitation signal. The sensing electrode is configured to transmit the response signal to a processor to calculate an impedance associated with the portion of the initial volume of bodily fluid.

In one embodiment, a system is disclosed comprising a memory storing a set of instructions, a processor coupled to the memory, and configured to execute the instructions stored in the memory, and a wearable device. The wearable device includes a sample collection region configured to receive an initial volume of bodily fluid, an access port in fluidic communication with the sample collection region, and a flow channel, in fluid communication with the access port. The flow channel is configured to direct a portion of the initial volume of bodily fluid towards a set of electrodes including an excitation electrode and a sensing electrode. The excitation electrode is configured to apply an excitation signal to the portion of the initial volume of bodily fluid, and the sensing electrode is configured to receive a response signal from the portion of the initial volume of bodily fluid and in response to the excitation signal.

In one embodiment, a device for measuring a biophysical property of a sample of bodily fluid is disclosed comprising an interface layer, an adhesive layer, an access port layer, a channel layer, and an electrode layer. The interface layer includes a liner configured to be released to affix the device on a body of a user. The adhesive layer has a predefined thickness, includes an adhesive proximal surface to be affixed on the body of the user, and includes an adhesive distal surface to be affixed to the access port layer. The adhesive layer defines an opening via which to receive the sample of bodily fluid. The access port layer includes a proximal surface configured to be affixed to the distal surface of the adhesive layer, the adhesive layer and the access port layer collectively defining a sample collection region, and a distal surface. The access port layer defines an access port to urge a flow of bodily fluid from the sample collection region. The channel layer defines a flow channel configured to direct the flow of the bodily fluid from the sample collection region. The flow channel includes a test region configured to test a portion of the sample of bodily fluid for a property of the bodily fluid. The electrode layer is configured to define a set of electrodes and to interface with the flow channel at the test region. The set of electrodes includes (i) an excitation electrode configured to apply an excitation signal to the portion of the sample of bodily fluid at the test region, and (ii) a sensing electrode configured to receive a response signal from the portion of the sample of bodily fluid, in response to the applying the excitation signal at the test region. The set of electrodes further includes terminal connections to provide electrical communication between the set of electrodes and a processor to which to send the response signal to be processed.

Embodiments described herein relate to systems, devices, and methods for use in the measurement and analysis of bodily fluids using wearable system of measurement and analysis. A sample analysis system can be configured to collect a sample of bodily fluid, and measure and analyze the bodily fluid to determine a property (e.g., osmolality) of the bodily fluid and/or a health parameter (e.g., degree of hydration, electrolyte losses, perspiration rate, etc.) of the user. For example, systems and devices as described herein can collect a sample of bodily fluid (e.g., sweat) and measure the impedance of the bodily fluid. The impedance measurement can then be used to determine and/or predict a property (e.g., osmolality) of the sweat. Without wishing to be bound by any particular theory, it is believed that the electrolyte content of the sweat is a primary contributor to the osmolality of the sweat; therefor the determined osmolality can be used to estimate the electrolyte content of the sweat. The sweat data can then be used to determine or predict a health parameter (e.g., degree of hydration, electrolyte losses, perspiration rate, etc.) of the user.

Although the system is described above as being used to determine the electrolyte content of sweat based on an impedance measurement, the system can also be used to determine the osmolality of other bodily fluids and/or secretions including, for example, saliva, tears, urine, breast milk, etc., which can provide insights about hydration or other health parameters of the users. In addition, without wishing to be bound by any particular theory, some scientific evidence suggests that the osmolality of breast milk can be used to determine the nutritional content of the breast milk. Thus, similar to the analysis described above, the system can be used to measure the impedance of breast milk, which can be correlated to the osmolality of breast milk to provide insights about its nutritional content.

As described herein, individuals such as athletes, military service members, laborers, children, the elderly, patients under critical care, and the general population can immensely benefit from timely monitoring of their health and well-being, using suitable indicators of a state of health, and timely intervention or correction based on the monitoring. Some example secondary indicators of health and well-being include a degree of hydration, body water losses, and indications of electrolyte losses, which can be an indicator of electrolyte balance/imbalance.

Studies show that up to 87% of endurance athletes are physically impaired during their workouts and competitions due to dehydration, despite ample access to fluids. Dehydration can cause decreased blood pressure, increase heart rate, increased respiratory rate, and decreased blood flow to extremities. These physiological changes can lead to cardiorespiratory stress, impaired thermoregulation, and fatigue—all of which have a significant impact on patient health or athletic performance. Because the symptoms of mild dehydration are subtle—often imperceptible—individuals suffer the consequences without always knowing it.

Dehydration causes athletic performance to deteriorate after just 1% of body weight loss and worsens exponentially with each percent lost. An athlete can significantly lose the ability to perform and have an impaired level of function at around 5% of body water loss by weight. Dehydration also leads to cognitive impairment, in addition to the physical impairment. Studies show dehydration can also increase the risk of other injury, such as soft tissue injury and traumatic brain injury. If an athlete's level of dehydration reaches critical levels, medical intervention is required to prevent permanent side effects or major bodily system shutdown. In the extreme cases, even death can occur. Because athletes do not have a way of effectively monitoring their hydration status during a workout, they often misunderstand how easily and quickly it can occur. Effects of dehydration in children, the elderly, and patients in critical care can be even more precipitated and/or damaging.

Managing hydration is complicated by a high degree of variability in sweat rates. Each individual can sweat at a different rate based on individual factors like gender, body mass, and fitness level, among other factors. For any individual athlete there are a number of additional variables that affect sweat rate from weather conditions, intensity of the workout, the amount and types of clothing or equipment worn, etc. The same athlete can have different sweat rates for the same activity on any given day.

One method for measuring degree of hydration of an athlete is to record nude body mass before and after an activity. The difference in the before and after measurements is converted to a percentage body weight lost. Since this method for measuring dehydration can only be performed with measurements before and after an activity, athletes currently cannot determine their hydration status during the performance of the activity.

Other methods used to measure hydration status include collecting blood samples at regular intervals during activity and measuring the osmolality of the plasma with an osmometer. As current methods of collection of blood sample cannot be performed during an activity, this method has some of same problems as mentioned for nude body mass measurement method. It provides hydration status information before or after an activity, but not during. Similar to collecting blood for plasma osmolality measurement, available methods of collection of other bodily fluids for osmolality measurement as a way of determining hydration status is also used with less successful results. The other fluids collected include saliva, urine, sweat and tears. Each of these fluids present challenges with both collection and osmolality measurement.

Some devices collect sweat with a patch that adheres to the skin. The sweat can either be collected into an absorbent patch or reservoir. The patch is then removed from the athlete and electrical conductance of the sweat in the patch measured with a benchtop device. A significant amount of sweat is required for this method; the athlete must be in a full sweat for 15 to 20 minutes to collect this minimum amount. This method cannot provide live, instantaneous hydration monitoring to the athlete. In addition, these patches need to be replaced every 15 to 20 minutes to be able to collect an accurate hydration status for the entire period of activity being studied. Thus, there exists a need for systems, devices, and methods for use in the near instantaneous measurement and analysis of body fluids A Sample Analysis System Embodiments described herein relate to systems, devices, and methods for use in the near instantaneous measurement and analysis of body fluids such as sweat and potential analytes contained therein. The disclosed embodiments of systems and devices are lightweight in nature and therefore can be worn by an individual during any form of activity. The disclosed systems, devices, and methods allow near instantaneous measurement and analysis of body fluids by their stand-alone, real-time nature of sample collection and analysis. The disclosed embodiments of systems and methods also support repeated instantaneous measurements of samples of bodily fluid, carried out over a period of time while the individual is engaged in the activity.

As used herein, the terms "analyte" and/or "target analyte" refer to any ion, molecule or compound to be detected and/or that can bind to a binding species (e.g., a detection molecule or reagent), as described herein. Suitable analytes can include but are not limited to, metal and non-metal ions (e.g., $Na^+$, $Cl^-$, $Ca^{2+}$, $K^+$, or $Mg^{2+}$ ions), nitrogenous compounds such as amino acids and urea, metabolites (e.g., lactates and pyruvates), xenobiotics such as drug molecules enzymes, metabolic by-products, disease related biomarkers, small chemical molecules such as, for example, environmental molecules, clinical molecules, chemicals, pollutants, and/or biomolecules. More specifically, such chemical molecules can include but are not limited to pesticides, insecticides, toxins, therapeutic and/or abused drugs, hormones, antibiotics, antibodies, organic materials, proteins (e.g., enzymes, immunoglobulins, and/or glycoproteins), nucleic acids (e.g., DNA and/or RNA), lipids, lectins, carbohydrates, whole cells (e.g., prokaryotic cells such as pathogenic bacteria and/or eukaryotic cells such as mammalian tumor cells), viruses, spores, polysaccharides, glycoproteins, metabolites, cofactors, nucleotides, polynucleotides, transition state analogs, inhibitors, nutrients, electrolytes, growth factors and other biomolecules and/or non-biomolecules, as well as fragments and combinations thereof. Some analytes described herein can be proteins such as enzymes, drugs, cells, antibodies, antigens, cellular membrane antigens, and/or receptors or their ligands (e.g., neural receptors or their ligands, hormonal receptors or their ligands, nutrient receptors or their ligands, and/or cell surface receptors or their ligands).

As used herein, the term "sample" refers to a composition that contains an analyte or analytes to be detected. A sample can be heterogeneous, containing a variety of components (e.g., different proteins) or homogenous, containing one component. In some instances, a sample can be naturally occurring, a biological material, and/or a man-made material. Furthermore, a sample can be in a native or denatured form. In some instances, processing may be performed on a sample prior to detecting an analyte. For example, a sample can be subjected to a lysing step, denaturation step, heating step, purification step, precipitation step, immunoprecipitation step, column chromatography step, centrifugation, etc. In some instances, separation and/or immobilization (via electrophoresis) of a sample can be performed on native substrates and/or an analyte of interest (e.g., a protein). In other instances, a sample can undergo denaturation to expose their internal hydrophobic groups for immobilizing in a fluid path.

As used in this specification and the claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used in this specification, the term "and/or" is used in this disclosure to mean either "and" or "or" unless indicated otherwise.

As used herein, "bodily fluid" can include any fluid obtained from a body of an individual (e.g., athlete, patient, etc.). For example, "bodily fluid" includes, but is not limited to, sweat, tears, blood, urine, breast milk, saliva, sebaceous fluid, mucus, vitreous, and the like, or any combination thereof.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 10% or less in either direction (greater than or less than) of the stated reference value unless otherwise stated or otherwise evident from the context (except where such number would exceed 100% of a possible value or fall below 0% of a possible value).

As used herein, the term "stiffness" is related to an object's resistance to deflection, deformation, and/or displacement that is produced by an applied force, and is generally understood to be the opposite of the object's "flexibility." For example, a wall with greater stiffness is more resistant to deflection, deformation and/or displacement when exposed to a force than a wall having a lower stiffness. Similarly stated, an object having a higher stiffness can be characterized as being more rigid than an object having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

As used herein, the words "proximal" and "distal" refer to the direction closer to and away from, respectively, a user who would place the device or system against their body. Thus, for example, the end of a device first touching the body of the user would be the proximal end, while the opposite end of the device (e.g., the end of the device away from the body of the user) would be the distal end of the device.

As described in further detail herein, any of the systems, devices and methods can be used to collect and analyze bodily fluid samples in a repeated manner by, for example, collecting a first sample or a first volume of bodily fluid, testing that first volume or sample of the bodily fluid, expelling the first volume or sample of bodily fluid, and collecting a subsequent volume or sample of bodily after a given duration of time. Each of the terms "first." "subsequent" and/or "initial," can be used interchangeably to describe and/or refer to an amount, portion, or volume of bodily fluid that is collected, transferred, diverted, channeled and/or expelled during use of the sample analysis systems described herein. In some embodiments, the terms "first," "subsequent", and/or "initial" can refer to a predetermined, defined, desired, or given volume, portion, or amount of bodily fluid, that can depend on several parameters including device configuration, user needs, etc.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof.

The embodiments described herein and/or portions thereof can include components formed of one or more parts, features, structures, etc. When referring to such components it should be understood that the components can be formed by a singular part having any number of sections, layers, regions, portions, and/or characteristics, or can be formed by multiple parts or features. For example, when referring to a structure such as a wall or chamber, the structure can be considered as a single structure with multiple portions, or multiple, distinct substructures or the like coupled to form the structure. Thus, a monolithic structure can include, for example, a set of substructures. Such a set of substructures may include multiple portions that are either continuous or discontinuous from each other. A set of substructures can also be fabricated from multiple items or components that are produced separately and are later joined together (e.g., via a weld, an adhesive, or any suitable method).

A sample analysis system (also referred to herein as "SA system"), according to some embodiments, includes a one-time use sample handling device and a durable, sample processing device that connects to the sample handling device. In some implementations, a sample analysis system, according to some embodiments, can include a disposable sample handling device and a disposable sample processing device that connects to the sample handling device. The sample handling device is configured to collect a sample of bodily fluid, direct the sample to a testing and measurement interface, and allow testing of the sample with a test stimulus and measurement of a response signal from the sample in response to the test stimulus. After the testing of the collected sample, the sample handling device is configured to direct the sample to be expelled. The response signal can then be analyzed to determine quantitative properties of the sample, such as solute concentration, solvent content, analyte concentration, etc.

Sample Handing Deice

FIG. 1 shows a schematic representation of a section of skin of a user and illustrates an example sample handling device positioned on the skin of the user. The schematic of the skin section shows a density of secretory glands (e.g., sweat glands) leading to pores that release a bodily fluid (e.g., sweat). The sample handing device (also referred to herein as "SH Device") is represented by a disc and shown to be positioned on the surface of the skin of a user. As shown, the disc is covering a subset of the pores releasing the bodily fluid and is configured to collect the sample bodily fluid (e.g., sweat) from the user that can be measured and analyzed while the user engages in an activity (i.e., in near real-time). Although the sample handling device is shown on the skin of the user for collecting and analyzing sweat, it should be understood that the sample analysis systems described herein including the sample handling device can be used without being attached to the user and can be used for analyzing any number of other bodily fluids.

Figure 2A:
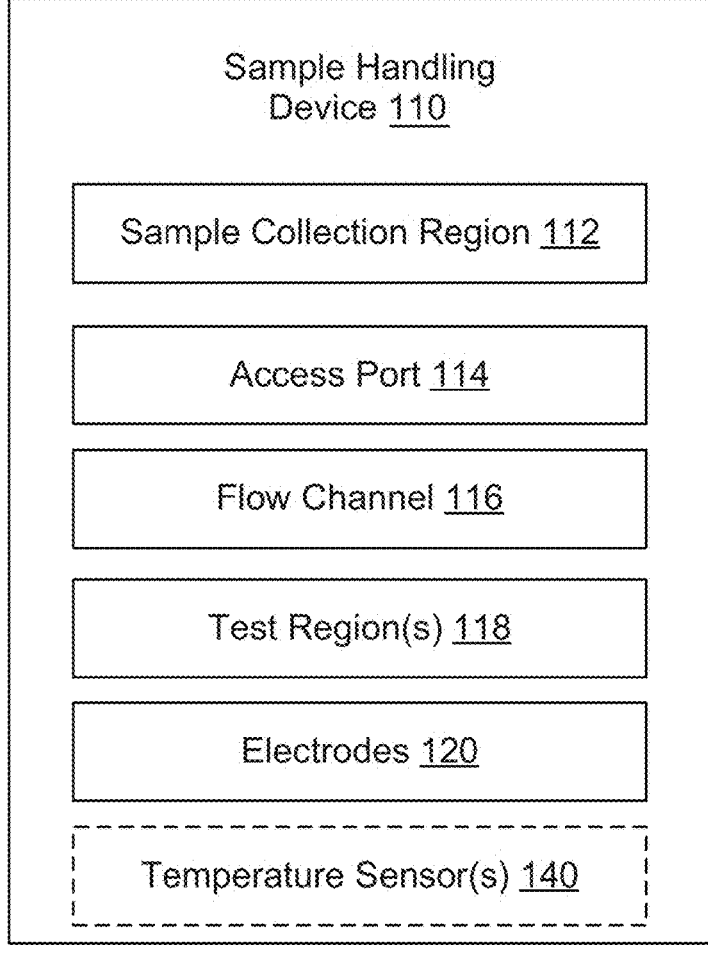
FIGS. 2A and 2B are schematic illustrations of a Sample Handling Device, according to an embodiment. The Sample Handling Device can be used with a Sample Analysis System ("SA system").
Figure 2B:
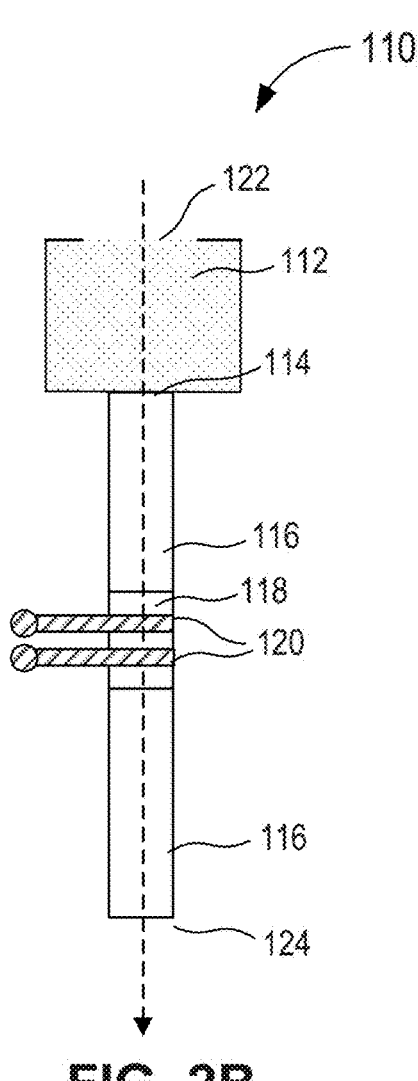

FIGS. 2A and 2B are schematic illustrations of an example sample handling device 110 indicating some components included in the sample handling device 110, according to an embodiment. Schematic in FIG. 2B includes an illustration of an example configuration of the various components of the sample handling device 110, and a flow path defined for the flow of a sample of bodily fluid indicated by the dashed arrow. In some embodiments, the sample handling device 110 can be constructed monolithically. In some other embodiments, the sample handling device 110 can be constructed through assembly of a set of portions or layers, as described in further detail herein. As shown in FIGS. 2A and 2B, the sample handling device 110 includes a sample collection region 112, an access port 114, a flow channel 116, a test region(s) 118, a set of electrodes 120, and optionally a temperature sensor 140.

The sample collection region 112 is a portion of the sample handling device 110 that is configured to receive and collect a bodily fluid sample, for example sweat, from the body of a user when the sample handling device 110 is worn by the user. The sample collection device 112 includes an opening 122, indicated in FIG. 2B, that permits access to a source of bodily fluid when the sample handling device 110 is worn by a user. The sample collection region 112 also defines a space or volume configured to be fluidically coupled to the opening 122 and configured to hold or collect a sample of bodily fluid when the sample handling device 110 is worn by the user. While not shown in the FIGS. 2A and 2B, the sampling handling device 110 can include one or more interfacing structures between the user's body and the sample collection region 112 of the sample handling device 110. Such interfacing structures can be configured for ease of use or to increase comfort while using the sample handling device 110. For example, one or more liners can be used to provide a better interfacing with the user's body with increased comfort during use of the sample handling device 110. In addition, the interfacing structures can be used to provide a seal between the sample handling device 110 and the user's body such that pressure generated by the sweat glands urges sweat through the flow channel 116.

In some embodiments, the sample collection region 112 can be defined by one or more portions of the sample handling device 110. For example, in some embodiments, the sample collection region 112 can be formed by assembling two or more portions or layers of structures to include an opening 122 for collection of bodily fluid, and to define a specific volume to temporarily hold the collected sample of bodily fluid. The two or more portions or layers can be selected or made such that once assembled the sample collection region 112 includes a suitable opening 122 and the body of the assembled portion of the sample handling device 110 defines a volume in the sample collection region 112 that can hold a suitable amount of collected bodily fluid. For example, the thickness of two or more portions can be selected to determine the volume or fluid capacity of the sample collection region 112. The two or more portions can be assembled using any suitable method such as friction fitting, gluing using adhesive material (e.g., a transfer adhesive), using fasteners, etc. In some other embodiments, the sample collection region 112 can be formed monolithically by a single integral portion or structure, to include an opening 122 suitably configured to collect a sample of bodily fluid, and to define a volume to hold the collected sample of bodily fluid.

The portions forming the sample handle device 110 and/or the sample collection region 112 can have a suitable flexibility to provide ease of being worn by a user, and to provide ease of access to the source of bodily fluid. For example, in some embodiments the portions or layers forming the sample handling device 110 and/or the sample collection region 112 can be of flexible nature such that the sample handling device 110 can be worn on the surface of skin of a user and the proximal portion of the sample collection region 112 can optimally interface with the skin of the user and conform to the contours of the user's body, even when the user is engaged in activity. In some embodiments, the sample handling device 110 and/or the sample collection region 112 can have a relatively rigid construction such that the rigidity allows better interfacing with the surface of the user's body and prevents the sample handling device 110 from getting malpositoned or dislodged from the user during intense activity. In some embodiments, one or more portions or components of the sample handling device 110 can be made rigid to achieve a locally rigid construction. The portions of locally rigid construction can be designed to avoid deformation of the sample analysis and/or test region 118. For example, the locally rigid portions can be configured such that the test region 118 does not deform by more than a few percent (e.g., 0-10%) under loads of about 1-10 Newtons. In some implementations, the sample handling device 110 can be configured such that the portions excluding the locally rigid portions of the device and/or the sample collection region 112 are generally flexible and conform to the skin and/or body of the user.

The opening 122 defined in the sample collection regions 112, shown in FIG. 2B, can be made accessible to a source of a sample of bodily fluid (e.g., skin containing sweat pores), and fluidically connected to the volume configured to temporarily contain the sample of bodily fluid collected from the source. The sample collection region 112 can be formed such that the volume and the opening 122 are defined in the body of the sample handling device 110, or a portion of the body of the sample handling device 110. In some embodiments, for example, the sample collection region 112 can be configured such that when the sample handling device 110 is positioned on the body of the user, the sample collection region 112 lies proximal to the surface of skin of the user and covers a suitable region of skin to collect a suitable volume of the bodily fluid such as sweat, over a suitable period of time. For example, as indicated in the schematic in FIG. 1, a section of human skin of a user can have a specific density of sweat pores that release sweat, each pore being spaced apart from the others at a specific distance. The sample collection region 112 can be configured such that the opening 122, when placed on the skin of the user, it can cover a certain area of skin containing a certain minimum number of sweat pores. Such a positioning can allow collection of an initial volume of sweat released from those pores over a desired period of time. In other words, the opening 122 can be sufficiently large to collect sweat from enough sweat glands to substantially fill the sample collection region 112 in a relatively short amount of time so the sweat can be analyzed shortly after the user starts perspiring.

In some embodiments, the SA system may require a minimum amount of bodily fluid for accurate testing and analysis. The opening 122 and/or the volume of the sample collection region 112 can be configured to determine the volume of bodily fluid collected in the initial sample, and to ensure that the collected initial sample satisfies the requirement of the minimum amount of fluid for accurate testing and analysis. In some implementations, the sample collection region 112 can include one or more structures (not shown in FIGS. 2A and 2B) configured to occupy and/or take up volume in the sample collection region 112 such that the volume of initial sample of bodily fluid to be collected and directed via the access port 114 can be smaller compared to the total volume defined by the sample collection region 112.

The space occupying structure(s) can be defined in the sample collection region 112, in any suitable manner. In some embodiments, the space occupying structure(s) can be solidly formed, for example using one or more spacer portions of spacer films to be assembled and/or deposited as material such as spacer ink (e.g., ink cured by uv light), or the like, on a surface of the sample collection region 112. For example, the space occupying structure can be included (e.g., deposited) on a layer or portion used to form a wall of the sample collection region 112. In some embodiments, the space occupying structures can be implemented by one or more spacer layers or portions assembled with one or more other portions to form the sample collection region 112. In some embodiments, the space occupying structure(s) can include an outer covering defining a hollow within and/or encapsulating a volume defined within the outer covering. In some embodiments, an outer covering of the space occupying structures can be molded and/or contoured to define a space that can be excluded or isolated from the volume defined by the sample collection region 112.

In some embodiments, the volume of the initial sample may also determine the ease of collection, direction of fluid flow to be tested, and expulsion, thereby determining the rate at which samples can be collected and tested or analyzed. Said in another way, in some embodiments of the sample handling device 110, an initial sample of bodily fluid (e.g., sweat) can be collected, the volume of the initial sample being determined by the volume of the sample collection region 112. The collected initial sample can be directed though the access port 114 into a flow channel 116 to be tested and expelled, in a continuous flow of bodily fluid, making room for continuous collection of bodily fluid subsequently secreted by the user during use. The processes of sample collection, sample testing and sample expulsion can be carried out in a continuous manner, with a continuous flow of collected bodily sample though the collection region 112, the access port 114, the flow channel 116, and the test region(s) 118, at a suitable rate. In such embodiments, the volume of the sample collection region 112 and the size of opening 122 defined in the sample collection region 112 can determine the rate at which the initial amount of sample is collected. The volume of the sample collection region 112 and the size of opening 122 can partially determine the linear flow rate (i.e., the volumetric flow rate divided by the cross section area of the flow channel 116) at which the sample is directed through the access port 114, the flow channel 116, and the test region(s) 118 before being expelled.

In some embodiments, as an example, the sample collection region 112 can have a volume and/or fluid capacity between about 0.01 milliliters (mL) and about 5.0 mL. In some embodiments, the sample collection region 112 can have a fluid capacity between about 0.02 mL and about 1 mL, between about 0.03 mL and about 0.5 mL, between about 0.04 mL and about 0.3 mL, between about 0.06 mL and about 0.1 mL inclusive of all ranges or subranges therebetween. In some embodiments, the sample collection region 112 can have a volume sufficient to house an initial amount of sample measured in volumes as small as a microliter or less of bodily fluid (e.g., a volume as small as 20 drops of bodily fluid, 10 drops of bodily fluid, 5 drops of bodily fluid, a single drop of bodily fluid, or any suitable volume therebetween). In other embodiments, the sample collection region 112 can have a volume up to, for example, about 5.0 mL, 10.0 mL, 15 mL, or more. In some embodiments, the sample collection region 112 can have a fluid capacity based on the volume defined by one or more space occupying structures and/or based on the volume isolated and/or removed by the space occupying structures, as described previously.

As shown in FIGS. 2A and 2B, the access port 114 of the sample handling device 110 is fluidically coupled to the sample collection region 112. The access port 114 can be an opening, a through hole, a conduit, a fluid flow path or the like, defined in the body of the sample handling device 110, to fluidically connect the sample collection region 112 to the flow channel 116, described in further detail below. In some embodiments, the sample collection region 112 can be formed by assembling two or more portions or structures, as described herein. In some embodiments, one of the portions can be configured to include and/or define the opening 122, while another portion can be configured to include and/or define the access port 114. One or more of the portions that are assembled can be configured to form, upon assembly, one or more walls of the sample collection region 112. In embodiments where the sample collection region 112 is defined in a monolithic structure, the access port 114 can be an orifice, a conduit and/or a flow path defined in the body of the sample handling device 110 to fluidically couple the sample collection region 112 with the flow channel 116.

The access port 114 can be situated at any suitable location with respect to the sample collection region 112 to mediate a fluidic connection between the sample collection region 112 and the flow channel 116. For example, in some embodiments the access port 112 can be an orifice defined on an inner surface of the sample collection region 112. In some embodiments, the access port 114 can be defined on a distal portion of the sample collection region 112 (i.e., away from the body of a user when the sample handling device 110 is in use). In some embodiments, for example, the access port 114 can be defined at a central portion with respect to the opening 122 and/or a volume defined by one or more walls of the sample collection region 112 to hold the collected bodily fluid. In some other embodiments, for example, the access port 114 can be defined in an off-center location with respect to the opening 122 and/or the volume defined by the walls of the sample collection region 112 to hold the collected bodily fluid. In some embodiments, the access port 114 can belocated in any suitable position with respect to the sample collection region 112, the opening 122, and/or the flow channel 116 in order to prevent and/or flush formation of bubbles in the collected sample of bodily fluid. In some embodiments, the access port 114 can be situated at a position such that the sample collection region 112 is suitable formed to direct flow of fluid towards the access port 114, for example via a narrowing, conduit, contouring of one or more structures, and/or the like.

The access port 114 can be of any suitable size to allow transport of the collected sample of bodily fluid out of the sample collection region 112 to other portions of the sample handling device 110 (e.g., the test region(s) 118, etc.). In embodiments, the size of the access port 114 can be in the range of few hundred microns to few millimeters. For example, the access port 114 can have an internal, cross-sectional diameter between about 0.05 millimeters (mm) and about 5.0 millimeters (mm). In some embodiments, the access port 114 can have a cross-sectional area sufficient to permit continuous flow of collected sample of bodily fluid to the flow channel 116.

In some embodiments, the access port 114 can be configured to allow continuous flow of the collected sample of bodily fluid once the initial sample of the bodily fluid reaches a minimum amount in volume. In some embodiments, the access port 114 can be configured such that it permits a continuous flow of collected bodily fluid after the sample collection region 112 reaches a minimum amount of positive pressure from the collection of a substantial or minimum volume of bodily fluid (e.g., a volume as small as 20 drops of bodily fluid, 10 drops of bodily fluid, 5 drops of bodily fluid, a single drop of bodily fluid, 20 µL, 15 µL, 10 µL, 5 µL, or any suitable volume therebetween).

The access port 114 can determine the rate of flow of collected bodily fluid to be tested using the SA system with the sample handling device 110. In some embodiments, the access port 114 can have wicking properties to draw the collected fluid sample from the sample collection region 112 into the flow channel 116. In some embodiments, the collected sample in the sample collection region 112 can be directed into the access port 114 and beyond by a pressure differential. For example, a lower pressure in the access port 114 and the flow channel 116 compared to the sample collection region 112 can draw the collected sample of bodily fluid through the access port 114 and the flow channel 116. Similarly, as the sample collection region 112 is increasingly filled with the collected bodily fluid, the increase in the pressure in the sample collection region 112 (i.e., generated by the sweat glands) can urge the collected sample of bodily fluid through the access port 114 into the flow channel 116. Said another way, the seal between the sample handling device 110 and the user's body is sufficiently fluid-tight such that pressure generated by the sweat glands urges sweat through the flow channel 116. In some other embodiments, the access port 114 can be configured such that the fluid in the sample collection region 112 is drawn out via capillary action.

The flow channel 116 can be of any suitable width, height, diameter, or cross-sectional area to receive the collected sample of bodily fluid from the sample collection region 112 via the access port 114 and to suitably transport the sample of bodily fluid to other parts of the sample handling device 110 such as the test region(s) 118. For example, the flow channel 116 can have a circular cross-section with a suitable diameter, or a rectangular cross-section with a suitable width and height of the flow channel 116. The width, height, or diameter of the flow channel 116 can be in the range of few hundred microns to few millimeters. For example, the width, height, and/or diameter of one or more portions of the flow channel 116 can be between about 0.05 millimeters (mm) and about 5.0 mm. The flow channel 116 can extend for any suitable length, from few millimeters to few centimeters, and be configured to assume any suitable shape along the length. For example, the flow channel 116 can extend over a length between 5 millimeters (mm) and about 15.0 centimeters (cm). The flow channel 116 can be configured to follow any suitable path such as a linear, rectilinear, curvilinear, or a serpentine path.

In some embodiments, the flow channel 116 can be defined within an integral structure built monolithically such that the diameter of the flow channel 116 is determined at least partially by the thickness of the monolithic structure defining the flow channel 116. In some other embodiments, the flow channel 116 can be constructed by assembling two or more portions or layers of structures, collectively defining the flow channel 116. In some embodiments, the flow channel 116 can be formed by several layers or portions assembled together to direct flow of fluid via one or more channels, though holes, apertures, and/or the like. The flow channel 116 can be configured such that external influences during use such as forces arising from gravity, movement of a user's body, and the like, do not interfere with flow of fluid within the flow channel 116, and/or do not significantly change the physical shape or dimensions of the flow channel 116 when in use.

In some embodiments, the flow channel 116 can include various portions suitably configured to direct flow of bodily fluid with a suitable rate of flow or volume of flow. For example, in some embodiments, the flow channel 116 can include portions that are configured with different cross-sectional shape and/or size. For example, some portions of the flow channel 116 can be circular or rectangular while other portions are not. Similarly, some portions of the flow channel 116 can have a narrower or broader cross-sectional area compared to other portions of the flow channel 116. In some embodiments, the flow channel 116 can include an inflow portion and an outflow portion. The inflow portion of the flow channel 116 can be configured to transport bodily fluid collected in the sample collection region 112 to the test region(s) 118 described below via the access port 114. The outflow portion of the flow channel 116 can be configured to remove the sample of the bodily fluid, after testing at the test region(s) 118, to be expelled out of the sample handling device 110, for example to the environment. For example, in some embodiments, the flow path 116 can be configured to be linear at some portions defined by the one or more test regions 118 and the outflow portion of the flow channel 116 can include a tortuous vent path to reduce and/or avoid air ingress. In some embodiments, the tortuous path can be configured to reduce and/or avoid undesired fluid/air flow due to gravity, acceleration, user motion, etc.

The inflow and outflow portions of the flow channel 116 can be suitably shaped to allow for optimal flow of the sample of bodily fluid, for optimal access to the sample of bodily fluid for testing, and for optimal expulsion of the sample after testing. In some embodiments, portions of the flow channel 116 may also include structural and/or functional adaptations to overcome or allow tolerance to physical forces such as stress and/or strain that may be encountered when the sample handling device 110 is used when the user engages in intense activity. For example, in some embodiments, the flow channel 116 can be configured to include suitable linear, angular and/or curved portions or serpentine portions to better tolerate different types of physical forces, including stress and/or strain encountered when the sample handling device 110 worn by a user during high-intensity or contact sport activities. In some embodiments, the flow channel 116 may be configured to include one or more curved portions or serpentine portions to acts as localized traps to prevent air from outside the sample handling device 110 to enter the flow channel 116.

As indicated in the schematic in FIG. 2B, the flow channel 116 can include an outlet 124 to expel the collected and tested sample of bodily fluid. In some embodiments, the sample of bodily fluid can be directed through the outflow portion of the flow channel 116 and via the outlet 124 by virtue of a sequence of pressure differentials. In some other embodiments, the sample of bodily fluid, after testing at the test region(s) 118, can be directed towards the outlet 124 by one or more suitable physical forces. For example, the sample of bodily fluid can be expelled via the outlet 124 by gravitational force, capillary action, motion of the user and/or the like.

As shown in FIGS. 2A and 2B, the sample handling device 110 incudes the test region(s) 118. The test region(s) 118 can includes any suitable number of test regions defined along the flow channel 116. For example, in some implementations, the sample handling device 110 can include two, three, or more test regions defined at specified portions of the flow channel 116 such that bodily fluid collected at the sample collection region 112 can be directed via the access port 114 and through one or more of the test regions for sequential or parallel processing, as described herein. In some embodiments, the test region(s) 118 can be separated from but fluidically coupled to the flow channel 116. In some embodiments, the test region(s) 118 can be defined as a portion of the flow channel 116. For example, the flow channel 116 can include the inflow portion and the outflow portion separated by the test region(s) 118 being a third portion. The test region(s) 118 can be configured to intersect with the flow of the bodily fluid in the flow channel 116. In some embodiments, the test region(s) 118 can be configured to define a volume sufficient to hold a portion of the sample of bodily fluid while being tested.

The test region(s) 118 of the sample handling device 110 can include a set of sample ends of a set of electrodes 120 configured to interface with the sample of bodily fluid flowing through the test region(s) 118. The set of electrodes 120 can include any suitable number of electrodes and the sample end of each electrode can be configured either to deliver an excitation signal to the sample of bodily fluid to be tested (e.g., as a current delivery electrodes), or to sense a response signal from the sample of bodily fluid tested with the excitation signal (e.g., as a voltage sensing electrode). In some embodiments, the electrodes 120 can include electrodes configured to supply power to one or more components included in the sample handling device 110 (e.g., one or more sensors such as temperature sensors, etc.) and/or to carry signals from the one or more components to a sample processing device (e.g., signals reporting temperature measurements by a temperature sensor). The number of electrodes can be suitably optimized in different embodiments of the sample handling device in consideration of parameters such as number of electrodes required for effective delivery of the excitation signal, number of electrodes required for a predetermined signal-to-noise ratio in the response signal obtained from the tested sample of bodily fluid, number of electrodes suitable to meet a predetermined form factor or structural and/or functional limitation, and/or the like. For example, in some embodiments the set of electrodes can include four electrodes, two of which are configured to deliver the excitation signal in the form of a test current signal, and two of which are allocated to record the response voltage from the sample of bodily fluid after applying the test current signal. As an example, the electrodes 120 can be configured as a four-pole impedance cell. As another example, in some other embodiments, the set of electrodes can include two electrodes, one configured to deliver the excitation signal and the other configured to read the voltage from and/or current passing through the sample of bodily fluid being tested. For example, the electrodes 120 can be configured as a bipolar impedance cell.

The set of electrodes can have a test end at the test region(s) 118, configured to interact with the sample of bodily fluid in the test region(s) 118. The set of electrodes can include excitation electrodes and sensing electrodes. In some embodiments, each electrode of the set of electrodes 120 can be configured to serve as either an excitation electrode or a sensing electrode. In some embodiments, the set of electrodes 120 can include excitation electrodes, designated to deliver excitation signals to a portion of a sample of bodily fluid at a test region(s) 118, and sensing electrodes designated to sense a response signal from the sample of bodily fluid in response to an application of an excitation signal. The set of electrodes can include a terminal end (not shown) configured to interact with a portion of a sample processing device described herein and a sample end configured to interact with a portion of sample fluid at one or more test regions 118. In some embodiments, for example, an excitation electrode can be configured to receive, at a terminal end, an excitation signal from a source of electrical power and deliver, at the sample end, the excitation signal to the portion of the sample of bodily fluid directed with the flow channel and at the test regions 118. As another example. A sensing electrode can be configured to receive at a sample end interfacing with a portion of a sample of bodily fluid at the test regions 118, a response signal emitted from the sample portion of bodily fluid at the test regions 118 and deliver the received response signal to a terminal end interfaced with a portion of a sample processing device such that the response signal can be suitable processed and/or analyzed by a processor, and/or stored in a memory, associated with the sample processing device. In some embodiments, the sample processing device can be configured to receive response signals from electrodes 120 associated with two or more test regions 118 such that the response signal from each of the two or more test regions 118 can be compared to determine properties of the sample bodily fluid.

In some instances, a distance between the electrodes 118 associated with the two or more test regions 118 can be used in the determination of properties of the sample bodily fluid. For example, an impedance associated with the response signal from each test region 118 can be used to assess a rate of flow and/or a rate of volumetric flow of the sample bodily fluid. In some implementations, a known geometry of the flow path connecting the test region(s) 118 can be used to calculate the volumetric flow rate.

From the rate of volumetric flow of the sample bodily fluid a rate of secretion of the sample bodily fluid (e.g., a rate a perspiration of sweat) can be estimated or extrapolated. In some implementations, known attributes of the user (height, weight, etc.) can be used to calculate a rate of perspiration of the user. In some implementations, the rate of perspiration can be used to estimate a cumulative fluid loss over time and/or a cumulative electrolyte loss over time.

In some embodiments, the excitation signal can be a test current signal. In some embodiments, the electrodes 120 are configured such that the test current signal is in the form of direct current. In some embodiments, the electrodes are configured such that the applied test current signal is in the form of alternating current (AC). In the embodiments using alternating current, the electrodes 120 can be configured such that the alternating polarity of the test current signal experienced by the electrodes allows for partial reversal of the impact of the salinity of the sample of bodily fluid on the electrodes. Thus, the use of AC for excitation can aid in prevention of rapid corrosion and/or ionization of the electrical interface of the electrodes in the test region which may have otherwise been the result of a direct current excitation signal. In some embodiments, one or more of the electrodes 120 can have a coating with one or more suitable materials (e.g., carbon) to reduce corrosive effects of the bodily fluids being tested. In some embodiments, the electrodes may be capacitively or AC coupled to the electronics such that no DC can flow through the sample, reducing the risk of corrosion or ionization.

In some embodiments, the electrodes 120 can be configured to detect a presence of one or more ions in the sample of bodily fluid. For example, in some embodiments, the electrodes 120 can be configured to detect the presence and/or quantify the amount of one or more of $Na^+$, $Cl^-$, $Ca^{2+}$, $K^+$, or $Mg^{2+}$ ions in the portion of the initial volume of bodily fluid.

While described with reference to detect presence of ions, the systems, devices, and methods described herein can be equally suited and/or used to detect and/or quantify a presence of analytes in a sample of bodily fluid. For example, the presence of lactose, glucose, etc., can be detected and/or quantified.

In some embodiments, the sample handling device 110 can optionally include one or more temperature sensors 140. The temperature sensors 140 can be suitably located at or near the one or more test regions 118 and configured such that the temperature sensors 140 can record the temperature of the samples of bodily fluid being tested at the one or more test regions 118. In some implementations, the temperature sensors 140 can be positioned to monitor and measure the temperature of the sample of bodily fluid during testing in one or more test regions 118. The temperature sensor 140 can be any suitable temperature sensing device that can be suitably positioned adjacent to in suitable proximity to a test region 118 and used to measure a temperature of a sample of a bodily fluid. For example, the temperature sensor 140 can be a thermistor or a thermistor assembly. In some embodiments, the sample handling device 110 can include additional sensors (not shown) to record ambient conditions. For example, the sample handling device 110 can include temperature sensors to measure a temperature of a skin of a user and/or ambient air temperature. In some embodiments, the sample handling device 110, and/or the sample processing device coupled to it, can include any number of additional sensors to sense pressure, humidity, etc. In some implementations, the temperature sensor 140 can be used to calculate a temperature of the sample of bodily fluid from which an estimate of core body temperature of the user can be calculated. In some implementations, the core body temperature can be used to estimate a rate of loss and/or cumulative loss of hydration and/or electrolytes of the user and/or estimate the effects of the loss of hydration and/or electrolytes.

In use, the sample handling device 110 is positioned on the surface of the body of a user to collect and direct bodily fluid for testing and analysis, to determine a state of the user's health. For example, the sample handling device 110 can be positioned on an arm of an athlete engaged in a sporting event to collect and test the user's sweat and analyze the collected sweat for its salinity from which the user's state of hydration, electrolyte losses, and perspiration rate can be determined. The sweat is collected in the sample collection region 112 of the sample handling device 110 and continuously directed through the access port 114 to the flow channel 116. In some instances, a spacer portion included in the sample collection region 112 can occupy space within the sample collection region 112 and reduce the amount of sample of bodily fluid required to be collected to urge or start the flow of bodily fluid via the flow channel 116. Portions of the flow channel 116 are configured to direct the collected sweat, at a continuous rate of flow, to the test region(s) 118 where the sweat interacts with the set of electrodes 120. An excitation or test current signal is delivered to the sample sweat in the test region(s) 118, via one or more electrodes (current delivery electrodes) from the set of electrodes 120. The response voltage generated by the sweat sample in response to the excitation or test current signal is read by one or more electrodes (voltage sensing electrodes, different from the current delivery electrodes), from the set of electrodes 120. In some instances, the excitation or test current signal can be delivered and the response voltage can be read in a continuous manner. The voltage read from the sweat sample is used to compute an impedance associated with the sweat sample, and the impedance can be correlated with a quantification or measure of salinity of the sweat as well as other physiological information of the user. Thus, the sweat of the user can be continuously tested over a period of time and the measure of salinity of the user's sweat can be correlated to a continuous measure of degree of hydration electrolyte losses, and perspiration rate of the user over the period of time while the user is engaged in an activity.

An example Sample Analysis System

Figure 3:
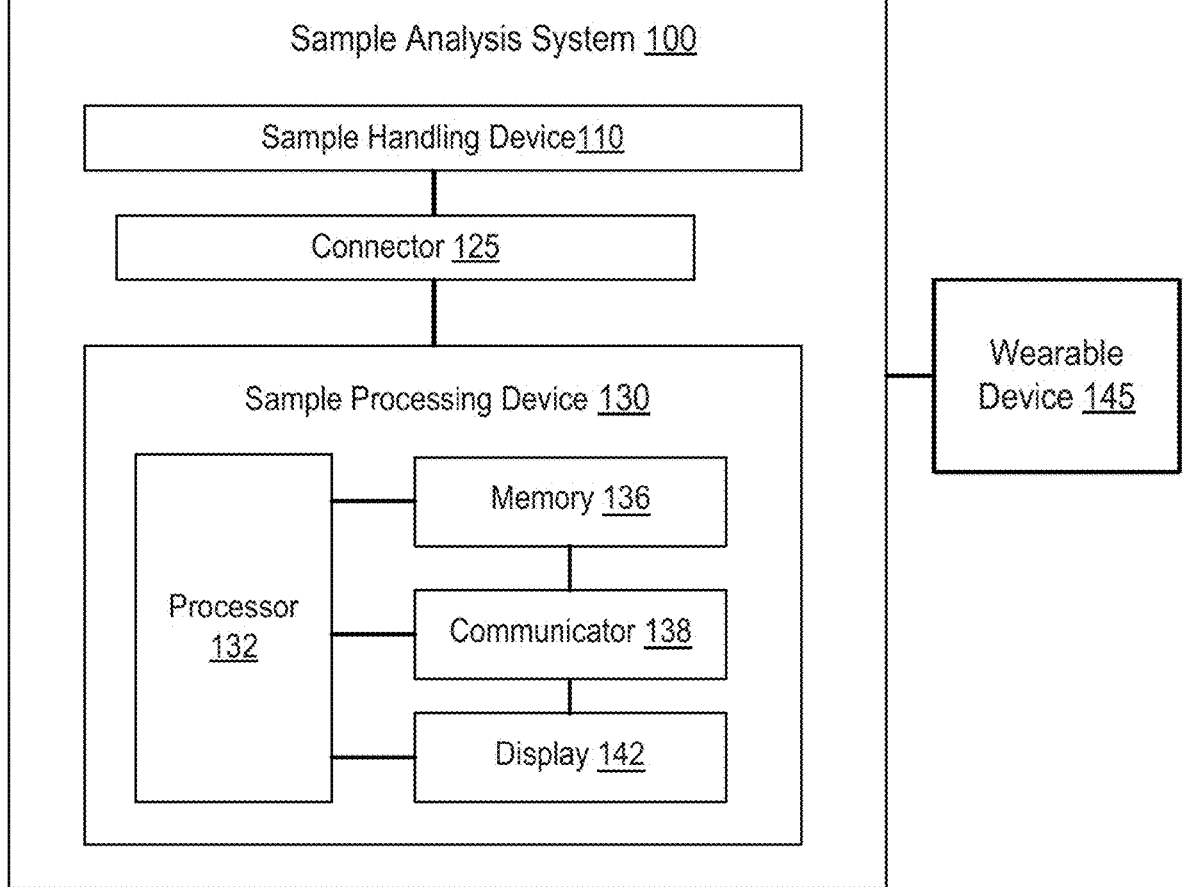
FIG. 3 is a schematic illustration of an example Sample Analysis System ("SA system") including the sample handling device of FIGS. 2A, 2B, according to an embodiment.

FIG. 3 is a schematic illustration of a Sample Analysis system 100, according to an embodiment. The SA system includes the sample handling device 110 as described above, and a sample processing device 130, coupled to each other via a connector 125. In some embodiments, the connector 125 can be permanently connected or removable from the sample handling device 110 and/or the sample processing device 130. In some instances, the sample analysis system 100 can be configured to be integrated in, to, or with a wearable device 145 (e.g., a watch, odometer, activity tracker, heart rate monitor, etc.). While the SA system 100 is illustrated in FIG. 3 to include a sample processing device 130 and be coupled to a wearable device 145, in some instances, the sample handling device 110 can be directly integrated with a wearable device 145 without requiring the sample processing device 130.

The connector 125 can be a mechanical connector defined on the sample processing device 130, configured to engage with portions of the sample handling device 110, such that the sample handling device 110 can be mounted on the sample processing device 130 before being worn by the user. In some embodiments, the sample processing device 130 can be configured to a durable multi-use device and the sample handling device 110 can be configured to be a single-use device that can be mounted and/or connected to the sample processing device for a period of use (e.g., an activity period) and discarded to be replaced by another sample handling device 110. The connector 125 can be configured such that it allows ease of removal and replacement of a sample handling device 110. In addition to a physical connection, the connector 125 can include a set of suitable electrical connections to electrically couple the sample handling device 110 to the sample processing device 130. For example, the connectors can be in the form of pogo pins and/or flexible contacts that can be engaged to provide an electrical connection upon the sample handling device 110 being mechanically coupled to the sample processing device 130, for example using a snap ring interface.

The sample processing device 130 can be of a suitable form factor to be easily worn by a user when engaging in intense bouts of activity such that the sample handling device 110 can be appropriately interfaced with the body of the user (e.g., a portion of skin of the user). The sample processing device 130 can include a processor 132, a memory 136, a communicator 138, and a display 142.

The processor 132 can be, for example, a hardware based integrated circuit (IC) or any other suitable processing device configured to run and/or execute a set of instructions or code. For example, the processor 132 can be a general purpose processor, a central processing unit (CPU), a micro-controller, an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 132 is operatively coupled to the memory 136 through a system bus (for example, address bus, data bus and/or control bus). The processor 132 can be configured to perform a set of functions to near-instantaneously or in real-time test, measure and analyze properties of the sample bodily fluid collected by the sample handling device. For example the processor 132 can be configured to generate a set of excitation signals to probe the sample of bodily fluid, to provide instructions on delivery of the excitation signals via the electrodes in the sample handling device 110, to receive the response signals obtained from the sample of bodily fluid read by the electrodes in the sample handling device 110, and to interpret the response signals to determine properties of the sample bodily fluid and by extension indicate a state of the user's health. In some embodiments, the processor 132 can also be configured to perform additional functions such as indicate to the user via a display 142 (e.g., a graphical display) relevant information regarding the properties of the sample bodily fluid analyzed and/or a state of the user at the time of testing. The processor 132 may also be configured in some embodiments to transmit a set of signals, interpretations, and/or results of analyses to remote compute devices for further processing, as described herein.

The memory 136 of the sample processing device 130 can be, for example, a random access memory (RAM), a memory buffer, a portable hard drive, a read-only memory (ROM), an erasable programmable read-only memory (EPROM), and/or the like. The memory 136 can store, for example, user date for later use/analysis and/or one or more software modules and/or code that can include instructions to cause the processor 132 to perform one or more processes, functions, and/or the like (e.g., the generation of excitation signals, delivery of test signals, reading and analyses of response signals, etc.) described herein. In some implementations, the memory 136 can be a portable memory (for example, a flash drive, a portable hard disk, and/or the like) that can be operatively coupled to the processor 132. In other instances, at least a portion of the memory can be remotely operatively coupled with the sample processing device 130. For example, a remote database server can be operatively coupled to the sample analysis system 100 via the sample processing device 130.

The communicator 138 can be a hardware device operatively coupled to the processor 132 and memory 136 and/or software stored in the memory 136 executed by the processor 132. The communicator 138 can be, for example, a compact network interface card (NIC), a Wi-Fi module, a Bluetooth® module, a radio frequency communication module, and/or any other suitable wired and/or wireless communication device. Furthermore, the communicator can include a switch, a router, a hub and/or any other network device. The communicator 138 can be configured to connect the sample processing device 130 to a communication network or one or more compute devices. In some instances, the communicator 138 can facilitate receiving and/or transmitting a file and/or a set of files through a communication network to the one or more compute devices (e.g., computers, smart phones, remote databases, servers, etc.).

The display 142 can be a low power module configured to indicate one or more results from the analyses of the samples of bodily fluid collected and tested by the sample analysis system 100. For example, the display 142 can be configured to have a set of backlit icons indicating a state of hydration of the user, or an indication for increased hydration of a user, or the like. In some embodiments, the display 142 can also be configured to include a status indicator related to the sample processing device 130 or the sample handling device 110. For example, the display 142 can be configured to alert the user that a sample handling device 110 needs to be changed or that a sample processing device 130 needs to be charged with power. For example, the sample processing device 130 can be configured to be powered by a disposable or re-chargeable battery power supply unit. In embodiments that include rechargeable power supply, the sample processing device 130 can include adaptations for re-charging the power supply unit when plugged to a power outlet. In some embodiments, the sample processing device 130 can include devices to indicate a state of charge.

Figure 4:
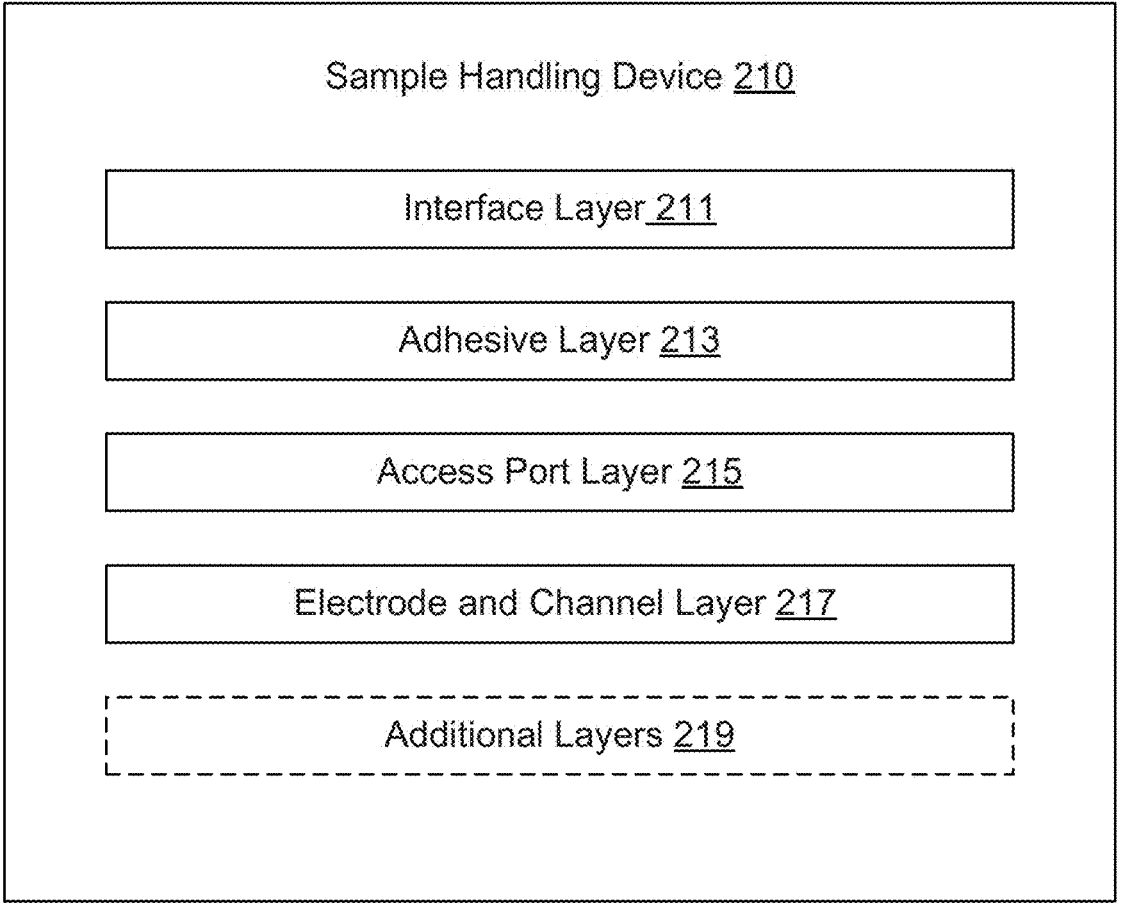
FIG. 4 is a schematic illustration of structural components of a sample handling device, according to one embodiment.

FIG. 4 illustrates and example construction of a sample handling device 210, according to an embodiment. The sample handling device 210 can be substantially similar in form and/or function to the sample handling device 110 described above with reference to FIGS. 2A and 2B. For example, the sample handling device 210 can include a sample collection region, an access port, a flow channel, a test region, and a set of electrodes, as described with reference to the sample handling device 110. Accordingly, such similar portions and/or aspects are not described in further detail herein.

As described above with reference to the sample handling device 110, one method of constructing the sample handling device 210 includes the assembly of specifically shaped elements or portions or layers in specific configurations to form the various components or elements of the sample handling device 210. FIG. 4 illustrates one example set of structural layers that can be used to assemble the sample handling device 210 described herein. The layers of the sample handling device 210 can be made of a suitable material to confirm to requirements of the sample handling device 210 during use. For example, one or more of the layers can be rigid, w % bile one or more can be flexible. The layers can be made of biocompatible material (e.g., biocompatible polymers). In some embodiments, the layers can be made from cutting sheets of the suitable material to confirm to specific shapes including specific features.

As shown in FIG. 4, the sample handling device 210, can be in the form of a patch constructed from a set of layers including an interface layer 211, an adhesive layer 213, an access port layer 215, and an electrode and channel layer 217 (either a single layer or two discrete layers). In some embodiments, the sample handling device 210 can include additional layers 219 to provide interfacing advantages with the user or with a sample processing device, or to provide additional support during use of the sample handling device 210, or the like. In some embodiments, the sample handling device 210 can be configured to be a single use device used with a suitably compatible durable, multi-use, sample processing device, as described previously.

The interface layer 211 can be a liner layer (e.g., release liner) with one or more adhesive portions on the proximal side and/or the distal side. The interface layer 211 can be configured to be placed on the surface of a user's body with the proximal side facing the user's body. In some embodiments, the adhesive properties of the proximal side can be used to affix the sample handling device 210 onto the user's body. In some embodiments, the adhesive properties of the distal side of the interface layer can be used to affix the interface layer 211 to the subsequent layer, the adhesive layer 213, in the assembly of layers to form the sample handling device 210. In some embodiments, the interface layer 211 can include adaptations to allow a user to manipulate the sample handling device 210 while mounting the sample handling device 210 onto a sample processing device or on a user. For example, the interface layer 211 can include a tab protruding or extending beyond the contours of the other layers of the sample handling device 210 that can be used to hold the sample handling device 210.

The adhesive layer 213 is configured to be positioned or assembled on the interface layer 211 and to have adhesive properties on its proximal and/or distal side. The adhesive layer 213 can be assembled on the interface layer 211 using the adhesive properties of the distal side. The adhesive layer 213 is configured to form the opening and the boundary walls of the sample collection region of the sample handling device 210. The adhesive layer 213 can include and/or define an opening of a suitable size that corresponds to the opening of the sample collection region of the sample handling device 210. The opening in the adhesive layer can be a portion cut out from the adhesive layer and devoid of any adhesive properties (e.g., a centrally located cut-out portion). The thickness of the adhesive layer 213 can form the boundary walls of the sample collection region and determine the volume or fluid capacity of the sample collection region of the sample handling device 210. For example, the thickness of the adhesive layer 213 can be selected such that the opening defined in the adhesive layer 213 and the thickness of the opening together define a volume or space where a sample of bodily fluid can be collected forming the sample collection region. While FIG. 4 indicates a single adhesive layer 213, in some embodiments, two of more adhesive layers can be assembled to collectively form the sample collection region with the collective thickness of all the adhesive layers. The adhesive properties of the distal side of the adhesive layer 213 (facing away from the user's body) can be used to affix the adhesive layer 213 to the subsequent layer, the access port layer 215, in the assembly of the sample handling device 210.

The access port layer 215 can have adhesive properties on its proximal side facing the adhesive layer 213 that can be used to assemble the access port layer 215 on the adhesive layer 213. The portion of the access port layer 215 adjacent to the cut out portion of the adhesive layer 215 forms a base or wall portion of the sample collection region defined by the opening and thickness of the adhesive layer 213. The access port layer 215 includes an opening defined in the base or wall portion of the sample collection region to serve as an access port of the sample handling device 210. The opening in the access port layer 215 can be positioned in any suitable location such that it provides access to the sample collection region. The opening forming the access port of the sample handling device 210 can be of a suitable size to form a conduit through the access port layer 215 and to fluidically connect the sample collection region to the other or proximal side of the access port layer for the flow of the collected sample of bodily fluid. The thickness of the access port layer 215 can determine the length of the conduit defined by the access port. In some embodiments, the access port layer 215 can be made of a flexible material such as polyethylene terephthalate (PET) of suitable thickness, for example 3 mil PET. In some embodiments, any suitable material such as polydimethylsiloxane (PET), silicon, polyurethane, glass, or any other suitable material can be used to form one or more layers of the sample handling device 210. In some embodiments, the material may be selected based on one or more properties such as stiffness, conformability, thickness, thinness, transparency, receptivity to interfacing with various adhesives, receptivity to screen-printing one or more conductive traces, (e.g., using conductive ink to form electrodes), etc.

The electrode and channel layer 217 includes a proximal side and a distal side that can each include portions of the surfaces having adhesive properties to aid in assembly of the sample handling device 210. The proximal side of the electrode layer can include and/or define a flow channel while the distal side of the electrode and channel layer 217 includes a set of electrodes. The electrode and channel layer 217 can be configured to form the flow channel in the proximal side by defining one or more trenches in the thickness of the electrode and channel layer 217 such that upon assembly on the access port layer 215 the depth of the trenches determine the cross-sectional area of the flow channel of the sample handling device 210. The remaining portion of the proximal side of the electrode and channel layer 217 that is in contact with the access port layer 215 can have adhesive properties to be affixed to the distal side of the access port layer 215. In such a configuration, the flow channel is formed such that a portion of the wall of the flow channel along the length is formed by the trench defined in the electrode and channel layer 217 while the other portion of the wall of the flow channel is formed by the distal side of the access port layer 215. The flow channel can be formed to include a test region.

The distal side of the electrode and channel layer 217 can include conducting portions made of etched, printed, coated or applied conductive ink to form a set of electrodes. For example, the electrodes can be formed by printing an ink that includes 80% silver and 20% silver chloride. The set of electrodes can include excitation or test current signal delivery electrodes and voltage sensing electrodes. The electrode layer 217 include non-conducting portions surrounding the electrode portions to form defined paths or traces for the electrodes. In some instances, the proximal side of the portions of the electrode and channel layer 217 that contain the electrodes in the distal side can be coated or applied with dielectric material to protect the electrode traces in the distal side. The electrodes include test ends situated adjacent to or in the path of the flow channel, at the test region, allowing access to a portion of the sample bodily fluid that may flow through the flow channel. In other embodiments, another type of material could be chosen for the electrode ink depending on the sensing methodology.

In use, some embodiments of the sample handling device 210, similar to the sample handling device 110, can be configured to continuously collect sweat from a small area of sweat glands on the skin of a user, in a sample collection region and direct the collected sweat for testing at a suitable rate of flow. The collected sweat can be continuously directed through the access port via the flow channel to the test region and across a set of conductive electrodes in the test region. At the test region, an excitation signal is applied via one set of electrodes (e.g., current delivery electrodes) and the response is read by a set of electrodes (e.g., the voltage sensing electrodes). The resultant impedance reading is taken using the sensed voltage and correlated with a measure of salinity of the collected sweat. After passing over the electrodes, the sweat is continuously directed further through the outflow portion of the flow channel and expelled to the environment, at a suitable rate of flow. This allows for continuous readings of measures of salinity of the user's sweat, which can be used to infer a degree of hydration of the user during an intensive bout of activity. The sample handling device 210 can be applied to any part of the body large enough to fit the size of the device 210.

The sample handling device 210 can be connected to a reusable electronic sample processing device via a mechanical connector. This allows the sample handling device 210 to be disconnected and disposed of while retaining the durable electronic sample processing device to be used with a different sample handling device 210 in the future. The mechanical connection also allows for an electrical connection between the durable electronics and the patch with features to prevent sweat from contaminating the electrical connection between the components. The durable electronic sample processing device can be powered via disposable or rechargeable battery cells, as described previously. The durable sample processing device has a simple means of display and communication via either LEDs or a small screen. The durable electronic sample processing device may also have the ability to wirelessly communicate with a smartphone or base station which allows real time monitoring of more than one user (e.g., athletes at an event, or in a sports team, etc.).

Figure 5A:
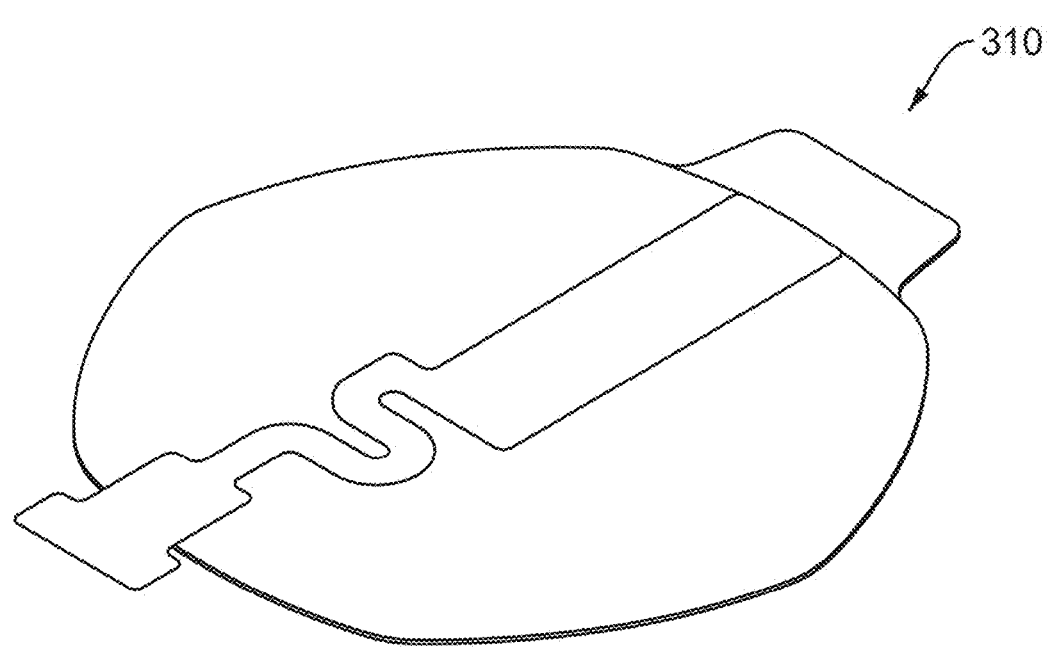
FIG. 5A is a schematic illustration of a perspective view of an example sample handling device, according to an embodiment.
Figure 5B:
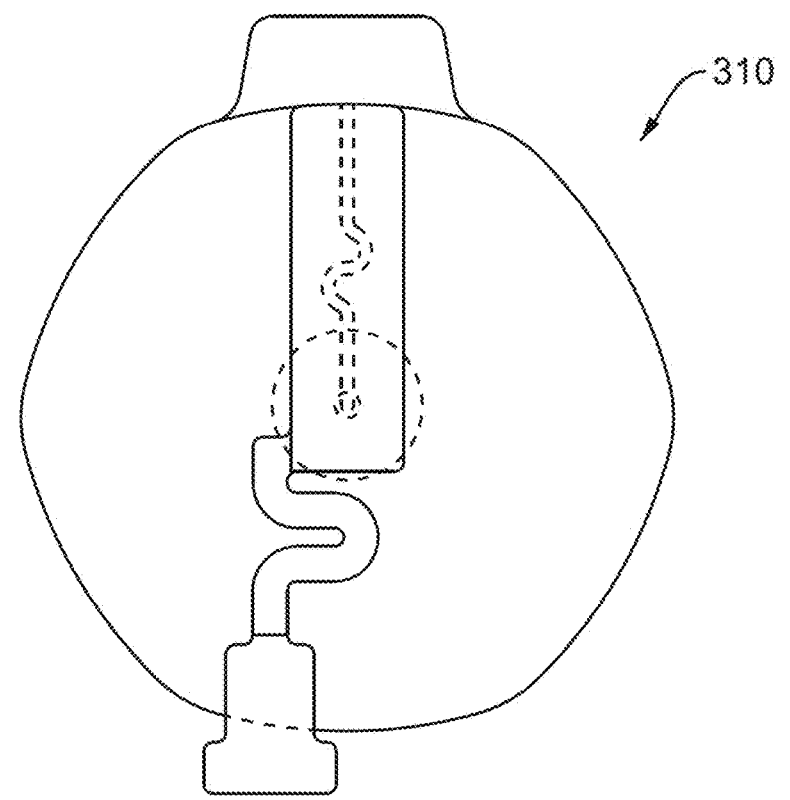
FIG. 5B is a schematic illustration of a top view of the example sample handling device in FIG. 3A.

FIGS. 5A and 5B illustrate an example sample handling device 310, according to an embodiment. The sample handling device 310 can be substantially similar in form and/or function to the sample handling devices 110 and 210 described above with reference to FIGS. 2A-2B, and 4 respectively. For example, the sample handling device 310 can include a sample collection region, an access port, a flow channel, a test region, and a set of electrodes, as described with reference to the sample handling device 110. The sample handling device 310 can be constructed similar to the sample handling device 210 such that it includes an interface layer 311, an adhesive layer 313, an access port layer 315, and an electrode and channel layer 317, as described with reference to the sample handling device 210. Accordingly, such similar portions and/or aspects are not described in further detail herein.

Figure 6:
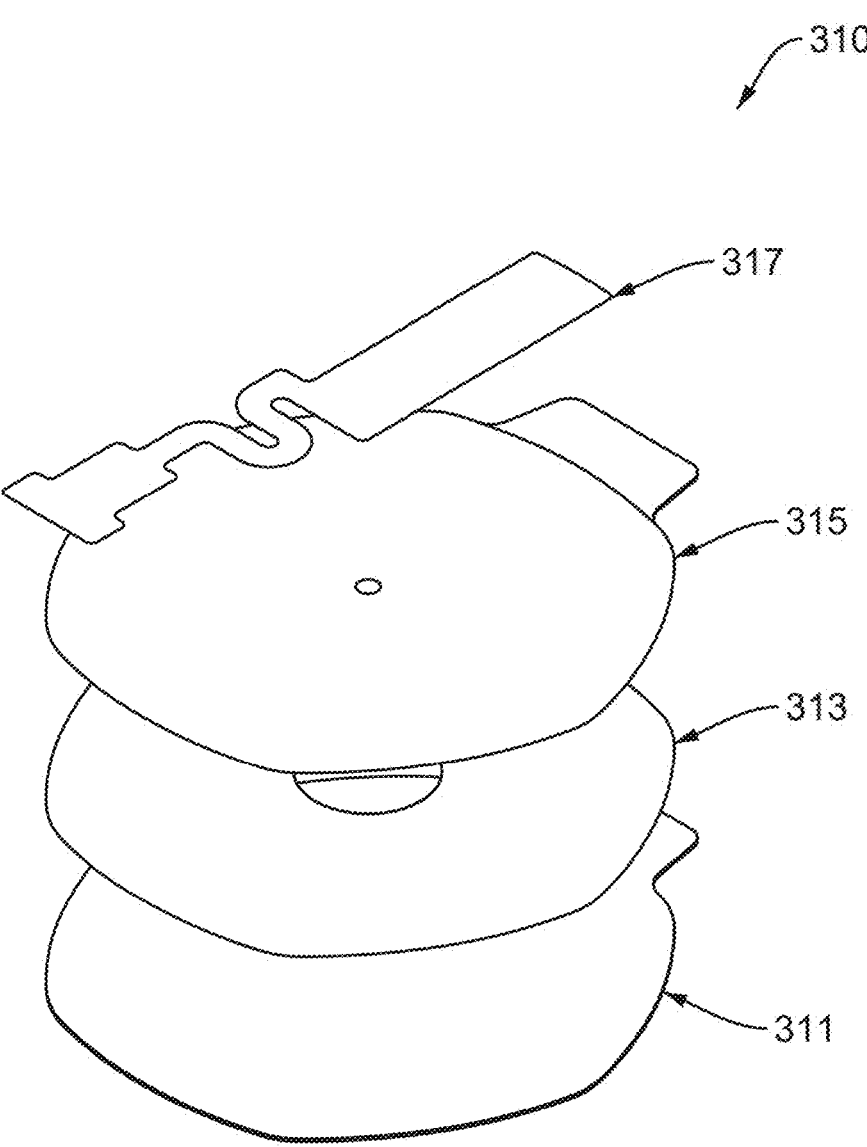
FIG. 6 is a schematic illustration of an exploded view of the example sample handling device of FIG. 5A, illustrating the component layers of the sample handing device.

FIG. 5A illustrates a perspective view of the assembled sample handling device 310, showing the distal side of the sample handling device 310 (away from a user's body) when in use. FIG. 5B illustrates a top view of the distal side of the sample handling device 310, and also shows contours of features in the more proximal layers of the sample handling device 310. FIG. 6 illustrates an exploded view of the sample handling device 310, indicating the individual layers and their order and configuration. The layers include the interface layer 311 most proximal or bottom most, with the adhesive layer 313, the access port layer 315, and the electrode and channel layer 317 forming successive distal layers.

The layers used to assemble and form the sample handling devices described herein can be generated by cutting predetermined shapes or outlines from suitable sheet material along predefined contours. FIGS. 7A, 7B and 7C illustrate the interface layer 311, the adhesive layer 313, and the access port layer 315 of the sample handling device 310, respectively, generated from material cut out along pre-defined outlines for each layer. For example, the cut outline for generating the adhesive layer 313 includes the cut out portion defining the opening and volume of the sample collection region 312. The cut outline for generating the access port layer 315 includes the opening defining the access port 314.

Figure 8:
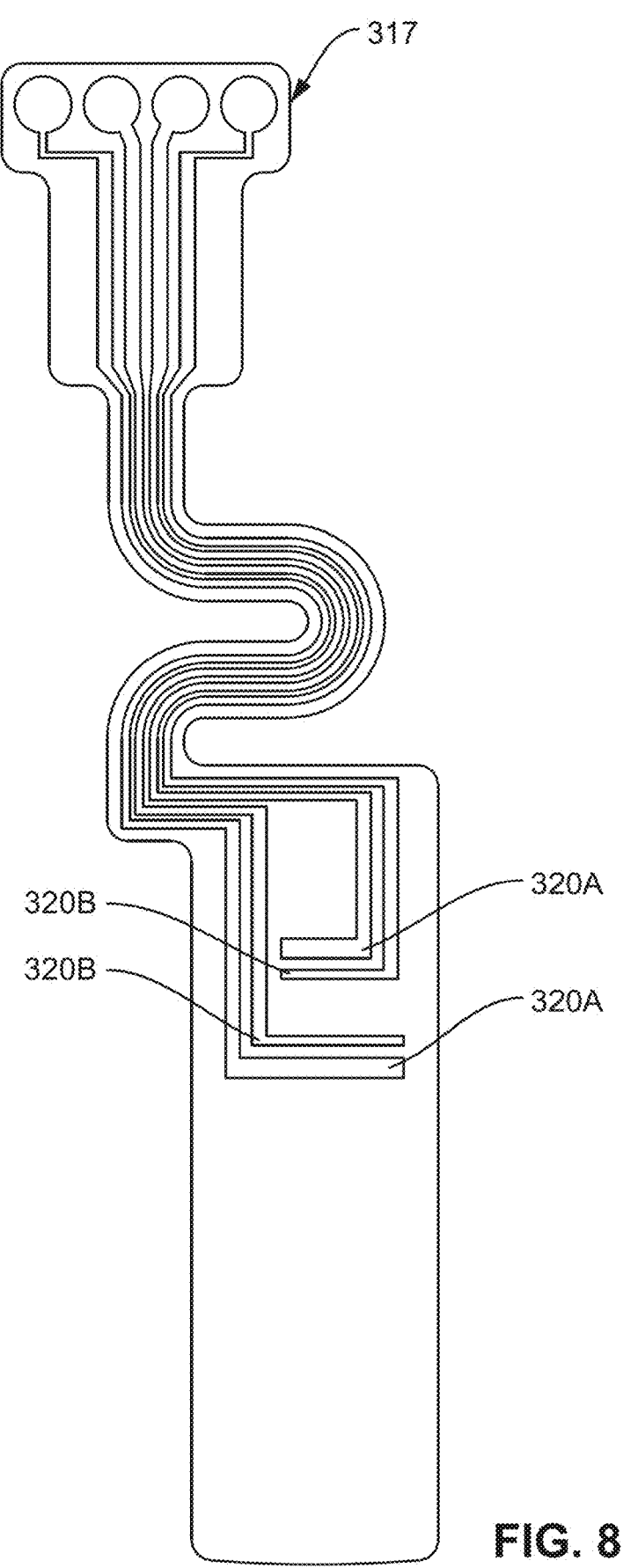
FIG. 8 is a schematic illustration of a portion of an electrode and channel layer of the sample handling device of FIGS. 5A, 5B, and 6.

FIG. 8 illustrates a top view of the distal side or surface of the electrode and channel layer 317. The contours indicate electrode traces etched or marked by printing conductive ink with 80% silver and 20% silver chloride. The electrode traces follow a path that includes serpentine shapes. Such a configuration can be used to make the electrodes have higher tolerance to stress and incorporate flexible electrical and electronic coupling. The example electrode traces indicated in FIG. 8 include four electrodes with four terminal ends at circular contact pins and four test ends situated in the test region. The four electrodes include two current delivery electrodes 320 A configured to deliver the excitation signal and two response carrying or voltage sensing electrodes 320 B configured to read a voltage across the sample bodily fluid (e.g., sweat) in response to the applied excitation signal or test current and carry the response signal to a sample processing device. The sample processing device can be electrically coupled to the sample handling device 510 via the circular terminal contact pins on the electrode traces shown in FIG. 8.

Figure 9:
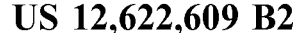
FIG. 9 is a schematic illustration of a set of electrodes in the interface layer FIG. 8.

FIG. 9 illustrates the proximal side or surface of the electrode and channel layer 317 indicating the flow channel 316, the test region 318, the test ends of the set of current delivery electrodes 320A and voltage sensing electrodes 320B, and the outlet 324 to expel the sample after testing. The schematic in FIG. 9 also illustrates the adhesive portion 323 of the electrode and channel layer 317 used to affix the electrode and channel layer 317 to the adjacent proximal layer, i.e., the access port layer 315. In some embodiments, the portion 323 can be printed with thickening ink about 0.9 mm thick before applying the adhesive layer. The layers can be assembled such that the access port in the access port layer 315 directly overlies the test region in the electrode and channel layer 317. In some embodiments, the access port can overlie a receiving portion of the flow channel other than the test region, but upstream to the test region. The receiving portion can direct the flow of the collected sample to the test region, which is situated downstream. The flow channel follows a path that includes serpentine shapes. Such a configuration can be used to increase tolerance to stress as well to include localized traps to prevent air from outside the sample handling device 310 to enter the flow channel.

Figure 10:
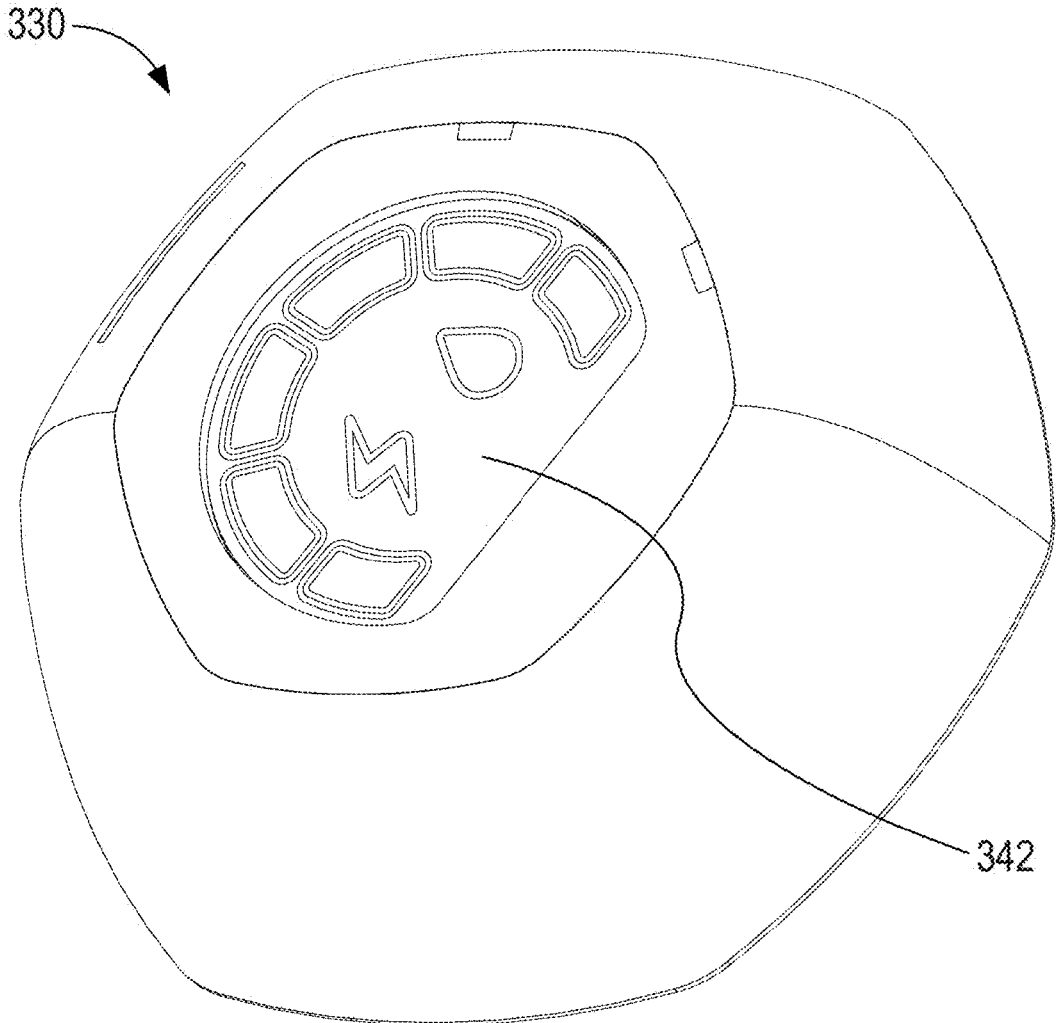
FIG. 10 is a schematic illustration of a perspective view of an example sample processing device of a SA system, according to an embodiment.

FIG. 10 illustrates a perspective view of an example sample processing device 330 that can be used with the sample handling device 310 described above. For example, the sample handling device 310 can connect to the durable electronic sample processing device 330 via a mechanical connector. After use, the sample handling device 310 can be disconnected and disposed while retaining the durable electronic sample processing device 330 to be used with a different sample handling device 310. The mechanical connector can include suitable adaptations for providing electrical connection between the durable electronics and the sample handling device. The electrical connection can include features to prevent sweat from contaminating the electrical connection between the components. The durable electronic sample processing device can be powered via disposable or rechargeable battery cells, as described previously. The durable sample processing device has a simple means of display and communication via either LEDs or a small screen. The durable electronic sample processing device may also have the ability to wirelessly communicate with a smartphone or base station which allows real time monitoring of more than one user (e.g., athletes at an event, or in a sports team, etc.).

Figure 11A:
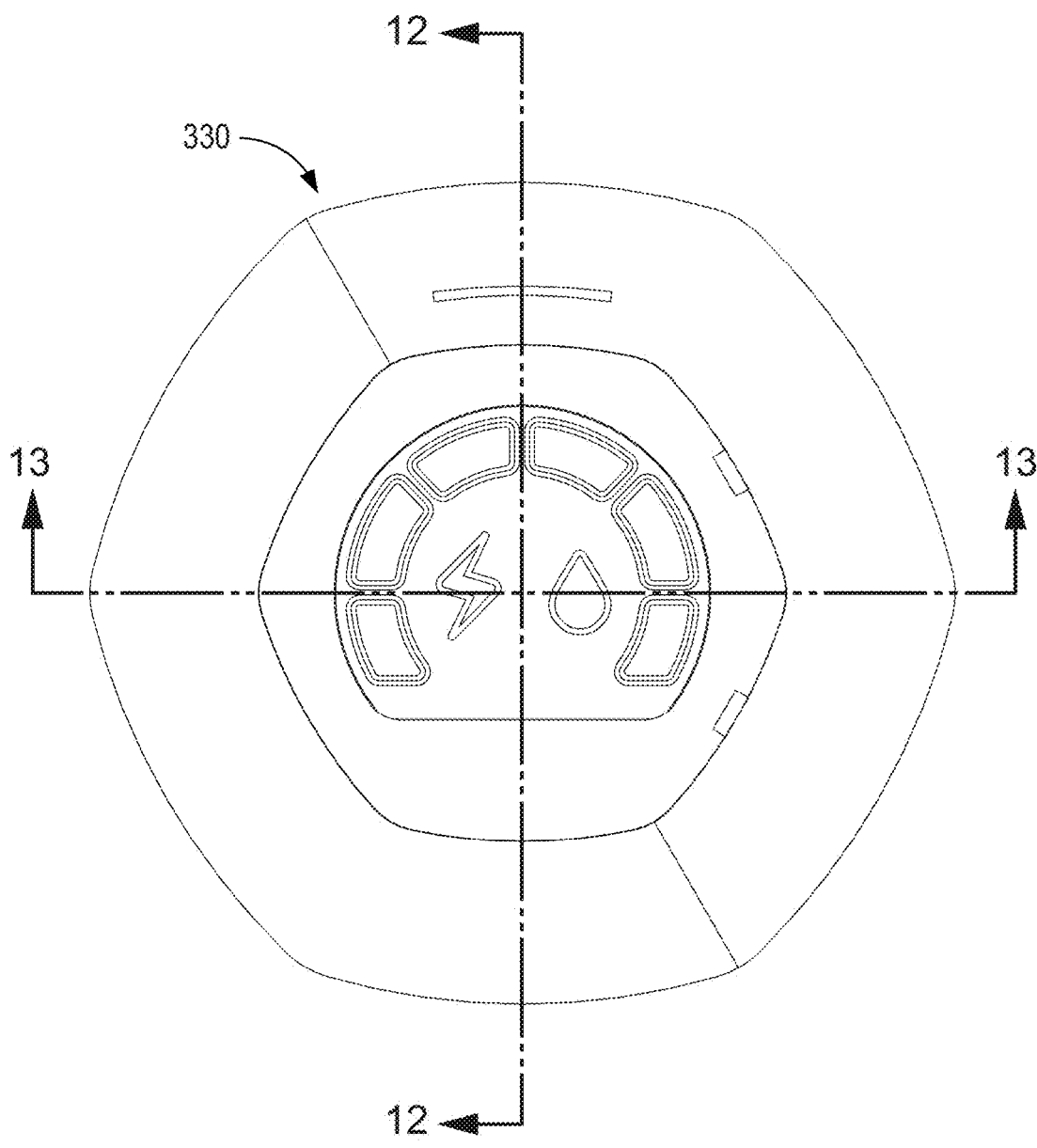
FIGS. 11A-11C are schematic illustrations of a top view, a bottom view, and a perspective view of an example sample processing device of a SA system, according to an embodiment.
Figure 11B:
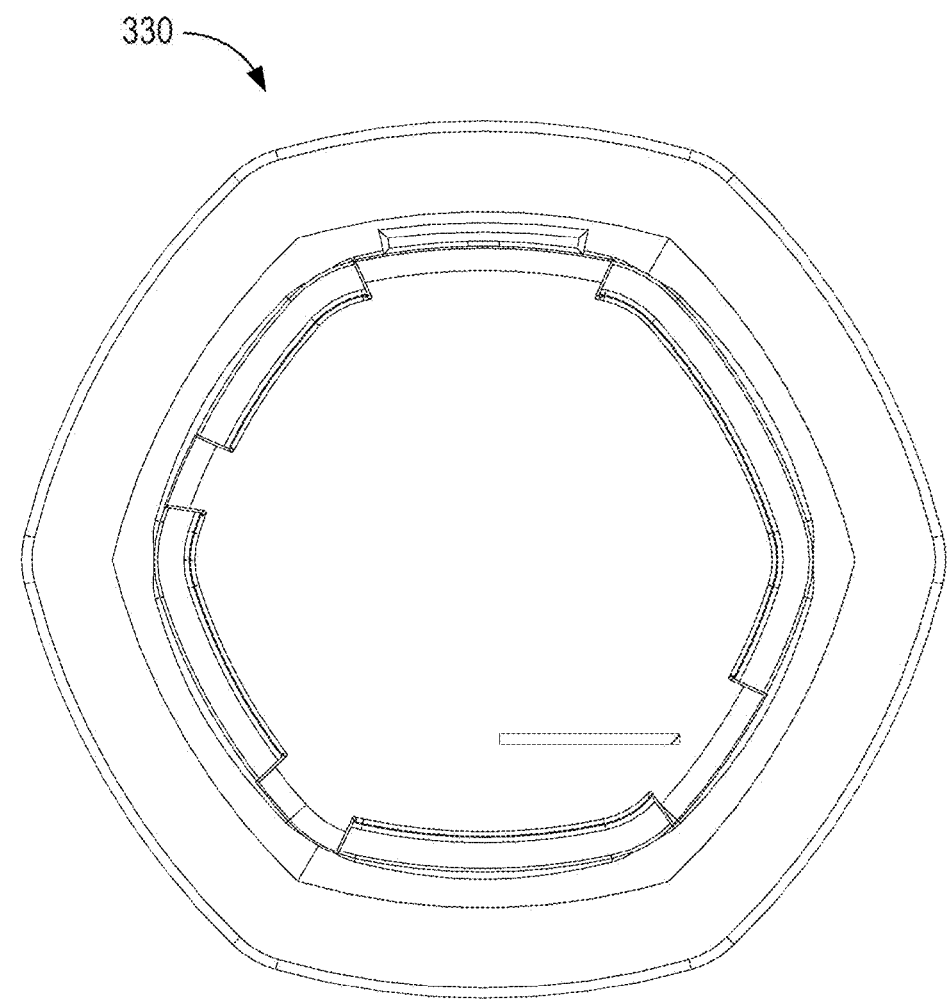
Figure 11C:
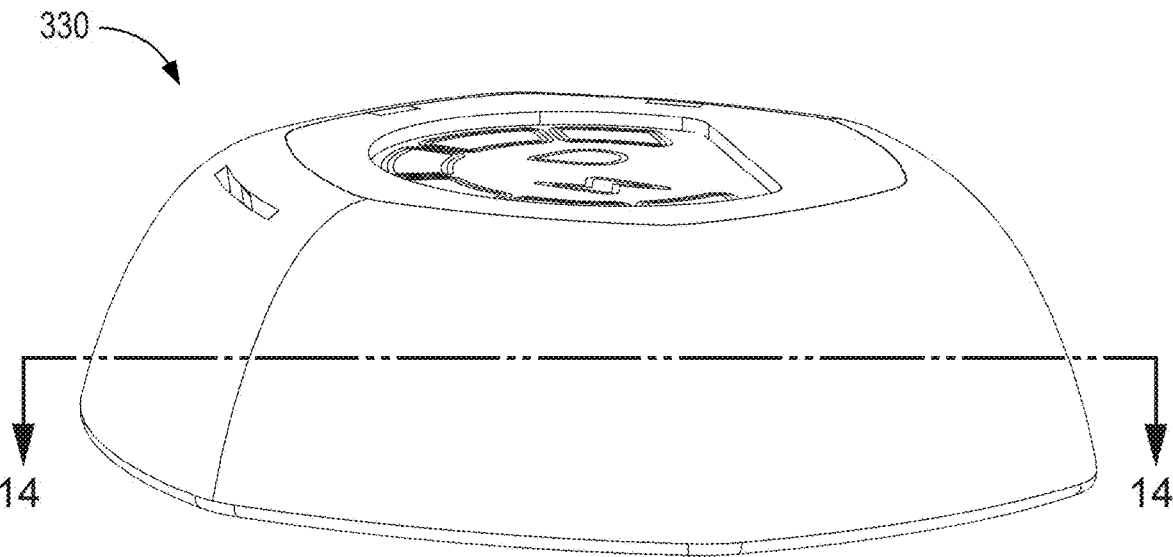
Figure 12:
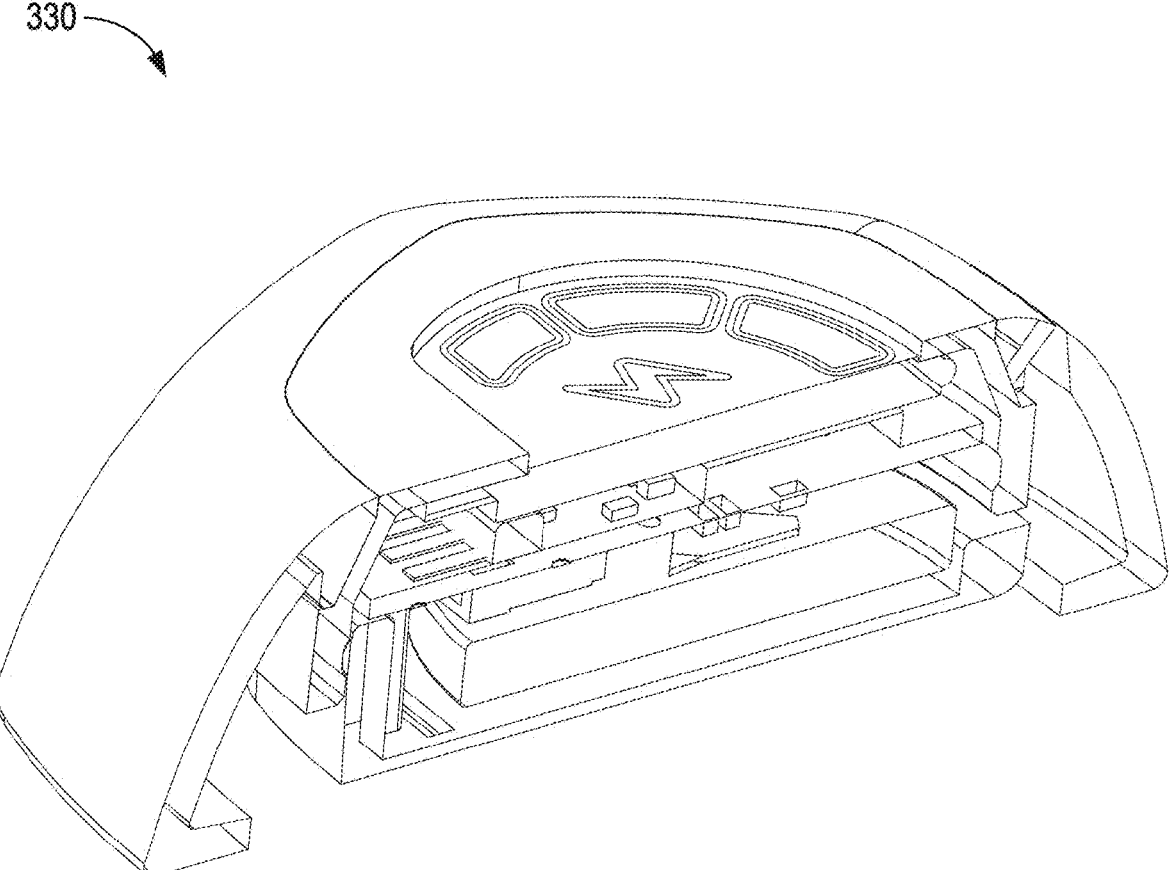
FIG. 12 is a schematic illustration of a cross-section of the sample processing device of FIG. 11A, taken along the line 12-12.
Figure 13:
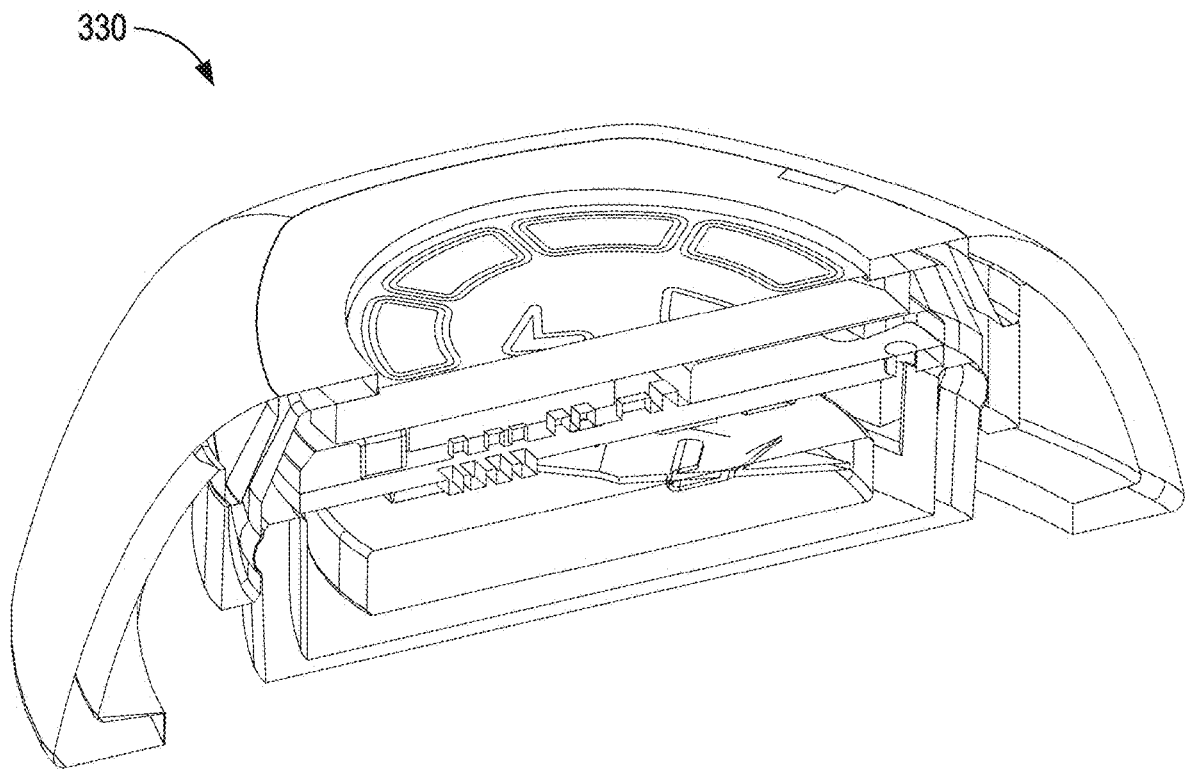
FIG. 13 is a schematic illustration of a perspective view of a cross-section of the sample processing device of FIG. 11A, taken along the line 13-13.
Figure 14:
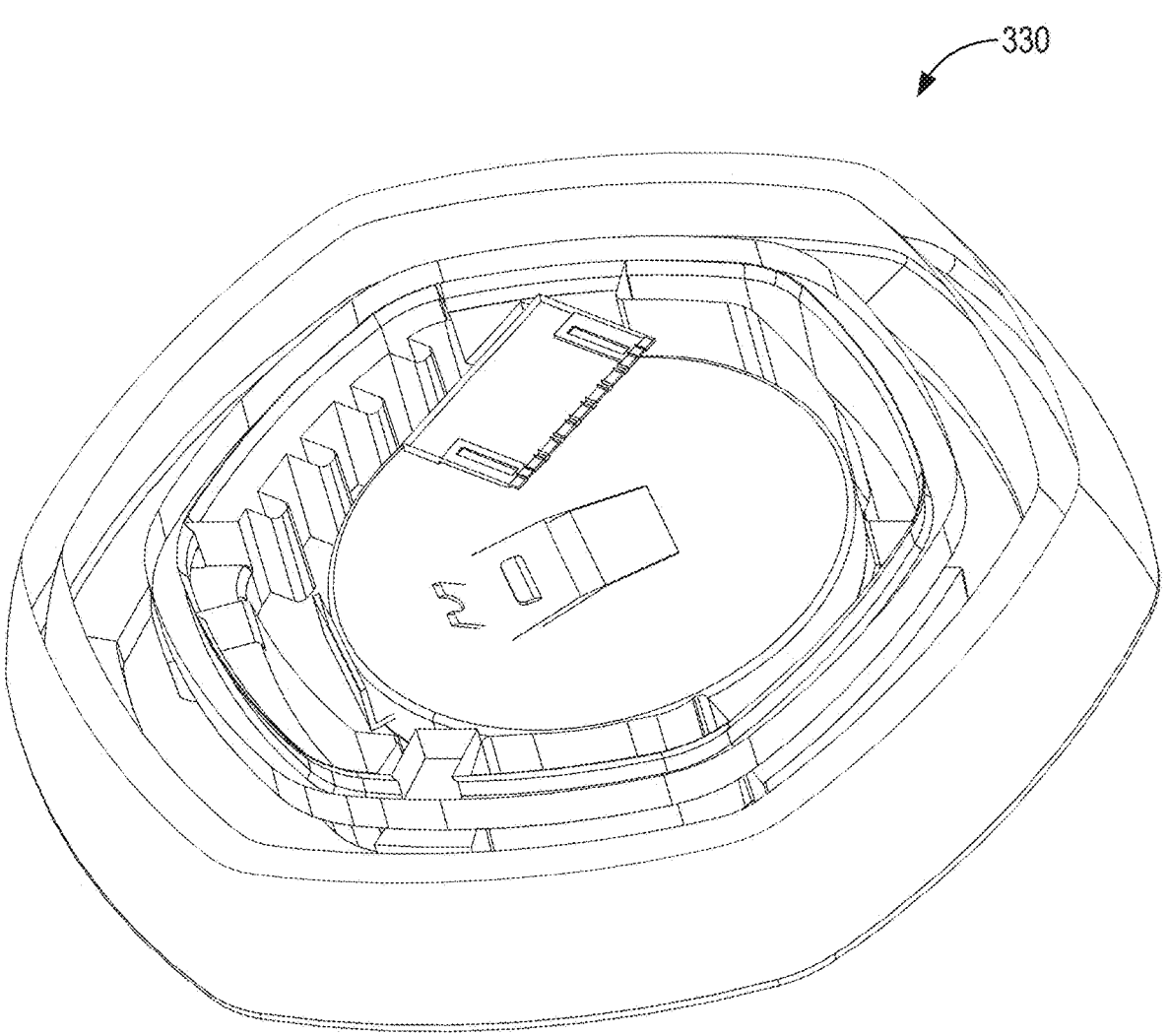
FIG. 14 is a schematic illustration of a perspective view of a cross-section of the sample processing device of FIG. 11C, taken along the line 14-14.

FIG. 11A illustrates a top view of the sample processing device 330 showing the distal surface, away from a user's body during use. FIG. 11B illustrates a bottom view showing the proximal surface of the sample processing device 330 configured to interface with a sample handling device 310 before being worn by a user. FIG. 11C illustrates a perspective view of the sample processing device 330. FIGS. 12, 13 and 14 illustrate sectional views of the sample processing device 330 with cross-sections taken along the lines 12-12, and 13-13 in FIG. 11A, and along line 14-14 in FIG. 11C, respectively. The sectional views show internal components of the sample processing device 330.

Figure 15:
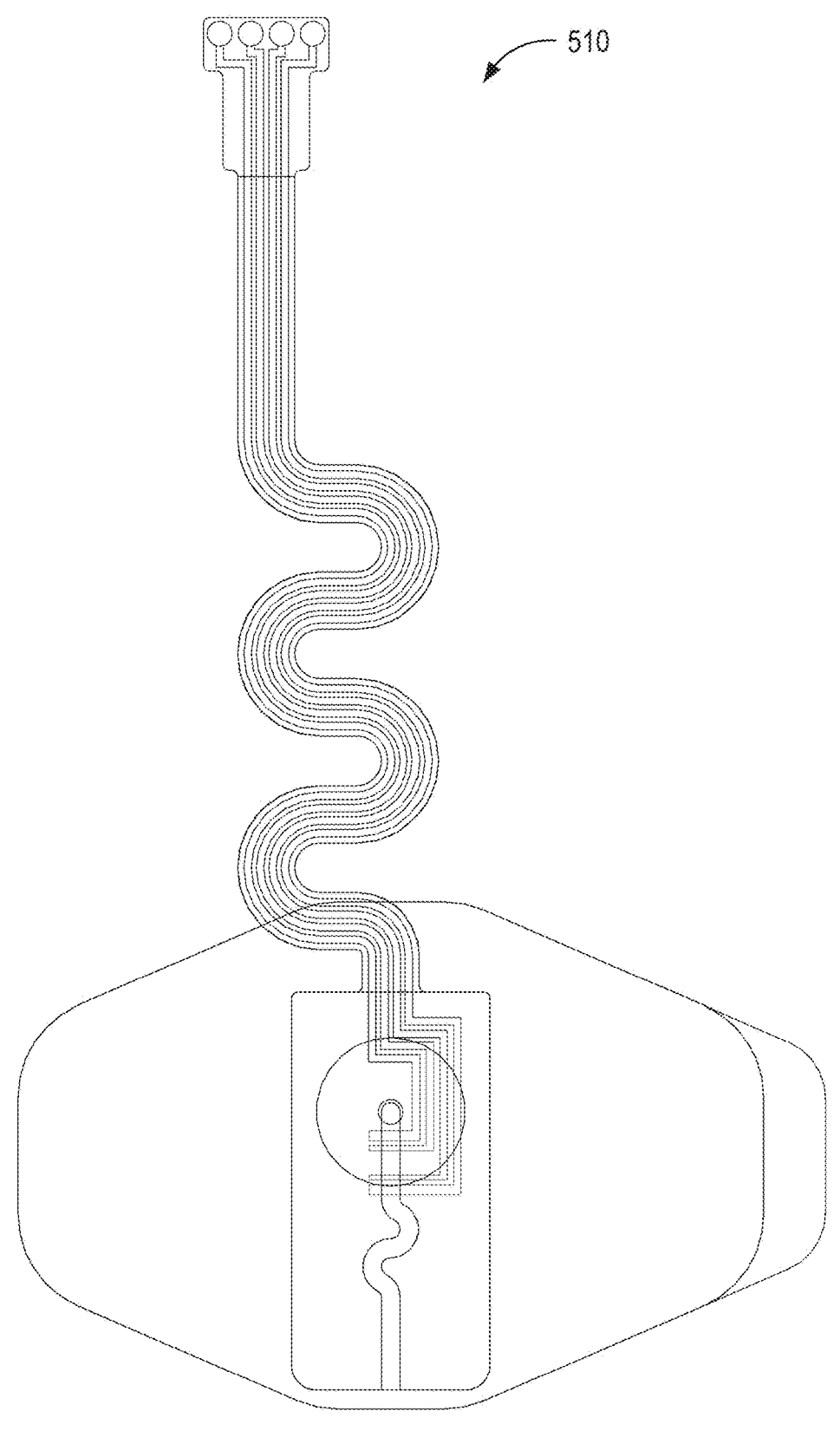
FIG. 15 is a schematic illustration of a top view of a sample handling device that can be used with an example SA system, according to an embodiment.

FIG. 15 illustrates a top view of an example sample handling device 510, while also showing contours of features in the intermediate layers of the sample handling device 510, according to an embodiment. The sample handling device 510 can be substantially similar in form and/or function to the sample handling devices 110, 210, and 310, described above. For example, the sample handling device 510 can include a sample collection region, an access port, a flow channel, a test region, and a set of electrodes, as described with reference to the sample handling device 110. The sample handling device 510 can be constructed similar to the sample handling device 210, and/or the sample handling device 310 such that it includes an interface layer 511, an adhesive layer 513, an access port layer 515, and an electrode and channel layer 517, as described with reference to the sample handling devices 210, and 310. Accordingly, such similar portions and/or aspects are not described in further detail herein.

Figure 16:
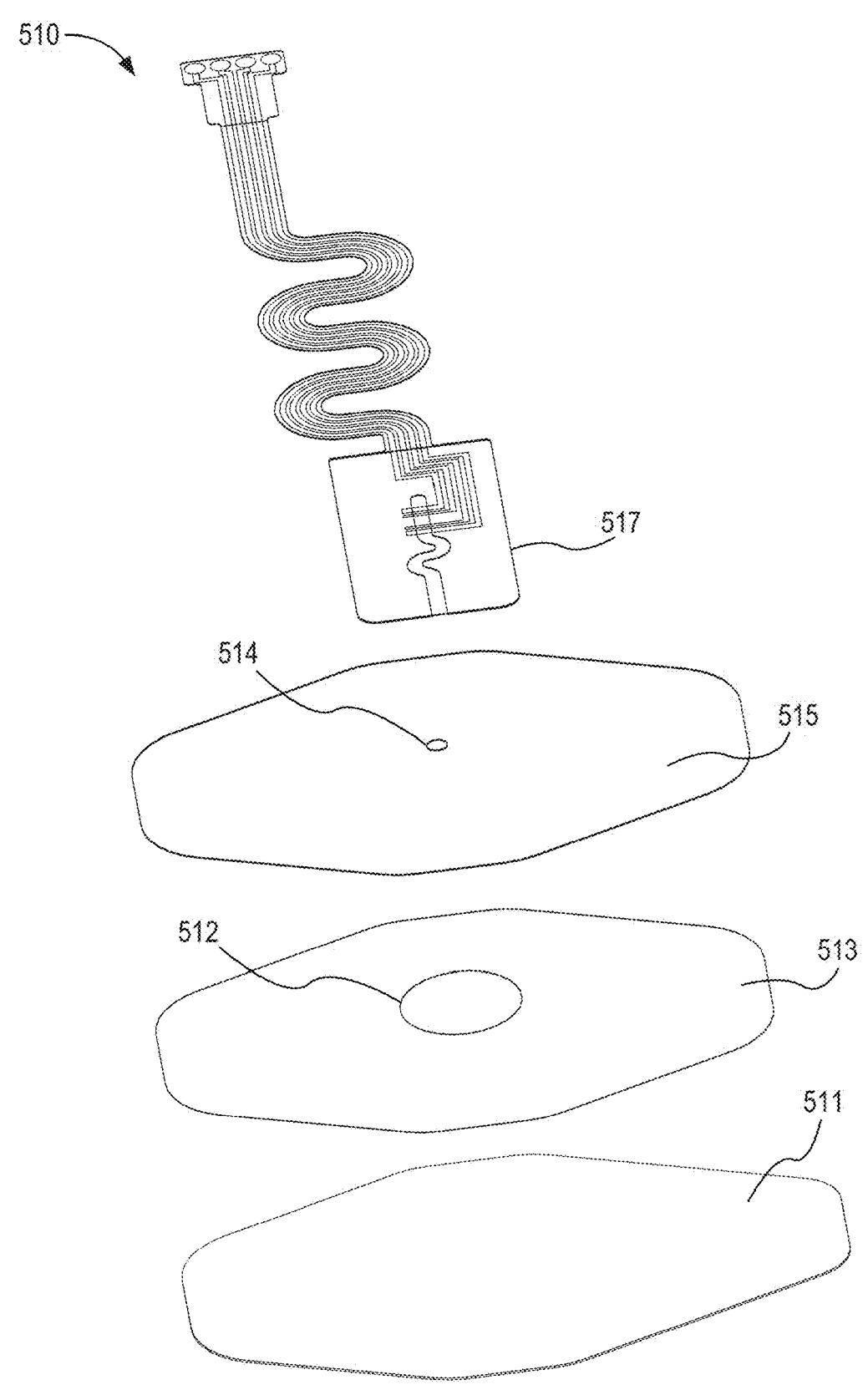
FIG. 16 is a schematic illustration of an exploded view of the sample handling device of FIG. 15, illustrating the component layers of the sample handing device.
Figure 17:
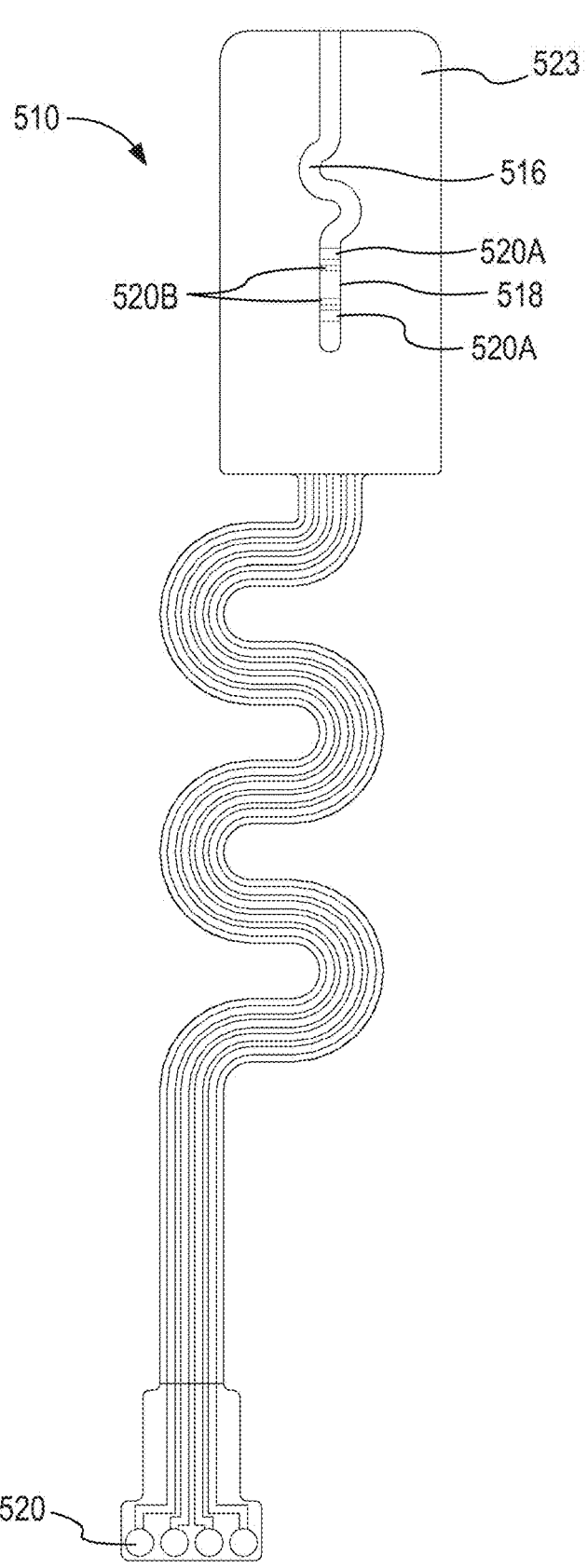
FIG. 17 is a schematic illustration of an electrode and channel layer of the sample handling of FIGS. 15-16, according to an embodiment.

FIG. 16 illustrates an exploded view of the sample handling device 510, indicating the individual layers and their order and configuration. The layers include the interface layer 511 most proximal or bottom most, with the adhesive layer 513, the access port layer 515, and the electrode and channel layer 517 forming successively distal layers. FIG. 17 illustrates a bottom view of the electrode and channel layer 517 showing the proximal surface of the layer 517 that is configured to interface with the adjacent layer of the sample handling device 510, i.e., the access port layer 515. As described with reference to the electrode and channel layer 317 of sample handling device 310, the electrode and channel layer 517 includes electrode traces or tracks with serpentine portions configured to better tolerate stress.

Figure 18:
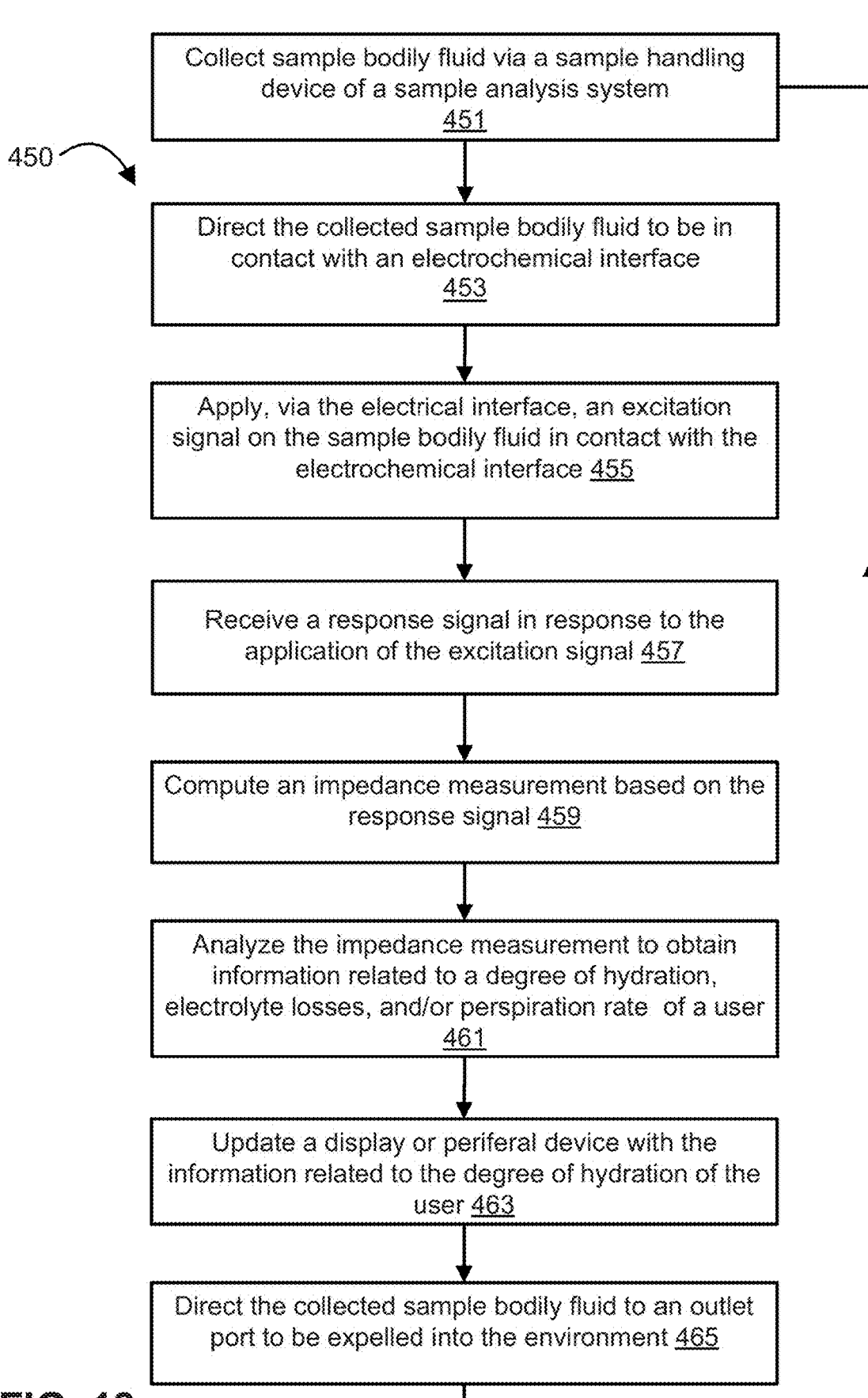
FIG. 18 illustrates a schematic flowchart of an example method of using a SA system to measure and analyze a degree of hydration of a user, according to an embodiment.

Referring now to FIG. 18, a flowchart is shown illustrating a method 450 of using a sample analysis system including a sample handling device and a sample processing device, such as those described herein. The sample analysis system can be used to collect, test and analyze a sample of bodily fluid (e.g., sweat) at a near instantaneous, real-time rate. In some embodiments, the sample handling device can be similar to and/or substantially the same as any of the sample handling devices 110, 210, 310, and/or 510 described herein.

The method 450 includes collecting a sample of a bodily fluid via a sample handling device of a sample analysis system, at 451. In some instances, for example, the bodily fluid source can be sweat. As the sample, collection region of the sample handling device is filled to capacity or as a substantial amount of sample bodily fluid has been collected, the collected sample is directed to be in contact with an electrochemical interface at 453. In some instances, the collected sample is continuously directed towards the electrochemical interface, tested and expelled as new samples are continuously collected. For example, the sample fluid is directed through an access port via flow channel to a test region where the sample bodily fluid is made to come in contact with the test ends of a set of electrodes.

The sample analysis system is configured to apply, via the electrical interface, an excitation signal on the sample bodily fluid in contact with the electrical interface, at 455. For example, the excitation signal is delivered via the test ends of a set of current delivery electrodes. The sample analysis system is configured to receive a response signal, from the sample bodily fluid, at 457, after the application of the excitation signal at 455. For example, the response voltage is read via the test ends of a set of voltage sensing electrodes.

At 459, the sample analysis system computes, via a sample processing device, an impedance measurement based on the excitation signal applied at 455 and the response signal received at 457. The impedance measurement is then analyzed at 461, to obtain information related to a degree of hydration, electrolyte losses, and/or perspiration rate of a user. Based on the analyses the sample analysis system updates a display or a peripheral device associated with the sample processing device with the information related to the degree of hydration of the user at 463. For example, the impedance measurement is correlated with a measure of salinity of the user's sweat and the measure of salinity is used to infer the degree of hydration, electrolyte losses, and perspiration rate of the user. In some instances, the applying the excitation signal at 455, reading the response at 457, computing the impedance measurement at 459 and inferring the degree of hydration, electrolyte losses, and/or perspiration rate at 463 can be carried out in a continuous manner, with the sample sweat direct to flow at a suitable flow rate. After the testing of the sample of bodily fluid the sample is continuously directed to an outlet or exit port to be expelled into the environment at 465.

In some embodiments, as described previously, the sample handling device of the sample analysis system can be configured to continuously collect and direct samples or volumes of the bodily fluid to the test region, test the samples, and expel the samples to make room for the next sample. Thus, the method 450 can be carried out repeatedly for multiple samples providing intermittent or continuous results from testing and analysis. The sample analysis system can be configured such that the time taken to collect a sample of bodily fluid sufficient for testing, time taken to direct the fluid to the test region and test the sample, and time taken to analyze the results of testing and expelling the sample can be reduced as required to suit the needs of the user. In some instances, adaptations of one or more parts of the sample handling device can be made to form a range of sample handling devices with varying response rates such that different users can obtain custom fitted or personalized sample analyses systems with personalized sample handling devices and/or personalized sample processing devices. In some embodiments, the data from different users (e.g., a team) can be stored, retained, and/or displayed to monitor the degree of hydration, electrolyte losses, and/or perspiration rate of the multiple users. In some instances, a user can choose a suitable sample analysis system based on the kind of activity they may engage or and the amount or rate of sample analysis they may desire.

For example, a user with a history of higher perspiration can use a sample handling device that includes a sample collection region with a suitably smaller opening to cover a smaller fraction of sweat glands compared to the sample handling device used by a user with very little perspiration. In some instances, a high performance athlete requiring higher rates of sample analysis can use a sample handling device with a sample collection region of smaller fluid capacity such that smaller amounts of sweat are tested more frequently when the high performance athlete user is using the sample analysis system when engaged in activities.

In some instances, the sample processing device can be personalized to store and retain history of results from analysis of a user's status of health for future uses of the sample analysis system. In some embodiments, the sample analysis system can be configured to export a set of collected data and/or analyses from the memory of the sample processing device to a remote device after predetermined, intermittent, periods. For example, in some implementations the sample analysis system may export data and/or results of analyses to a wearable device or a smart phone at every change or replacement of the sample handling device. In some embodiments, the exported data can be retained and logged, and associated with suitable identifiers tagged to users. The data associated with users can then be used to chart a progress of a user's health, performance or the like, and in some instances to predict health states for individual users before they undertake planned activities. In some implementations the sample analysis system can include remote applications run on remote servers or compute devices to provide a plan for a user, for example a hydration strategy that might best suit a user such as a performance athlete when planning to undertake a pivotal sporting event. The remote applications can include prediction algorithms that can be used to devise strategic plans to hydrate, maintain electrolyte balance, and the like.

Figure 19:
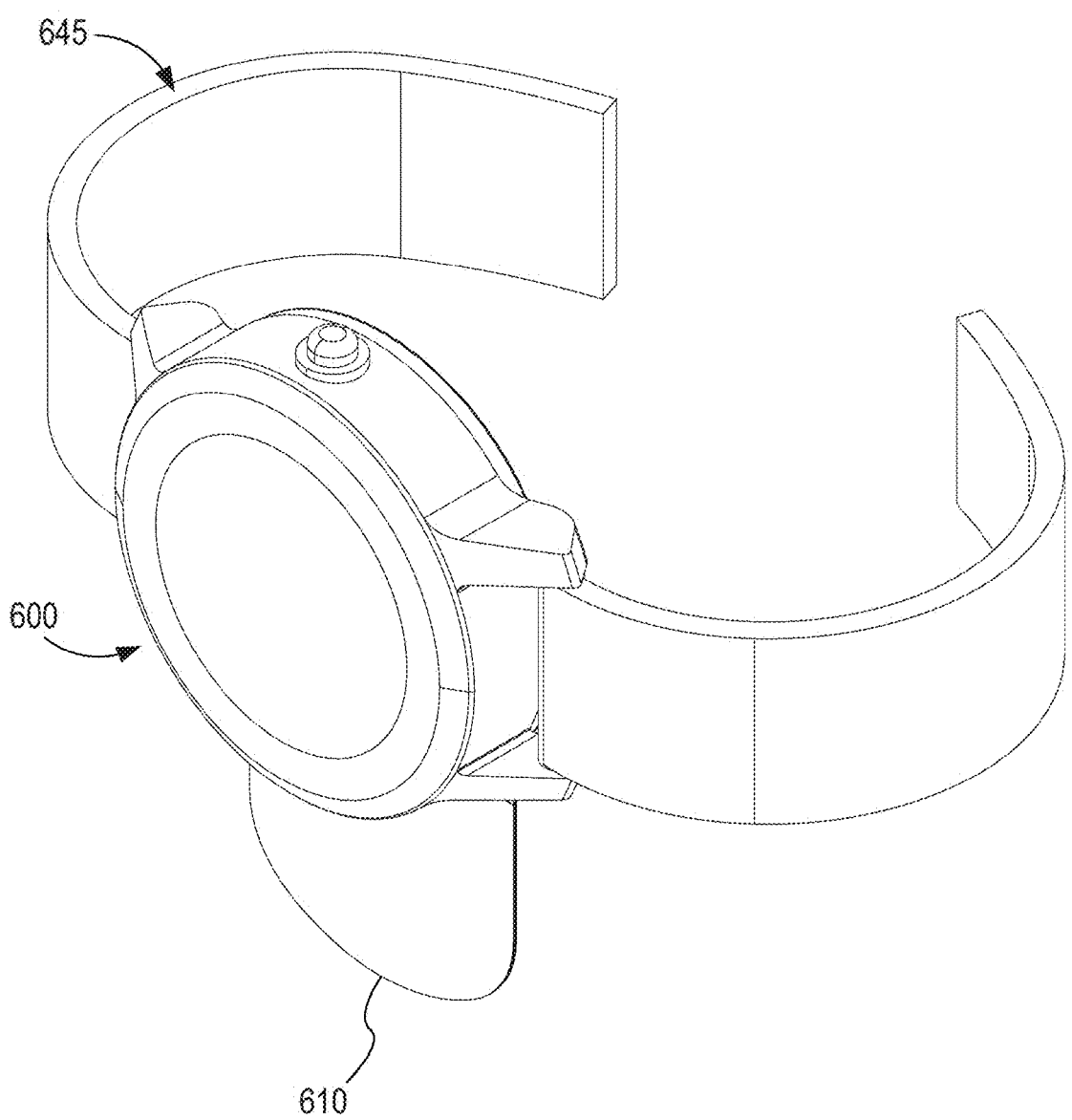
FIG. 19 is a schematic illustration of a perspective view of an example SA system integrated with an example wearable device, according to an embodiment.
Figure 20:
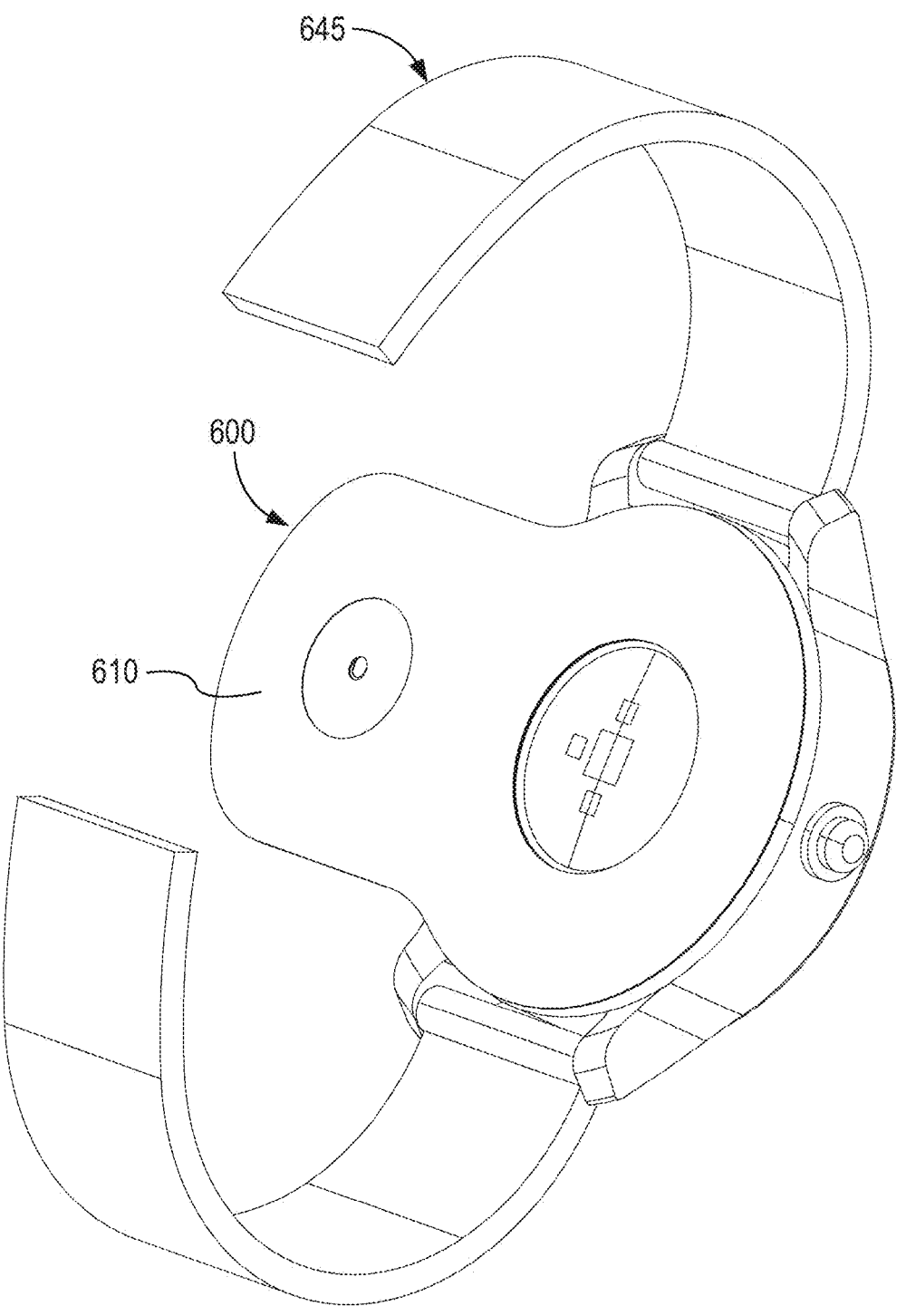
FIG. 20 is a schematic illustration of a perspective view of the rear of the SA system of FIG. 19 integrated with the example wearable device of FIG. 19.

As described previously, the sample analysis systems and/or the sample handling device described herein can be integrated with wearable devices such as smart watches, odometers, GPS systems, etc. FIGS. 19 and 20 illustrate an example embodiment of a sample analysis system 600, including a sample handling device 610, integrated with a wearable smart watch device 645. In some instances, when the sample analysis system including a sample processing device is integrated with the wearable device, the sample processing device can include interfacing elements to physically and electrically connect with the sample handling device. The sample processing device can perform functions such as provide instructions about delivery of an excitation signal, provide the excitation signal in the form of test current to the terminals of the electrodes, receive a response signal obtained via the electrodes from the sample being tested. The sample processing device can include the electronics required to analyze the response signal and/or communicate the data to remote compute devices etc. For example, the electronics can be programmed with unique analytical code to interpret the readings collected. The interpreted readings can be output to the display of the sample processing device to provide the wearer with information about sweat rate and overall hydration status. In instances where the sample handling device can be directly interface with the wearable device, the wearable device can be configured to directly engage physically and electrically with the sample handling device and perform functions like providing instruction, providing the excitation signal, receiving and analyzing the response signal, etc. The electronics included in the wearable device can be used to execute programs with a unique analytical code to interpret the readings collected. The interpreted readings can be output to the display of the wearable device or a display associated with a remote compute device (e.g., a smart phone) to provide the wearer with information about sweat rate and overall hydration status.

Figure 21:
FIG. 21 is a schematic illustration of a top view of a sample handling device that can be used with an example SA system, according to an embodiment.
Figure 22:
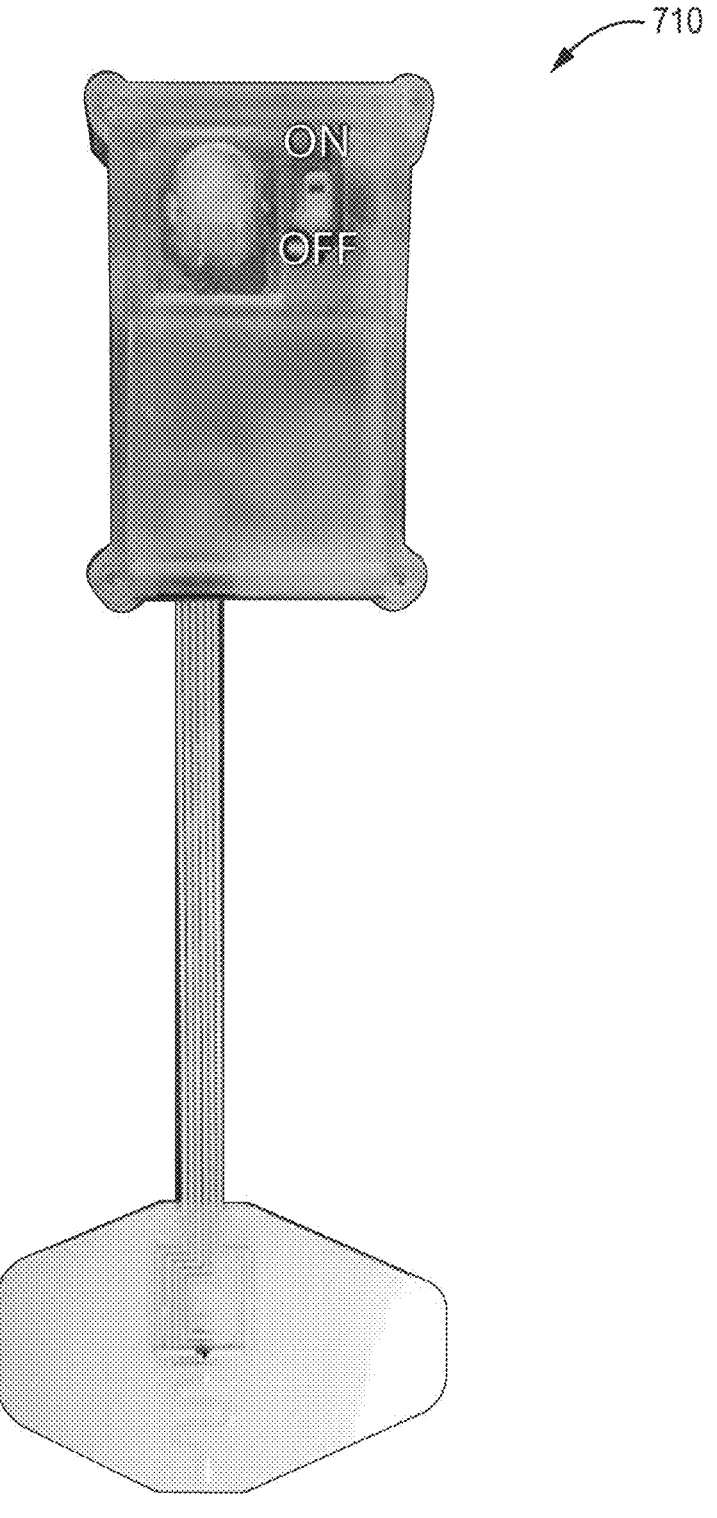
FIG. 22 is a top view image of the sample handling device of FIG. 21, according to an implementation.
Figure 23A:
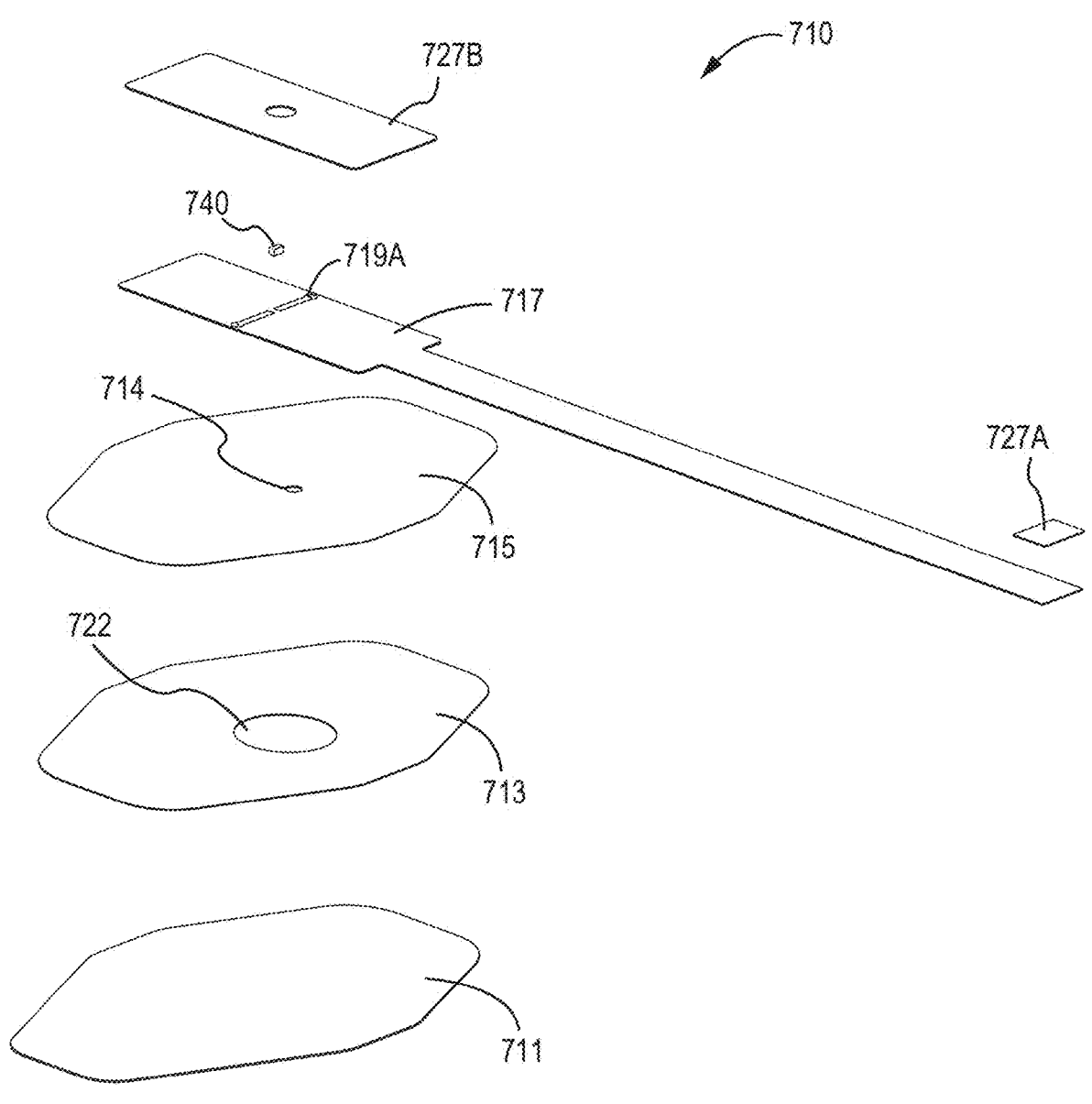
FIG. 23A is a schematic illustration of a perspective exploded view of the sample handling device of FIG. 21, illustrating the component layers of the sample handing device, according to an implementation.
Figure 23B:
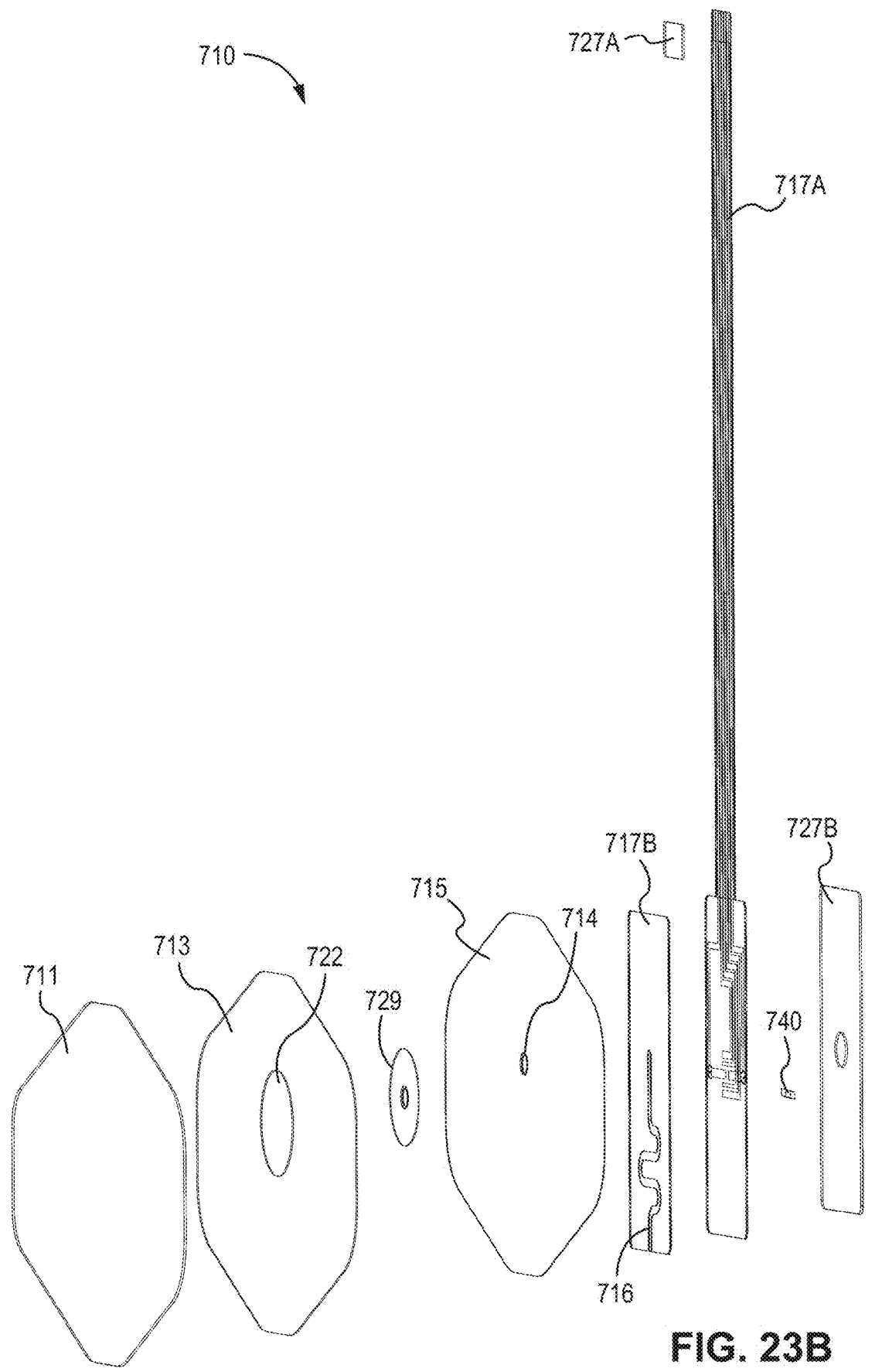
FIG. 23B is a schematic illustration of an exploded view of the sample handling device of FIG. 21, illustrating the component layers of the sample handing device, according to an implementation.
Figures 24A, 24B:
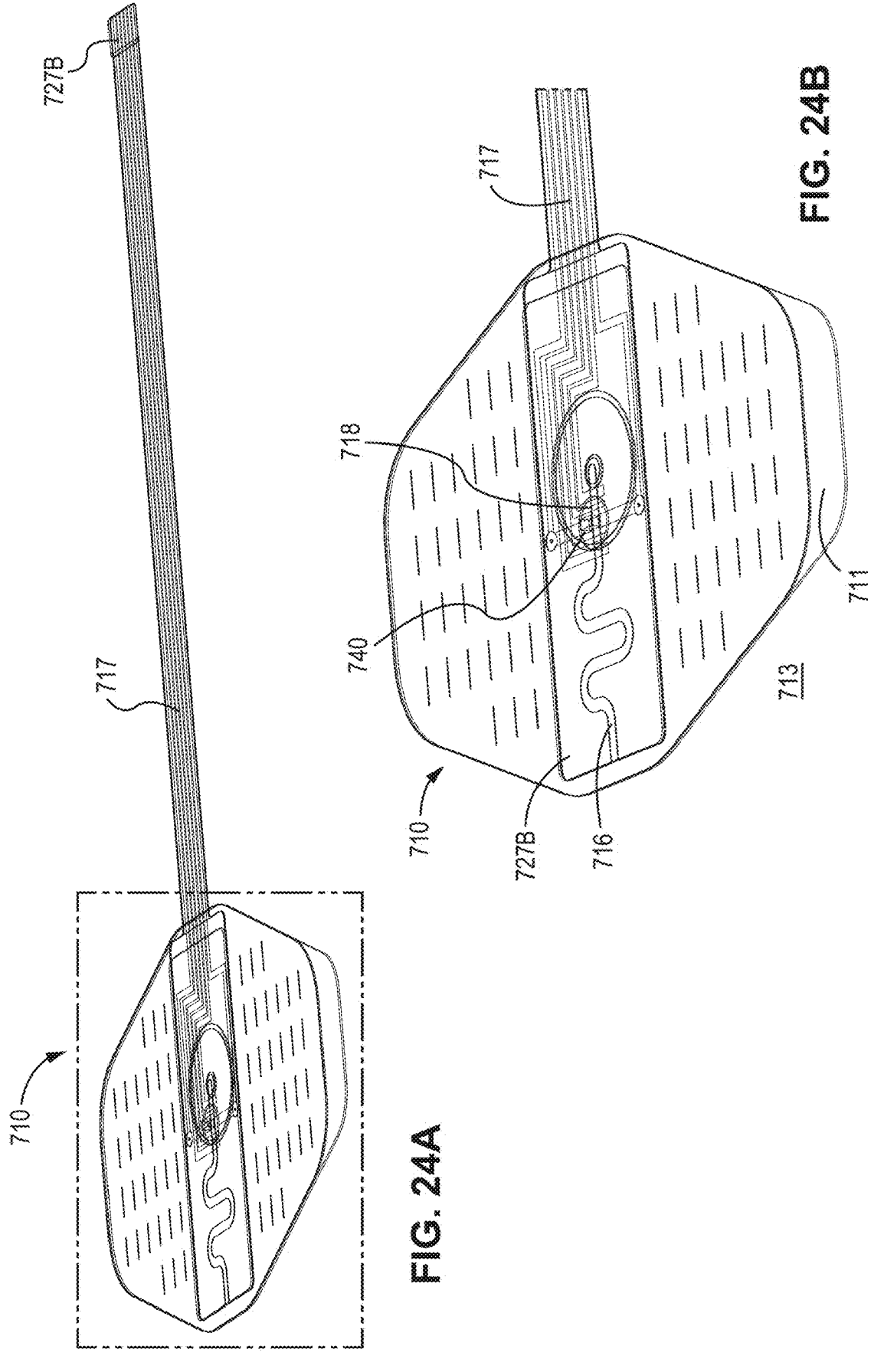
FIG. 24A is a schematic illustration of a perspective side view of the sample handling device of FIG. 21, according to an implementation.
FIG. 24B is an enlarged view of the boxed region of FIG. 24A.
Figure 24C:
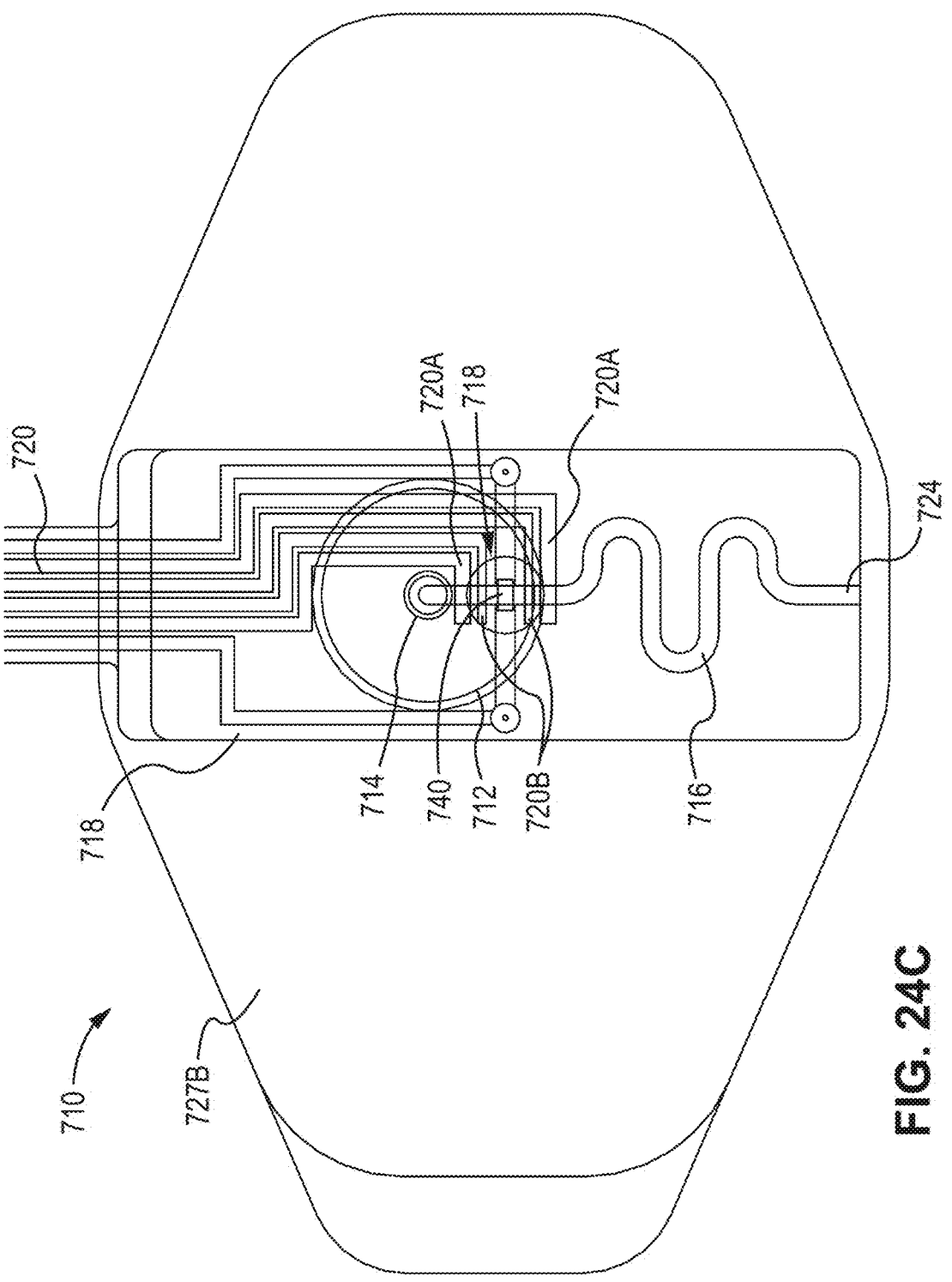
FIG. 24C is a schematic diagram of a top view of a portion of the sample handling device of FIG. 21, with the layers rendered transparent to show overlay, according to an implementation.

FIG. 21 is a schematic illustration of a top view of a sample handling device 710, the layers being rendered transparent to show underlying features in the intermediate layers of the sample handling device 710, according to an embodiment. FIG. 22 is a top view image of an example implementation of the sample handling device 710 of FIG. 21. FIG. 23A is a schematic illustration of an exploded view of the sample handling device 710 according to an example implementation. FIG. 23B is a schematic illustration of an exploded view of the sample handling device 710 according to another example implementation. FIG. 24A shows a perspective view of the device 710 and 24B shows an enlarged view of a portion of FIG. 24A indicated by the dashed box. The portion is also shown in top view in FIG. 24C, with the layers rendered transparent such that underlying features are visible.

The sample handling device 710 can be substantially similar in structure and/or function to the sample handling devices, 110, 210, 310, and/or 510 described herein. For example, the sample handling device 710 can include a sample collection region 712, an access port 714, a flow channel 716, a test region 718, a set of electrodes 720, and a temperature sensor 740 that can be substantially similar to that described with reference to the sample handling device 110. The sample handling device 710 can be constructed similar to the sample handling device 210, and/or the sample handling device 310 such that it includes an interface layer 711 which can be a release liner, an adhesive layer 713 that includes an opening 722 of the sample collection region 712, an access port layer 715 defining the access port 714, and an electrode and channel layer 717, as described with reference to the sample handling devices 210, and 310. Accordingly, such similar portions and/or aspects are not described in further detail herein.

In some embodiments, the flow channel 716 can be defined by a tortuous shape as shown in FIG. 21 to reduce and/or prevent air ingress and/or undesired fluid movement, for example back-flow or "mixing" within the flow channel. In some embodiments, the tortuous shape of the flow channel 716 can be configured such that the flow rate of the sample of bodily fluid being tested is determined by the rate of supply of the bodily fluid (e.g., rate of perspiration) and not influenced by other lateral effects like gravity, body motion of the user, etc. The sample handling device 710 can include a stiffener layer 727A configured to provide structural support to a portion of the electrode and channel layer 717, for example, at the portion to be contacted by a sample processing device (e.g., sample processing device 130, 330, etc.). In some embodiments, as shown, the sample handling device 710 can include a stiffener layer 727B configured to provide support to a cell portion overlying regions including the access port 714, the test regions 718, etc. As can be seen in FIGS. 23A and 23B, the stiffener layer 727B can include an aperture defined to permit space for the temperature sensor 740 upon assembly of the layers. In some implementations, and/or in some embodiments, the sample handling device 710 can include one or more spacer portions 729 included to occupy space in the sample collection region 712 such that the initial volume of bodily fluid required to urge the flow of fluid through the flow path 716 may be reduced compared to implementations without the spacer layer 729. In some embodiments, the spacer portion 729 can be included in the access port layer 715. For example, the access port layer 715 can be made from clear polyester (PET) material (e.g., Melinex 454 or an equivalent material)

of a specified thickness (e.g., 3 mil (75 micron)). The access port layer 715 can include the spacer portion 729 defined by increased thickness via printed space ink (e.g., thickness of 4 mil (0.10 mm) spacer ink). As shown, the spacer portion 729 can define a through aperture aligning with the access port 714 such that the fluid capacity of the sample collection region is reduced (e.g., by the volume of the spacer portion 727) and the fluid collected in the available portion of the sample collection region 712 can be urged via the aperture and the access port 714 towards the test region 718 defined on the electrode and channel layer 717.

FIG. 25A is a schematic illustration of a bottom view of the electrode and channel layer 717 showing the channel layer 717B. FIGS. 25B and 25C are schematic illustrations of a bottom view and side view, respectively, of the electrode layer with the channel layer removed. FIG. 25B shows the electrode layer 717A including electrode tracks 717C on the bottom surface of the electrode layer 717A and electrical vias 717D. FIG. 25D is a top view of the electrode layer 717A showing the electrode tracks 717C on the top surface of the electrode layer 717A. FIG. 25 E is a schematic illustration of an enlarged view of the cell portion of the electrode layer 717A, indicating electrode tracks 717C on the top and bottom surfaces of the electrode layer 717A and the electrical vias 717D.

Figure 25E:
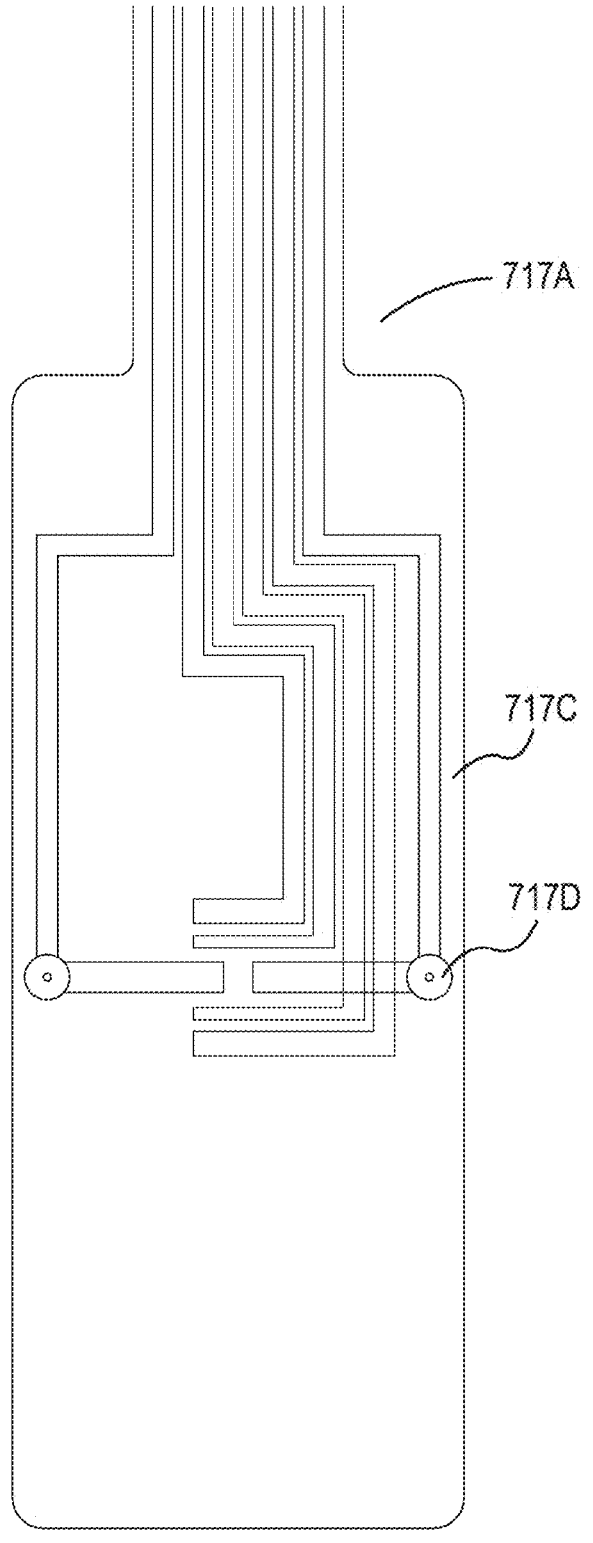
FIG. 25E is a schematic illustration showing a magnified view of a portion of the electrode layer of FIGS. 25B-25D, indicating top and bottom portions of the electrode layer, according to an implementation.

The electrode and channel layer 717 can be made of the electrode layer 717A and the channel layer 717B, as shown in FIG. 23B. The electrode layer 717A and/or the channel layer 717B can be made of any suitable material of a suitable thickness. For example, the electrode and channel layer 717 can be formed using clear 5 mil PET. The channel layer 717B can be defined at the bottom or proximal surface of the electrode and channel layer 717, closer to the body of the user when in use, and include a cell portion and an electrode track portion. The cell portion of the channel layer 717B can be formed using spacer ink such that the contours of the flow channel 7176 define a trench forming the flow channel 716. The spacer ink can be of any suitable thickness, which can at least partially determine a cross sectional thickness of the flow channel. The spacer ink thickness can be for example 2 mil (0.05 mm). In some implementations, the spacer ink can be applied to the channel layer 717B followed by a sprayed application of adhesive within a suitable specified maximum thickness (e.g., a maximum of 1 mil (0.025 mm). The channel layer 717B can include the electrode track portion 717E printed on the proximal or bottom surface (towards the body of the user) with dielectric ink of a specified thickness (e.g., 1 mil (0.025 mm). In some embodiments, the electrode track portion can be substantially straight to avoid entanglement with a user's clothing and/or the like during use. The electrode layer 717A can be defined on the top or distal portion of the electrode and channel layer 717 as shown in FIGS. 25B-25D. The electrode track portion of the electrode layer 717A can include the electrode tracks 717C defined on a bottom or proximal surface (closer to the user's body when in use) to form the sample ends of the electrodes 720 that can be in fluidic communication with at least a portion of the flow channel 716 at a set of test regions 718 such that bodily fluid flowing through the flow channel 716 at the test regions 718 can be tested. The electrode tracks can be configured to provide electrical connectivity between sample ends of the set of electrodes 720 and their respective terminal ends configured to connect with a portion of a sample processing device (e.g., sample processing device 130, 330, etc.). In some embodiments, the sample handing device 710 can include a temperature sensor 740 and the electrode layer 717A can include electrical vias or through holes 717D and electrode tracks defined in the top or distal surface (away from the user's body during use) in communication with the electrical vias 717D, as shown in FIG. 25D. The electrode tracks on the distal surface and in communication with the electrical vias 717D can be configured to provide electrical connectivity to the temperature sensor 740 to send to and/or receive signals from the temperature sensor 740. FIG. 25E shows an enlarged view of the top (distal) and bottom (proximal) surfaces of the cell portion of the electrode layer 717A, according to some embodiments.

The electrodes 720 can include excitation electrodes 720A and sensing electrodes 720B positioned to define a test region 718. In use, a sample of bodily fluid can be collected at the sample collection regions 712 and directed to flow via the access port 714 through the flow channel 716 and past the test region 718. The temperature sensor 740 can be suitably located to measure the temperature of fluid at the test region 718. An excitation signal (e.g., a current) can be applied via the excitation electrodes 720A and a response signal (e.g., voltage response) can be received by the sensing electrodes 720B to calculate an impedance associated with a sample of bodily fluid at the test region. The temperature associated with the sample of bodily fluid can be measured by the temperature sensor 740. The response signal and the measured temperature can be sent, via the electrode tracks, to a sample processing device at each time point of testing. Multiple samples of bodily fluid can be tested over multiple time points as bodily fluid is collected, tested and ejected at the exit 724 in a continuous manner. The sample processing device can receive response signals and/or measurements of temperature associated with samples of bodily fluid over a course of time and analyze the signals and/or measurements, or store/transmit the signals for further processing.

Figure 26A:
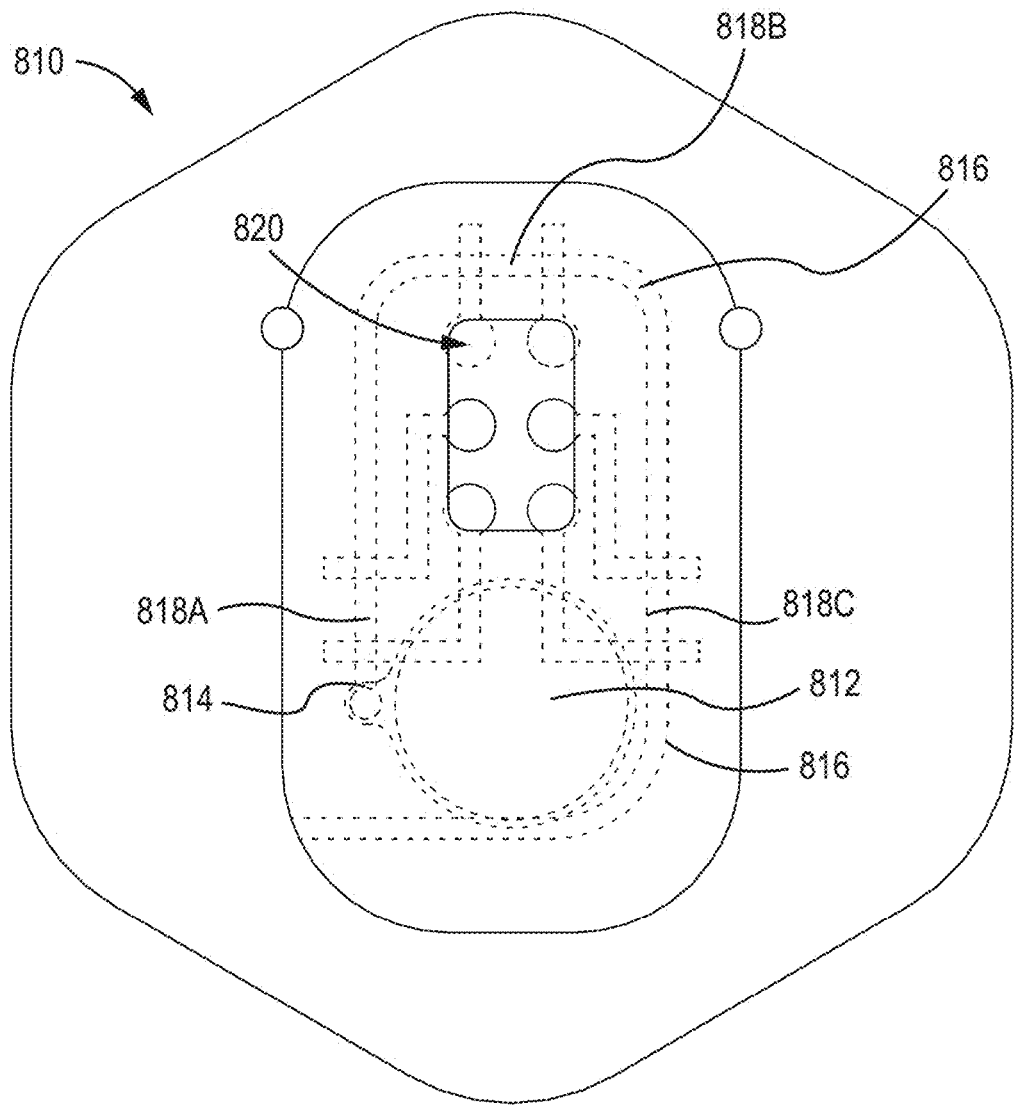
FIG. 26A is a schematic illustration of a top view of a sample handling device that can be used with an example SA system, according to an embodiment.

FIG. 26A is a schematic illustration of a top view of a sample handling device 810, with the layers being rendered transparent to show underlying features, according to an embodiment. The sample handling device 810 can be substantially similar in structure and/or function to the sample handling devices, 110, 210, 310, 510, and/or 710 described herein. For example, the sample handling device 810 can include a sample collection region 812, an access port 814, a flow channel 816, a test region 818, and a set of electrodes 820 that can be substantially similar to that described with reference to the sample handling devices described above. In some embodiments, the sample handling device 810 can include a temperature sensor (not shown). In some embodiments, the temperature sensor can be included in the sample processing device to be coupled to the sample handling device 810.

The sample handling device 810 can be constructed similar to the sample handling devices 210, 310, and/or the sample handling device 710. For example, the sample handling device 810 includes an interface layer 811 which can be a release liner, an adhesive layer 813 configured to be released and adhered to the skin of a user. The adhesive layer 813 includes an opening 822 of the sample collection region 812. The sample handling device 810 includes an access port layer defining the access port 814 and an electrode and channel layer 817 as described with reference to the sample handling devices 210, 310, and/or 710. In some embodiments, the access port layer can be combined with the electrode and channel layer to form an intermediate layer 817. Accordingly, such similar portions and/or aspects are not described in further detail herein.

One or more layers of the sample handling device 810 can include alignment aids such as the alignment apertures 837.

Figure 26B:
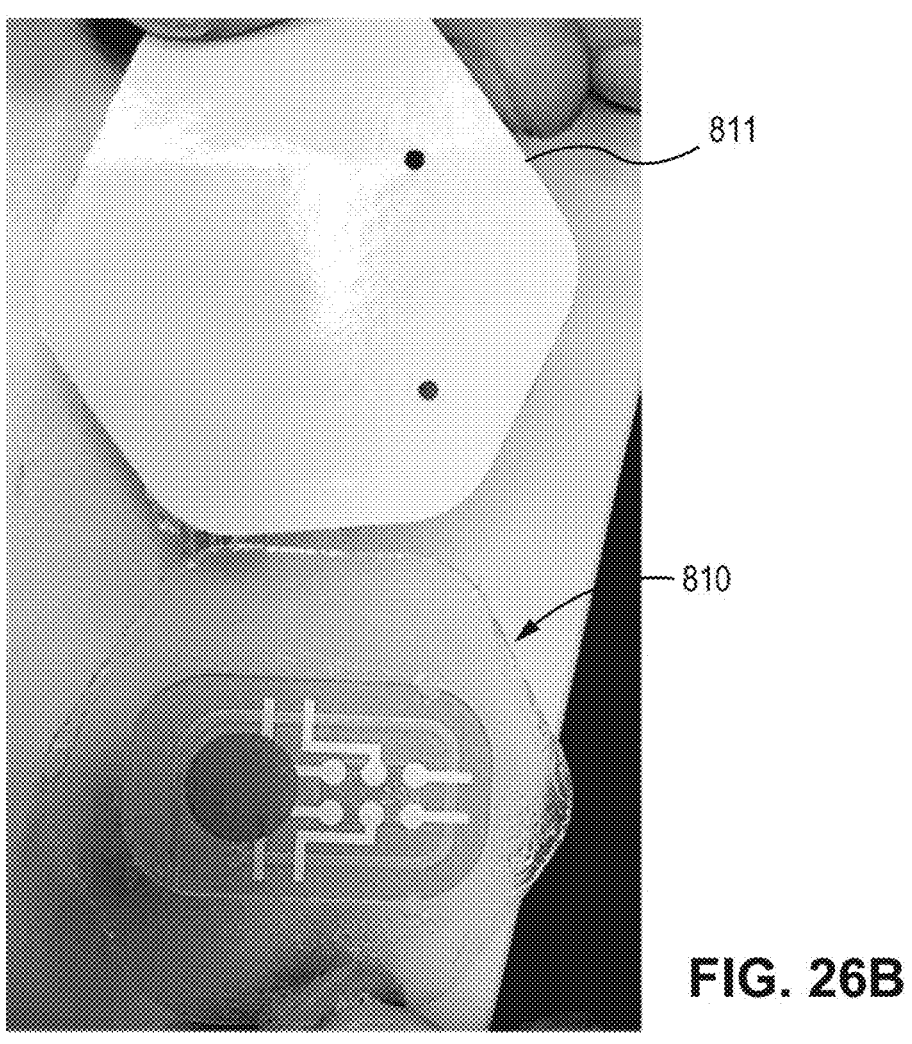
FIG. 26B is a bottom view image of the sample handling device of FIG. 26A, after removing an interface layer, according to an implementation.
Figure 26C:
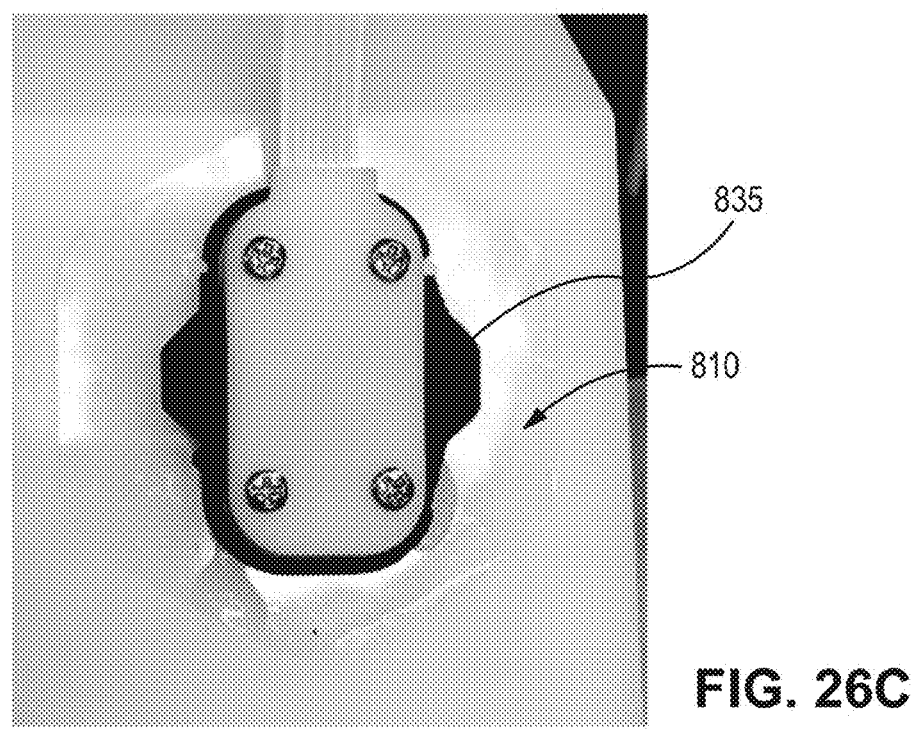
FIG. 26C is a top view image of the sample handling device of FIG. 26A, mounted on a snap ring interface, according to an implementation.
Figures 27A, 27B:
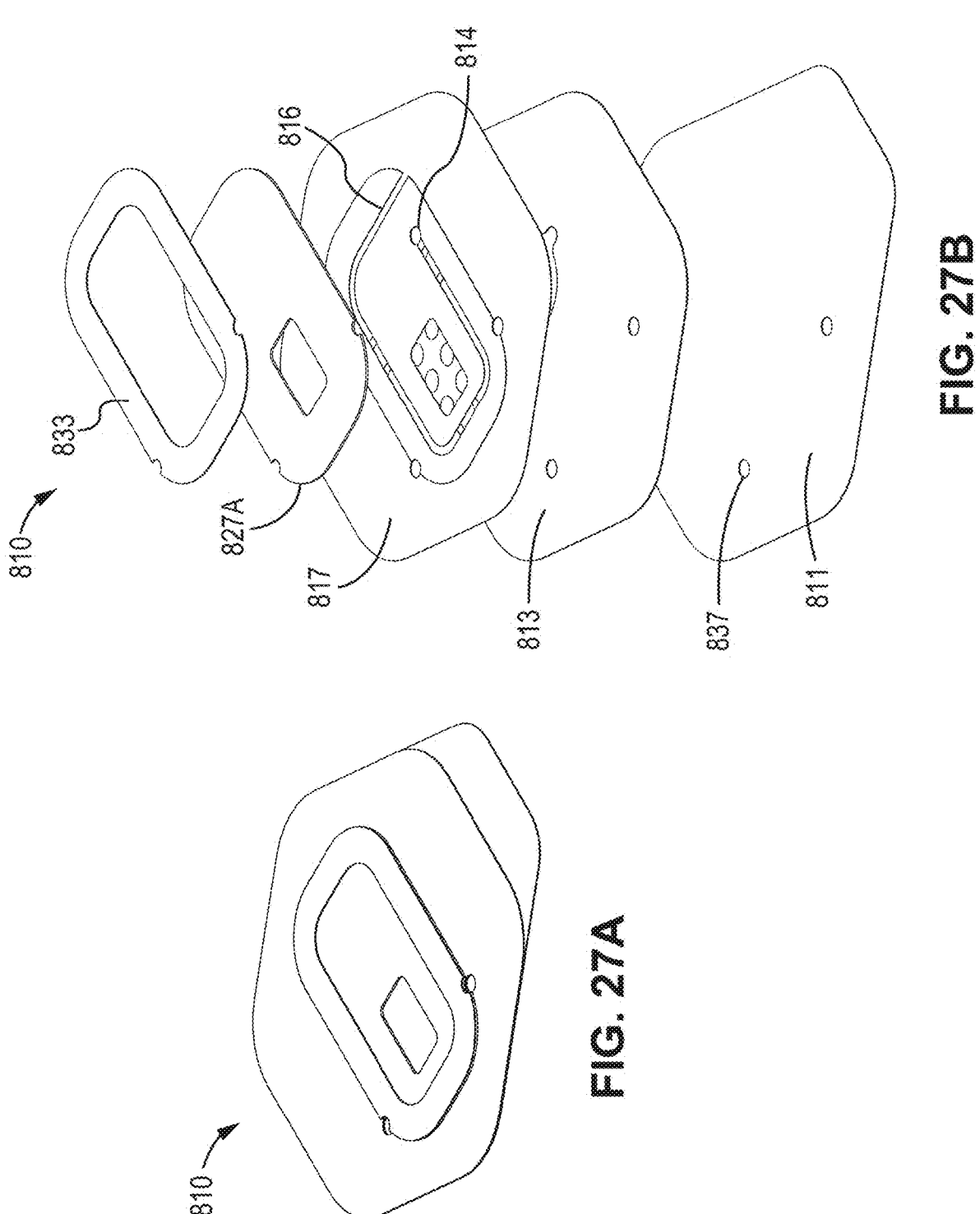
FIG. 27A is a schematic illustration of a perspective side view of the sample handling device of FIG. 26A.
FIG. 27B is a schematic illustration of an exploded view of the sample handling device of FIG. 26A, illustrating the component layers of the sample handing device, according to an implementation.
Figure 28:
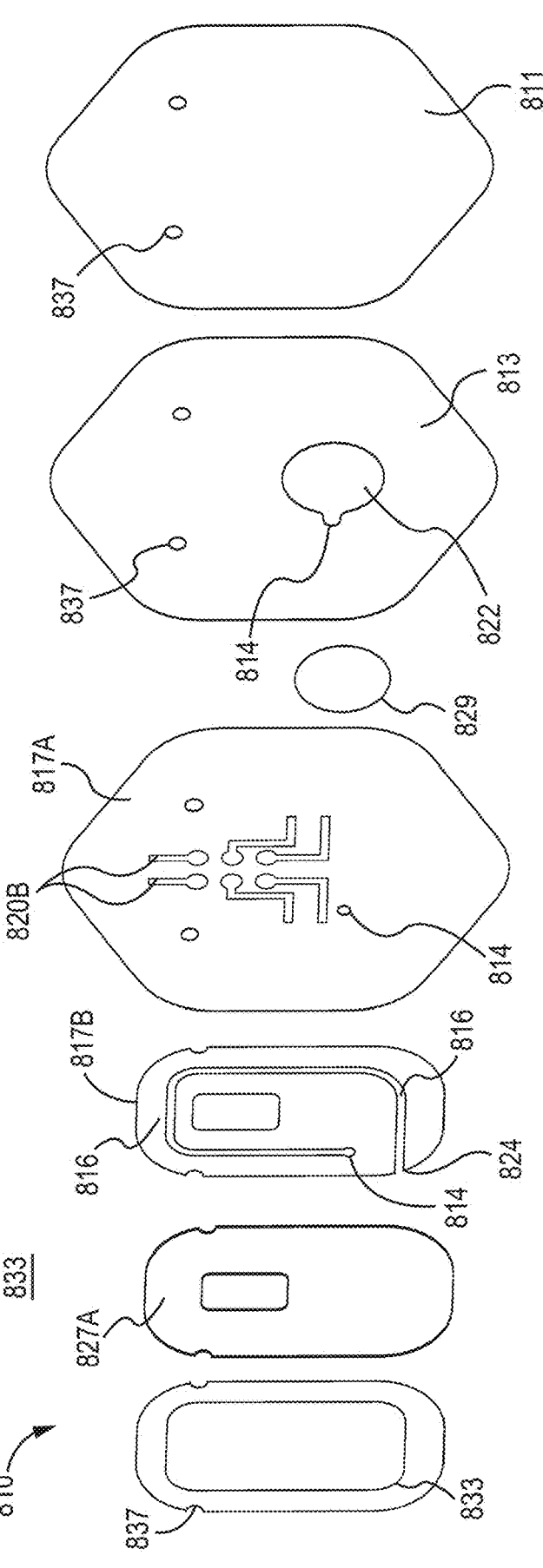
FIG. 28 is a schematic illustration of an exploded view of the sample handling device of FIG. 26A, illustrating the component layers of the sample handing device, according to an implementation.
Figure 29A:
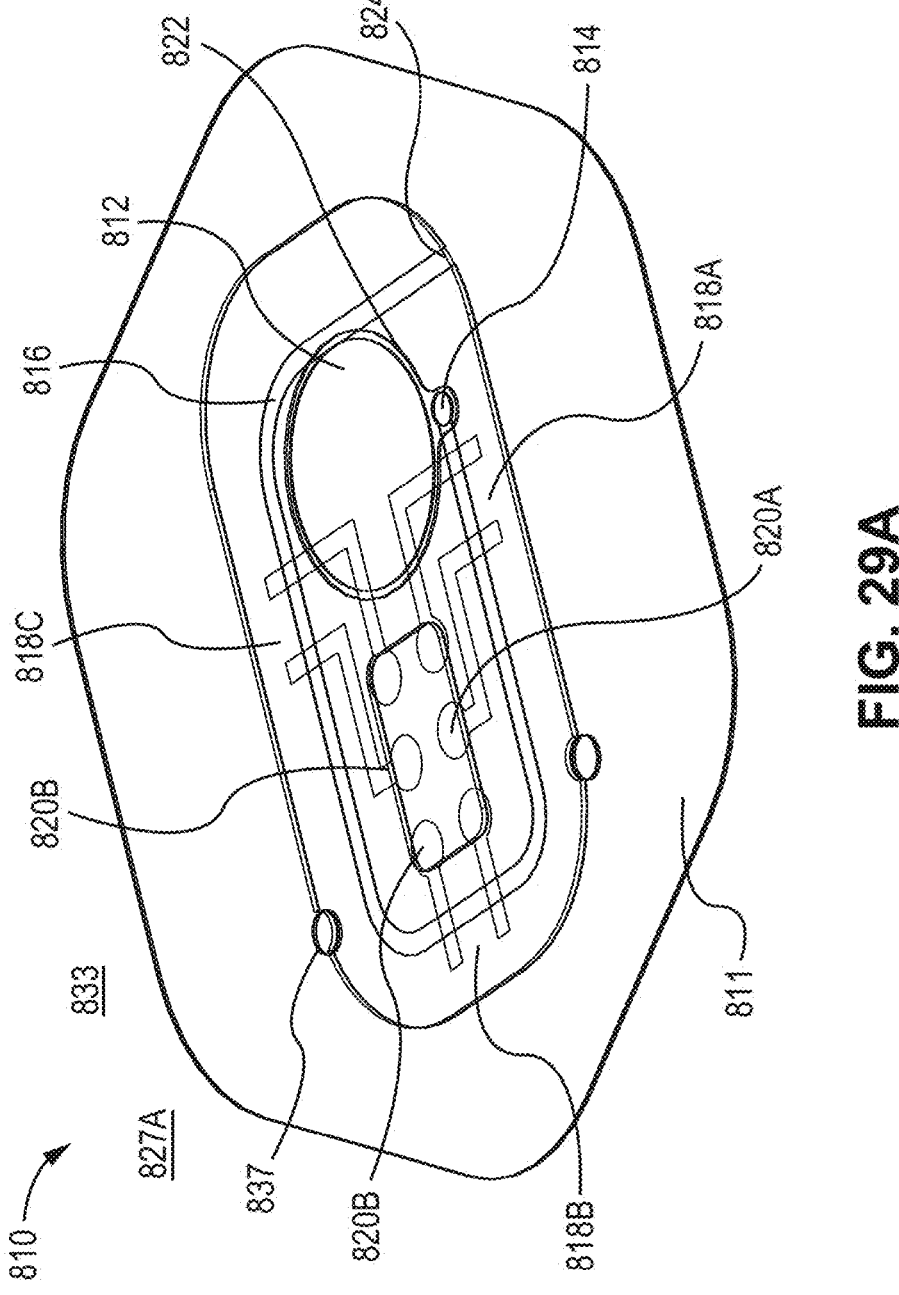
FIG. 29A is a schematic diagram of a perspective top view of the sample handling device of FIG. 26A, with the layers rendered transparent to show overlying features, according to an implementation.

FIG. 26B and is a schematic illustrations of a bottom view of a sample handling device 810, after removing the release liner forming the interface layer 811. FIG. 26C illustrates a top view of the sample handling device 810 mounted on a mounting interface 835 (e.g., a snap ring interface), according to an embodiment. FIG. 27A is a perspective top view of an example embodiment of the sample handling device 810 of FIG. 26A-26C. FIG. 27B is a schematic illustration of an exploded view of the sample handling device 810 of FIG. 27A, according to an example implementation. FIG. 28 is a schematic illustration of an exploded view of the sample handling device 810, according to an embodiment. FIG. 29 shows a perspective top view of the device 810. FIG. 30 shows an exploded view of the sample handling device 810 mounted onto mounting structures, according to one implementation.

The interface layer 811 and/or the adhesive layer 813 can be substantially similar to the interface layers and/or the adhesive layers described herein (e.g., interface layers 211, 711, etc. and adhesive layers 213, 713, etc.). In some embodiments, the access port 814 can be formed at a suitably defined location on the access port layer 817 and with respect to the sample collection region 812 and its opening 822 as shown in FIGS. 26 and 29. For example the access port 814 can be positioned at an off center location with respect to the opening 822 of the sample collection region 812 to reduce and/or prevent formation of air bubbles in the collected sample of bodily fluid. The opening 822 can be suitably shaped to accommodate the off-center positioning of the access port 814 as shown by the notch in FIGS. 26 and 29.

In some embodiments, the intermediate layer 817 defines the access port 814, defined as a through opening, and includes the flow channel defined on a distal surface and the electrode tracks and test regions defined on a proximal surface. In some embodiments, the intermediate layer 817 can be made from a suitable material such as polyester (PET), PDMS, and/or the like. In some embodiments, the intermediate layer 817 can be made from a suitably coated material such that one or both surfaces has hydrophilic properties. For example, the intermediate layer 817 can be made from Coveme® (e.g., Coveme® 0.100 mm (4 mil) HNW), which includes one surface with a hydrophilic coating. The hydrophilic coating can improve wicking of fluids ad to direct the flow of bodily through the defined flow channel 816 during use. In some embodiments, the hydrophilic coating can be applied on the proximal surface and the electrode layer 817A can be printed on the hydrophilic surface. In some embodiments, the hydrophilic coating can be added on any surface or portion of surface that contacts with fluid. The hydrophilic coating can be configured to reduce bubble formation and/or improve the flushing of any bubbles that do get into the system.

In some embodiments, the hydrophilic coating can be applied on the distal surface and the channel layer 817B can be printed on the hydrophilic surface. The hydrophilic coating can be applied in any suitable shape. For example, in some implementations the hydrophilic coating can be applied preferentially to the portions defining an inner surface of the flow channel 816 to aid in flow of the sample of bodily fluid.

The sample handling device 810 can include three test regions 818A, 818B, and 818C, as shown in FIGS. 26A and 29. Each test region includes a set of electrodes 820A, 820B and 820C respectively. The test regions 818A, 818B, and 818C are positioned at increasing distances from the access port 814 and along the flow path 816 before the sample of bodily fluid is ejected at 824. The sample handling device 810 can include a stiffener layer 827A configured to provide structural support to a portion of the electrode and channel layer 817, for example, the stiffener layer 827A can be configured to provide a wall of the flow path 816 and a support to a cell portion overlying regions including the access port 814, the test regions 818A, 818B, 818C, etc.

The electrode layer 817A can include a set of electrodes 820A, 820B, and 820C and electrode tracks connecting the electrodes to terminal ends. In some embodiments, the set of electrodes 820 can be configured such that each test region is allocated one or more excitation electrode to apply an excitation signal and one or more sensing electrodes to receive a response signal from the sample of fluid being tested. In some embodiments, the electrodes 820 can be configured such that each test region is equipped with a bipolar electrode to excite and sense responses from a sample bodily fluid being tested. The electrodes 820 and the electrodes tracks can be printed using any suitable conductive and/or electrode ink. For example, the electrodes and/or electrode tracks can be printed using Ercon (80/20 Silver/Silver Chloride ink) or any other electrode material, with any suitable thickness (e.g., 0.015 mm). The terminal ends of the electrodes can be any suitable configuration to be electrically connected to a portion of a sample processing device. For example, the terminal ends can be configured to be connected via pogo pins, spring-loaded pins and/or the like.

In some embodiments, the flow channel 816 can be defined by a loop shape as shown in FIG. 26A to reduce and/or prevent air ingress. The channel layer 817B can be formed by printing thickening ink at predefined regions to form the flow path 816. For example, the channel layer 817B can be formed by printing 0.05 mm thickness of NAZDAR NFX52 ink. The flow path 816 can be formed collectively upon the assembly of the intermediate layer 817 and the stiffener layer 827A, with the stiffener layer 827A forming a distal wall of the flow path 816. The channel layer 817B can include test regions 818A, 818B, and 818C defined at specified portions along the flow path 816. The test regions 818A, 818B, and 818C and the flow path 816 can be defined on the distal surface of the intermediate layer 817 and the electrode tracks and the sample ends of the electrodes 820A, 820B and 820C can be defined on the proximal side of the intermediate layer. The test regions can be configured to include one or more through holes providing electrical connectivity between the distal surface of the intermediate layer 817 defining the flow path 816, and the proximal surface of the intermediate layer 817 defining the electrodes, such that while a sample of bodily fluid flows though the flow path 816 and flows through each of the test regions an excitation signal applied by the excitation electrode can be delivered to the sample of fluid at the test region and can elicit a response from the sample of bodily fluid which can be sensed by the sensing electrode located at that test region. In some embodiments, the temperature sensor can be configured to be house in the sample processing device and measure the temperature of the sample of fluid being tested at one or more of the test regions defined on the channel layer 817B.

Figures 29B, 29C, 29D, 29E:
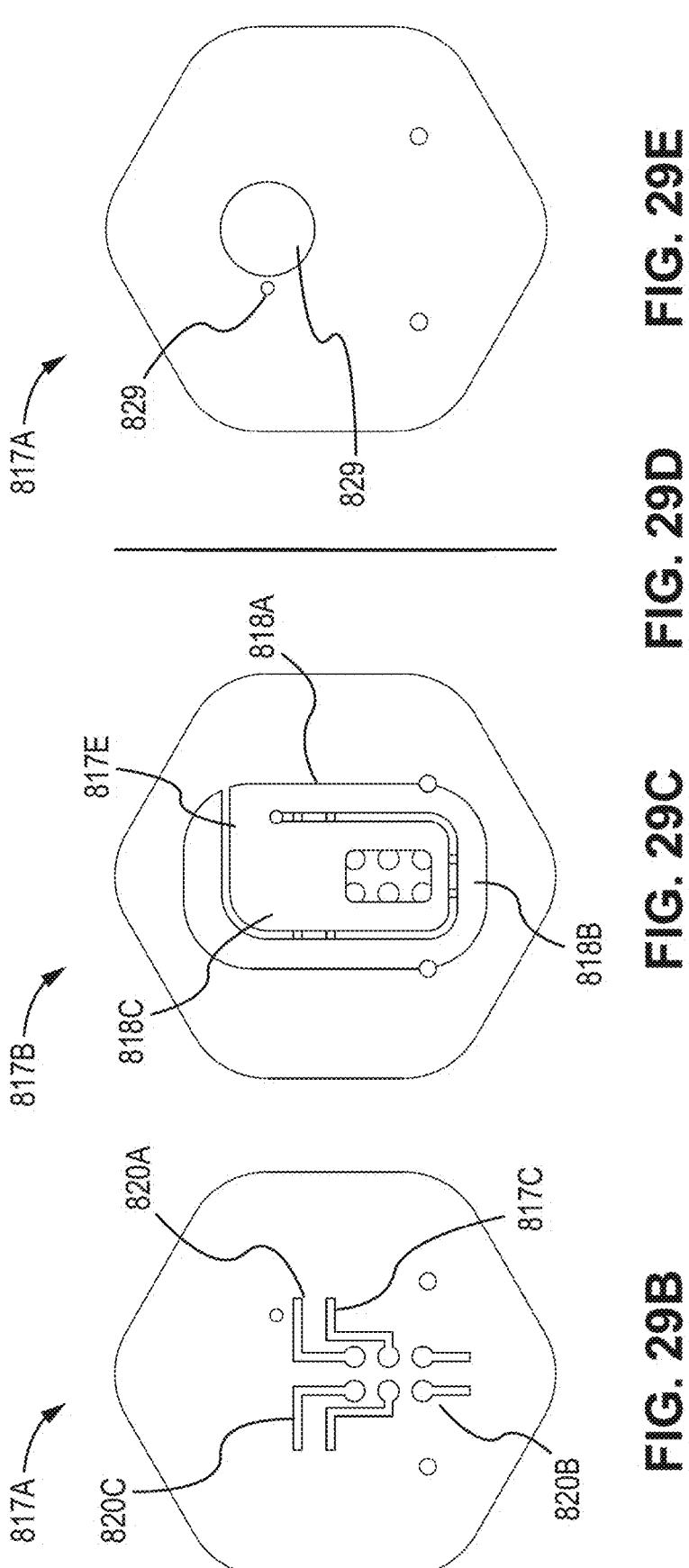
FIG. 29B-29E are schematic illustrations of a top view of an electrode layer with the channel layer removed, a top view of a channel layer, a side view of the channel layer, and a bottom view including a spacer portion of an electrode layer of the sample handling device of FIG. 26A, according to an implementation.
Figure 30:
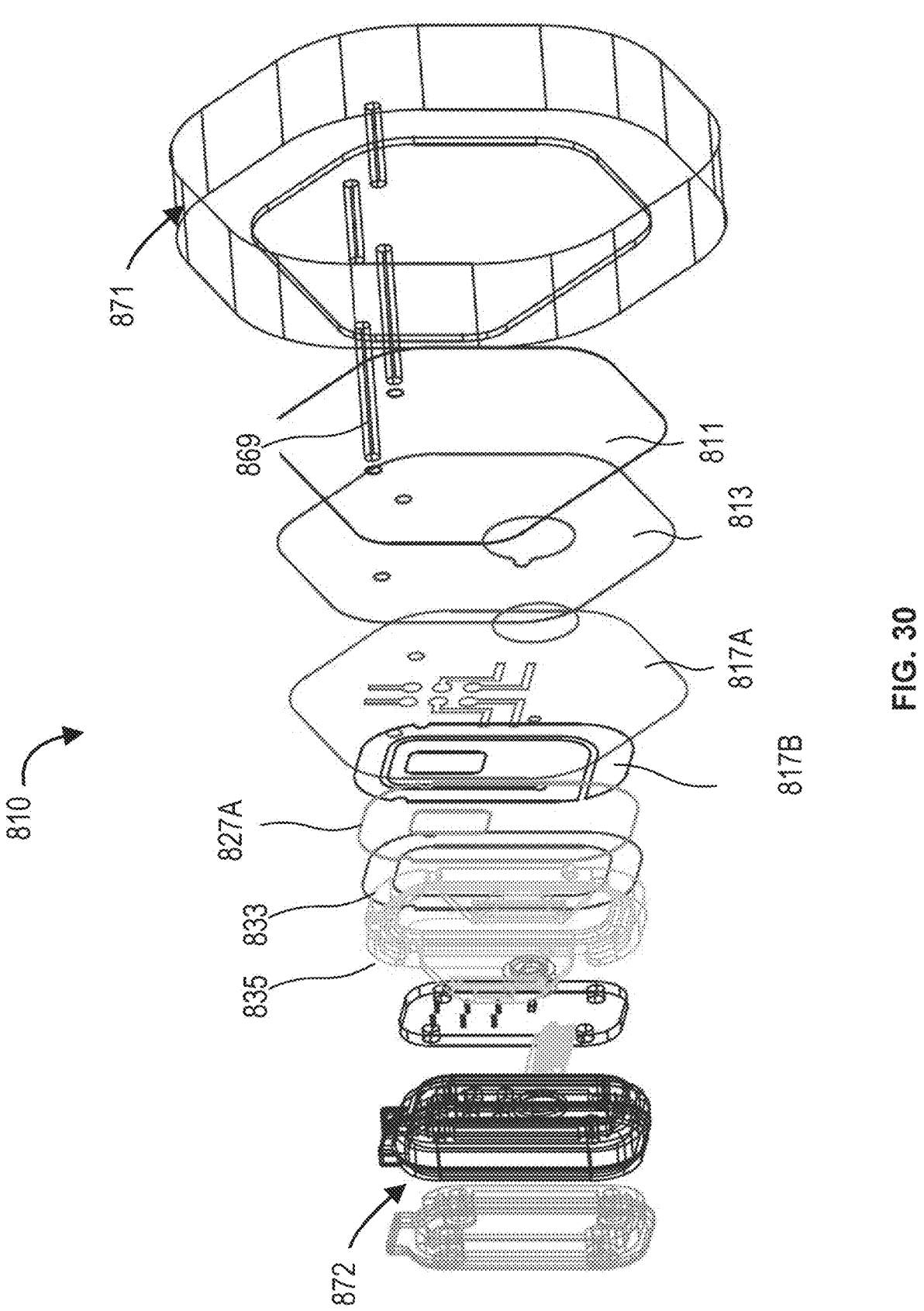
FIG. 30 is a schematic diagram of an exploded view of the sample handling device of FIG. 26A, coupled to assembly fixtures, according to an implementation.

FIG. 29B is a schematic illustration of a top view with the channel layer removed and showing the proximal side of the intermediate layer 817 including the electrode layer 817A. FIG. 29C illustrates a top or a distal side of the intermediate layer 817 including the channel layer 817B. FIG. 29D is a side view and FIG. 29E shows a bottom view of the spacer portion 829 to be overlaid on the proximal surface of the intermediate layer 817 including the electrode layer 817A.

In some implementations, the sample handling device 810 can include a spacer portion 829 incorporated to occupy space in the sample collection region 812 as described previously with reference to spacer portion 729. The spacer regions 829 can be formed by printing thickening ink (e.g., 0.10 mm NAZDAR NFX52). The device 810 can include additional adhesive layer 833, in some implementations, to aid with adhering to an alignment and/or mounting interface (e.g., a snap ring interface).

FIG. 30 illustrates an exploded view of the sample handling device 810 mounted onto a snap ring interface 835, and a set of assembly fixtures 871 using alignment structures 869 interfaced with the alignment aids, according to an example implementation. FIG. 30 also illustrates electrical interface assembly 872 that can be used, in some implementations, to test and/or optimize the function of the sample handling device 810.

Figures 31, 32:
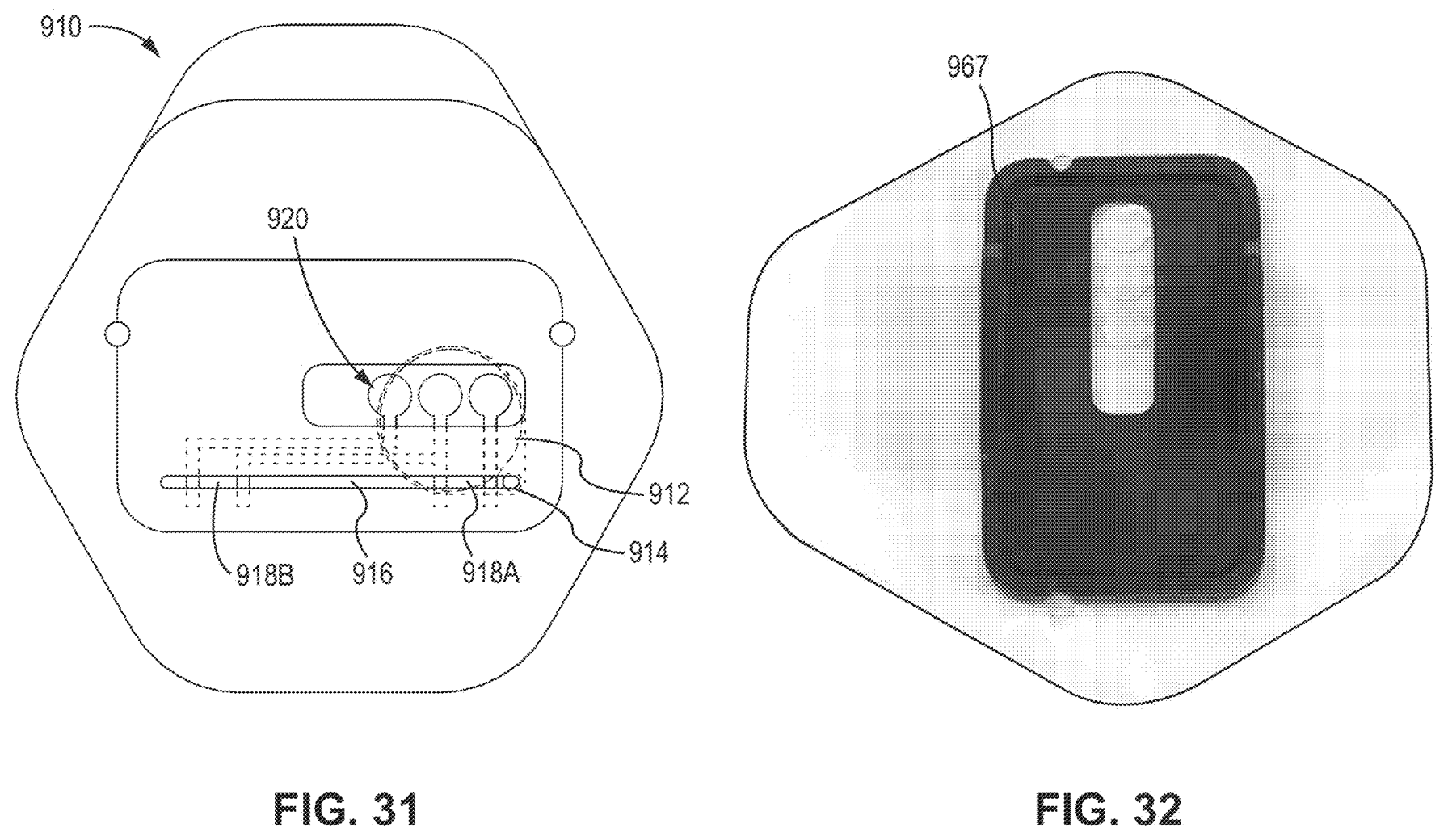
Figure 33B:
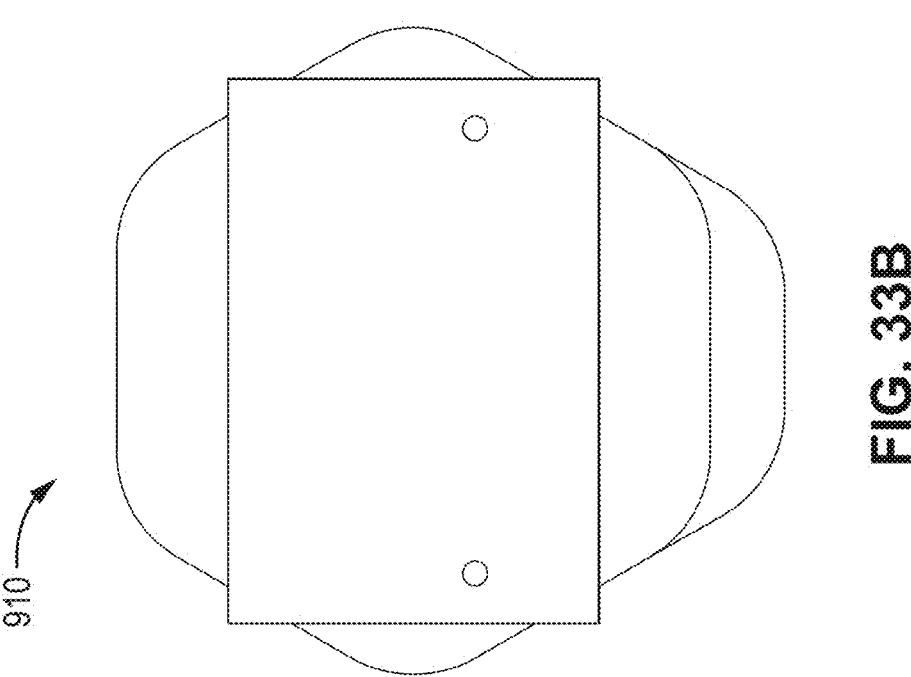
FIGS. 33A and 33B are schematic illustrations of a perspective top view and a top view of the sample handling device of FIG. 31, including liner layers for packaging, according to an implementation.
Figure 33A:
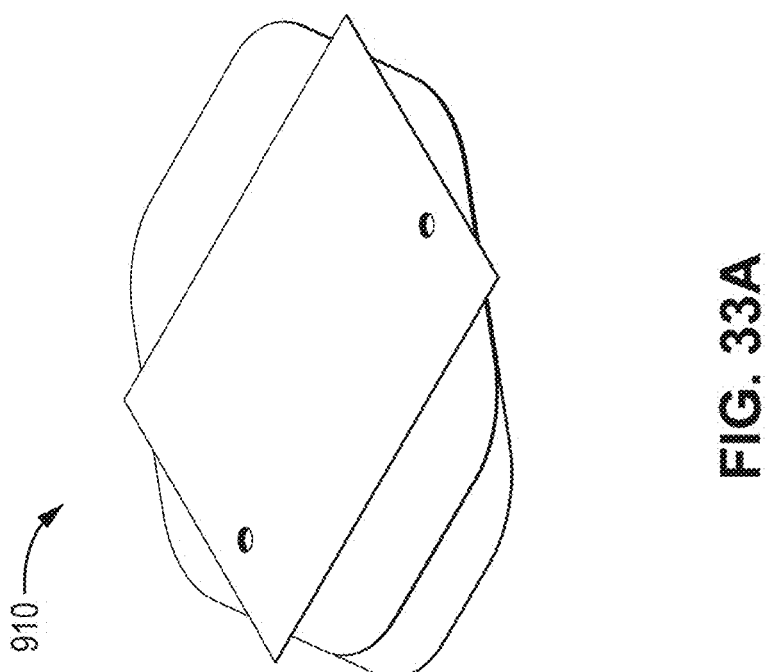

FIG. 31 is a schematic illustration of a top view of a sample handling device 910, with the layers being rendered transparent to show underlying features, according to an embodiment. FIG. 32 is a schematic illustration of a top view of the sample handling device 910 mounted onto an interface 967 (e.g., a snap ring interface), in an example implementation. The sample handling device 910 can be substantially similar in structure and/or function to the sample handling devices, 110, 210, 310, 510, 710, and/or 810 described herein. For example, the sample handling device 910 can include a sample collection region 912, an access port 914, a flow channel 916, a test regions 918A and 918B, and a set of electrodes 920 that can be substantially similar in structure and/or function to that described with reference to the sample handling devices described above. In some embodiments, the sample handling device 910 can include a temperature sensor (not shown). In some embodiments the temperature sensor can be included in the sample processing device to be coupled with the sample handling device 910, and the temperature sensor can be configured such that a temperature of the sample fluid being tested at the one or more test regions 918 can be measured. FIGS. 33A and 33B are schematic illustrations of the sample handling device 910 from a perspective top view and a top view, shown with layers used for packaging, according to one implementation.

Figure 34:
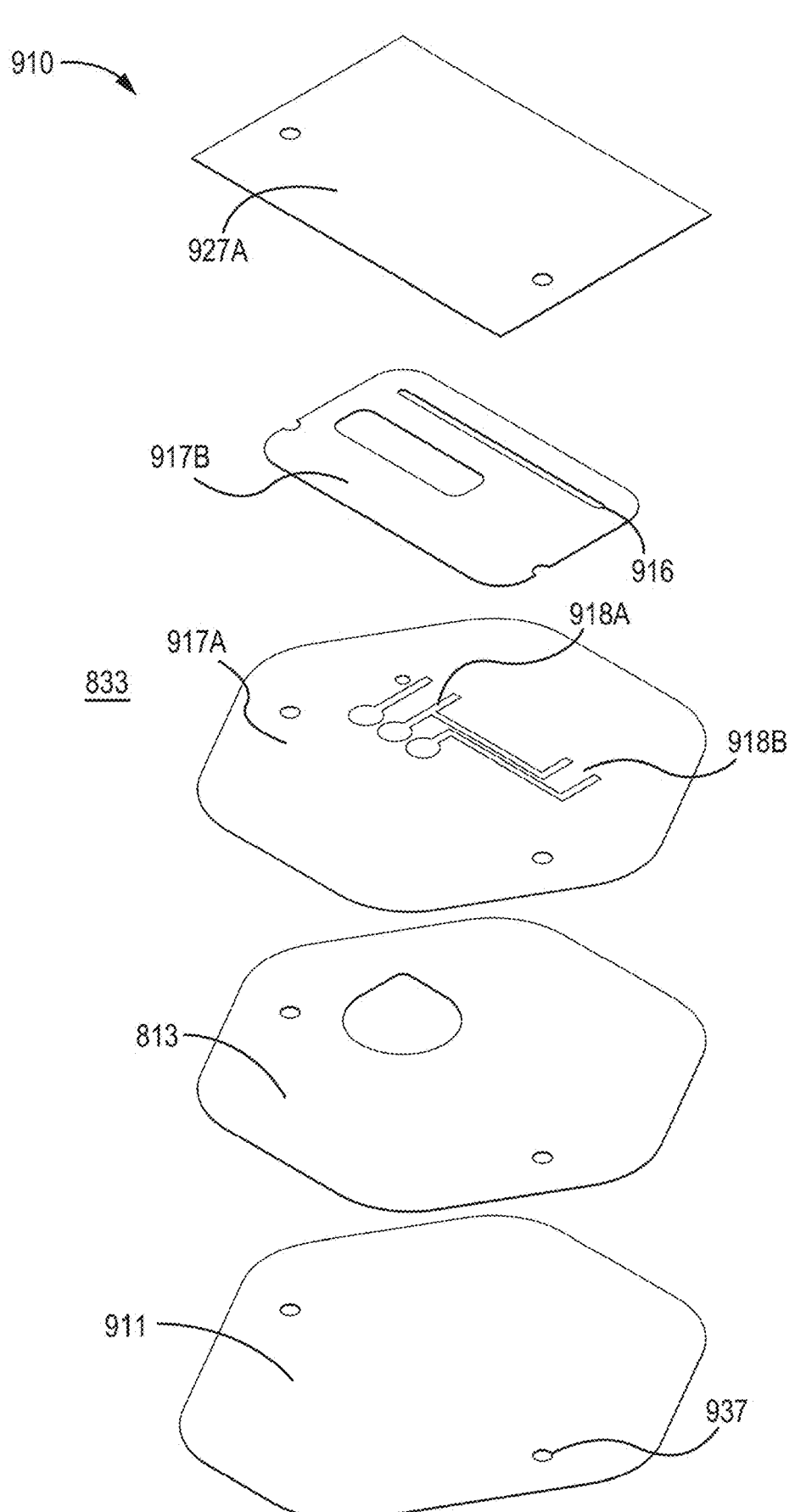
FIG. 34 is a schematic diagram of an exploded view of the sample handling device of FIG. 31, coupled to mounting interfaces, according to an implementation.
Figures 35A, 35B:
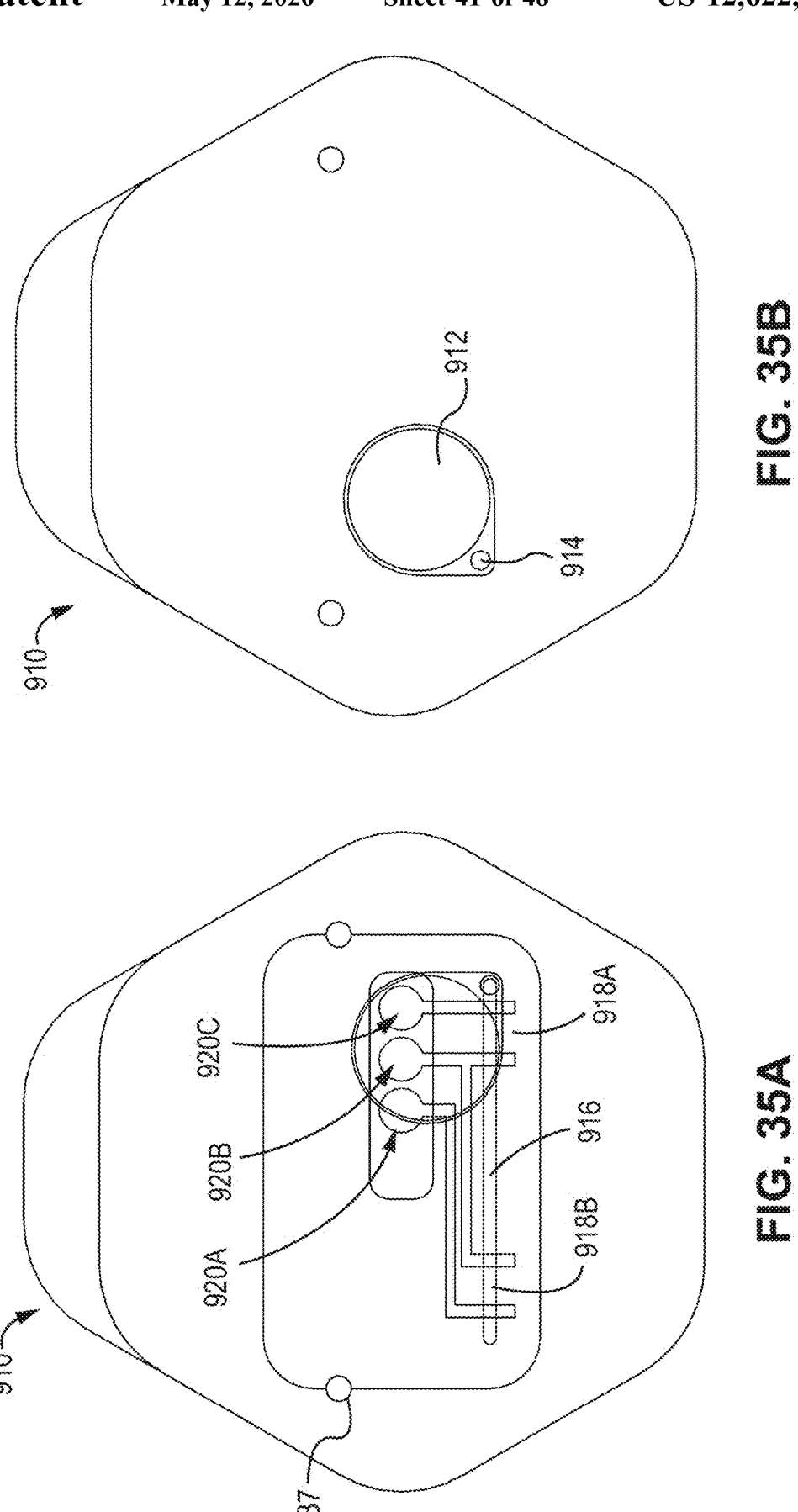
FIGS. 35A and 35B are schematic illustrations of a top view and a bottom view of the sample handling device of FIG. 31, respectively, according to an implementation.
Figure 37:
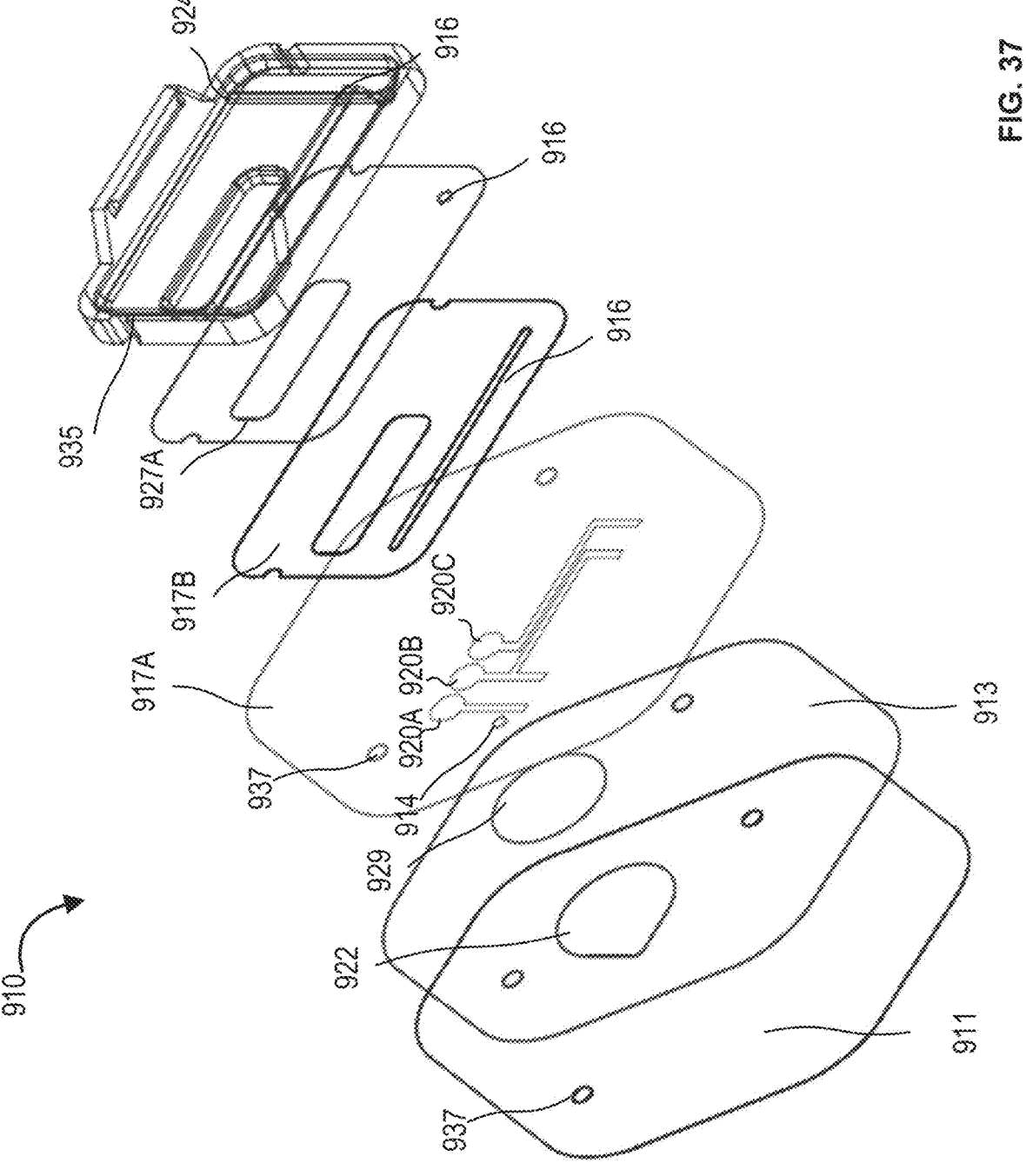
FIG. 37 is a schematic illustration of a perspective side exploded view of the sample handling device of FIGS. 35A and 35B mounted on a snap ring interface, illustrating the component layers of the sample handing device, according to an implementation.
Figure 38:
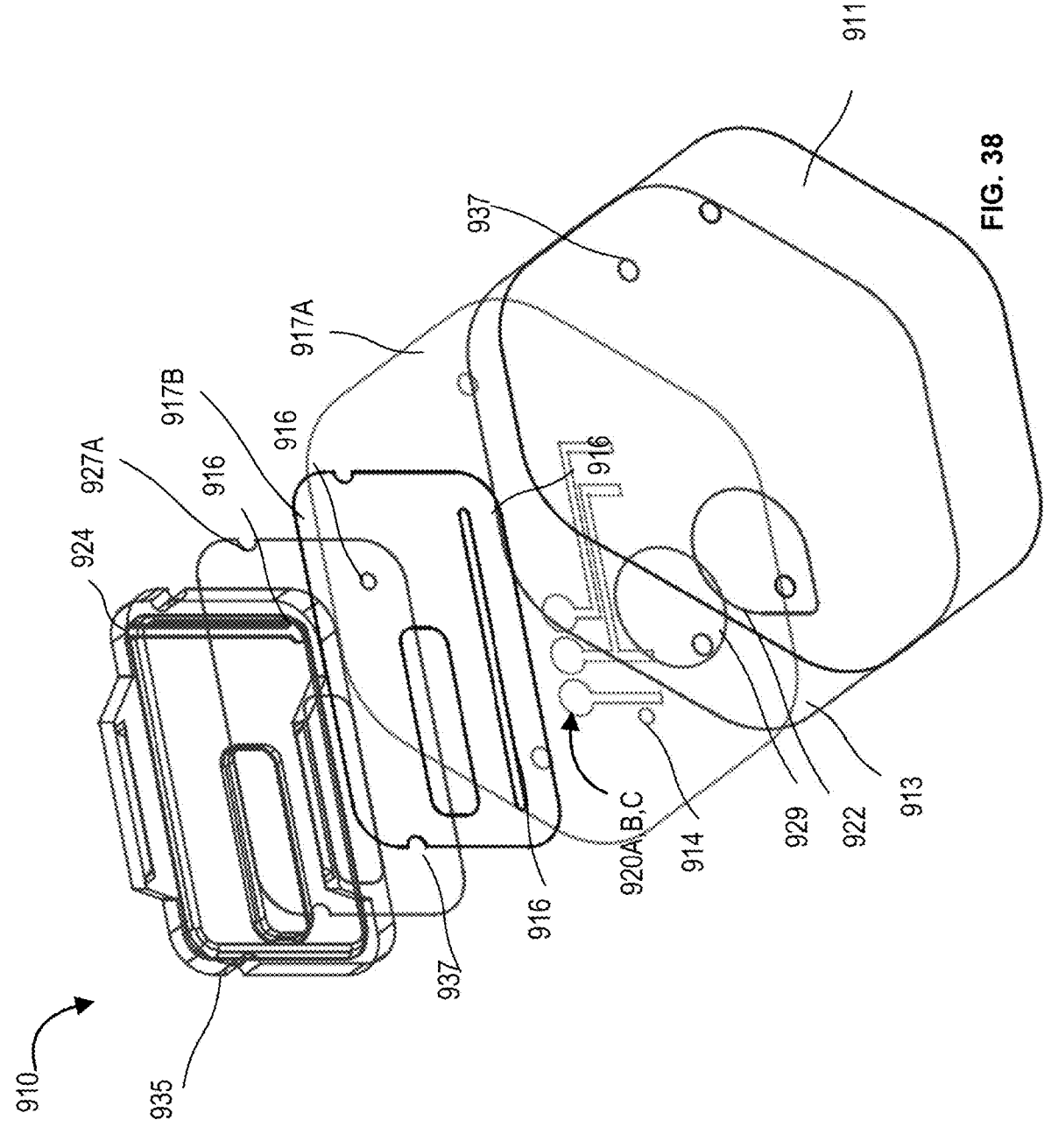
FIG. 38 is a schematic illustration of a perspective exploded side view of the sample handling device of FIGS. 35A and 35B mounted on a snap ring interface, illustrating the component layers of the sample handing device, according to an implementation.

FIG. 34 is a schematic illustration of an exploded view of the sample handling device 910 of FIG. 33A. 33B, according to one implementation. FIGS. 35A and 35B are schematic illustrations of a bottom view and a top view of the sample handling device 910, according to one embodiment. FIGS. 36 and 37 are exploded views from two perspectives of the sample handling device 910 mounted onto mounting structures, according to one implementation. FIG. 38 is an exploded view of the sample handling device 910 mounted onto mounting structures, according to another implementation.

In some implementations, the sample handling device 910 can be constructed similar to the sample handling devices 210, 310.710, and/or the sample handling device 810. For example, the sample handling device 910 includes an interface layer 911 which can be a release liner, and an adhesive layer 913 configured to be released and adhered to the skin of a user. The adhesive layer 913 includes an opening 922 of the sample collection region 912. The sample handling device 910 includes an access port layer defining the access port 914 combined with the electrode and channel layer 817 as described with reference to the sample handling devices 210, 310, 710, and/or 810. Accordingly, such similar portions and/or aspects are not described in further detail herein.

One or more layers of the sample handling device 910 can include alignment aids 937. The interface layer 911 and/or the adhesive layer 913 can be substantially similar to the interface layers and/or the adhesive layers described herein (e.g., interface layers 211, 711, 811, etc. and adhesive layers 213, 713, 813, etc.). In some embodiments, the access port 914 can be formed at a suitably defined location on the electrode layer 917A (also serving as the access port layer) and with respect to the opening 922 of the sample collection region 812 as shown in FIGS. 35A and 35B. For example the access port 914 can be positioned at an off center location with respect to the opening 922 of the sample collection region 912 to reduce, flush, and/or prevent formation of air bubbles in the collected sample of bodily fluid and/or to prime the flow of bodily fluid during use.

In some embodiments, an electrode layer 917A defines the access port 914, defined as a through opening. In some embodiments, the electrode layer 917A can be made from a suitable material such as clear polyester (PET). PDMS, and/or the like. In some embodiments, the intermediate layer 817 can be made from a suitably coated material such that one or both surfaces has hydrophilic properties. For example, the electrode layer 917A can be made from Coveme® (e.g., Coveme® 0.100 mm (4 mil) HNW), which includes one surface with a hydrophilic coating. The hydrophilic coating can improve wicking of fluids and/or flushing of bubbles and to direct the flow of bodily through the defined flow channel 916 during use. The electrode tracks and test regions can be defined on the proximal surface of the electrode layer 917A. The hydrophilic coating can be applied on the proximal surface and the electrode layer 917A can be printed on the hydrophilic surface.

The sample handling device 910 can include a channel layer 917B that is of a precise predefined thickness and determines a cross sectional size and volume of a portion of the flow channel 916. In some embodiments, the channel layer 917B can include an adhesive surface that can be configured to attach to a portion of a sample processing device (e.g., sample processing device 130, 330, etc.). In some implementations, the sample handling device 910 can be a disposable portion to be used with a durable portion with the adhesive surface of channel layer 917B used to attached the sample handling device 910 to the durable portion (e.g., attached to a plastic portion). In some implementations, the sample handling device 910 can be used with and attached to a plastic portion or surface of a disposable sample processing device through the adhesive surface of channel layer 917B. In some embodiments, the adhesive surface of the channel layer 917B can be configured to attach to a stiffener layer 927A. The stiffener layer 927A can be made of any suitable plastic material. In some embodiments, the flow channel 916 can be defined by a linear portion in the channel layer 917B which extends via a through hole in the stiffener layer 927A and via a flow path defined by an interface (e.g., a snap ring interface 924 shown in FIGS. 37 and 38. The outlet 924 can be defined in the snap ring interface 935 to eject the tested sample of fluid. The flow path 916 can be formed collectively upon the assembly of the adhesive layer 912 the electrode layer 917A, the channel layer 917B, the stiffener layer 927A, and the snap interface 935. The channel layer 917B can include the test regions 918A, and 918B defined at specified portions along the flow path 816. The electrode tracks and the sample ends of the electrodes 920A, 920B and 920C can be defined on the proximal side of the electrode layer 917A and the test regions 918A, and 918B, and the flow path 916 can be defined on the distal surface of the electrode layer 917A and the channel layer 917B such that as a sample of bodily fluid flows though the flow path 916 and flows through each of the test regions an excitation signal applied by the excitation electrode 920B can be delivered to the sample of fluid at the test region and can elicit a response from the sample of bodily fluid which can be sensed by the sensing electrode 920A, 920C located at that test region 918A. 918B, respectively. In some embodiments, a temperature sensor can be configured to be housed in the sample processing device and to measure the temperature of the sample of fluid being tested at one or more of the test regions 918A and 918B defined on the channel layer 917B.

In some embodiments of the sample handling device, the electrodes 920 can be configured such that multiple electrode pairs can share one or more electrodes. The multiple electrode pairs can be directed to multiple test regions such that the shared electrode can have a common terminal end and multiple sample ends that are located at or near the multiple test regions. For example, the electrodes 920 can be configured such that two or more electrode pairs share an excitation electrode instead of one excitation electrode per pair of electrodes. The sample handling device 910 can include two test regions 918A, and 918B, at predefined, as shown in FIG. 35A. The test region 918A includes a set of electrodes 920A, and 920B and the test region 918B includes the electrodes 920B and 920C respectively, with electrode 920B serving both test regions. The test regions 918A, and 918B, are positioned at increasing distances from the access port 914 and at a known distance between each other along the flow path 916 before the sample of bodily fluid is ejected at 924. The sample handling device 910 can include the stiffener layer 927A configured to form a distal wall of the flow path 916 (away from the body of the user when in use) with the distal surface of the electrode layer 917A forming the proximal wall of the flow path 916. The stiffener layer 927A is also configured to provide structural support to a portion of the electrode and channel layers 917A and 917B, for example, a cell portion overlying regions including the access port 914, the test regions 918A, and 918B.

In some embodiments, the electrode 920B can be a common excitation electrode serving both test regions 918A and 918B, and the electrodes 920A and 920C can be configured to be sensing electrodes operating in combination with the electrode 920B. Excitation signals can be applied via electrode 920B and electrodes 920A and 920C can receive a response signal from the sample of fluid being tested at each test region. In some embodiments, the electrodes can be configured to operate as bipolar electrodes to excite and sense responses from a sample bodily fluid being tested. The electrodes 920A, 920B, and 920C and the electrodes tracks can be printed using any suitable conductive and/or electrode ink. For example, the electrodes and/or electrode tracks can be printed using Ercon (80/20 Silver/ Silver Chloride ink) or any other electrode material for any suitable thickness. The terminal ends of the electrodes can be any suitable configuration to be electrically connected to a portion of a sample processing device. For example, the terminal ends can be configured to be connected via pogo pins, spring-loaded pins and/or the like.

FIG. 36A is a schematic illustration of a top or distal side of the electrode layer 917A. FIG. 36B is a side view and FIG. 36C illustrates a bottom or a proximal side of the electrode layer 917B and shows a bottom view of the spacer portion 929 to be overlaid on the proximal surface of the electrode layer 917A. As shown the channel layer 917B includes a through opening allowing electrical access between a sample processing device attached at the distal side of the sample handling device 910 and the connection points of the electrodes 920A, 920B and 920C on the distal side of the electrode layer 917A.

In some implementations, the sample handling device 910 can include a spacer portion 929 incorporated to occupy space in the sample collection region 912 as described previously with reference to spacer portion 729 and/or 829. The spacer regions 929 can be formed by printing thickening ink (e.g., 100 μm or approximately 0.004" NAZDAR NFX52). The device 910 can include additional adhesive layer (not shown), in some implementations, to aid with adhering to an alignment and/or mounting interface (e.g., a snap ring interface).

Figure 39:
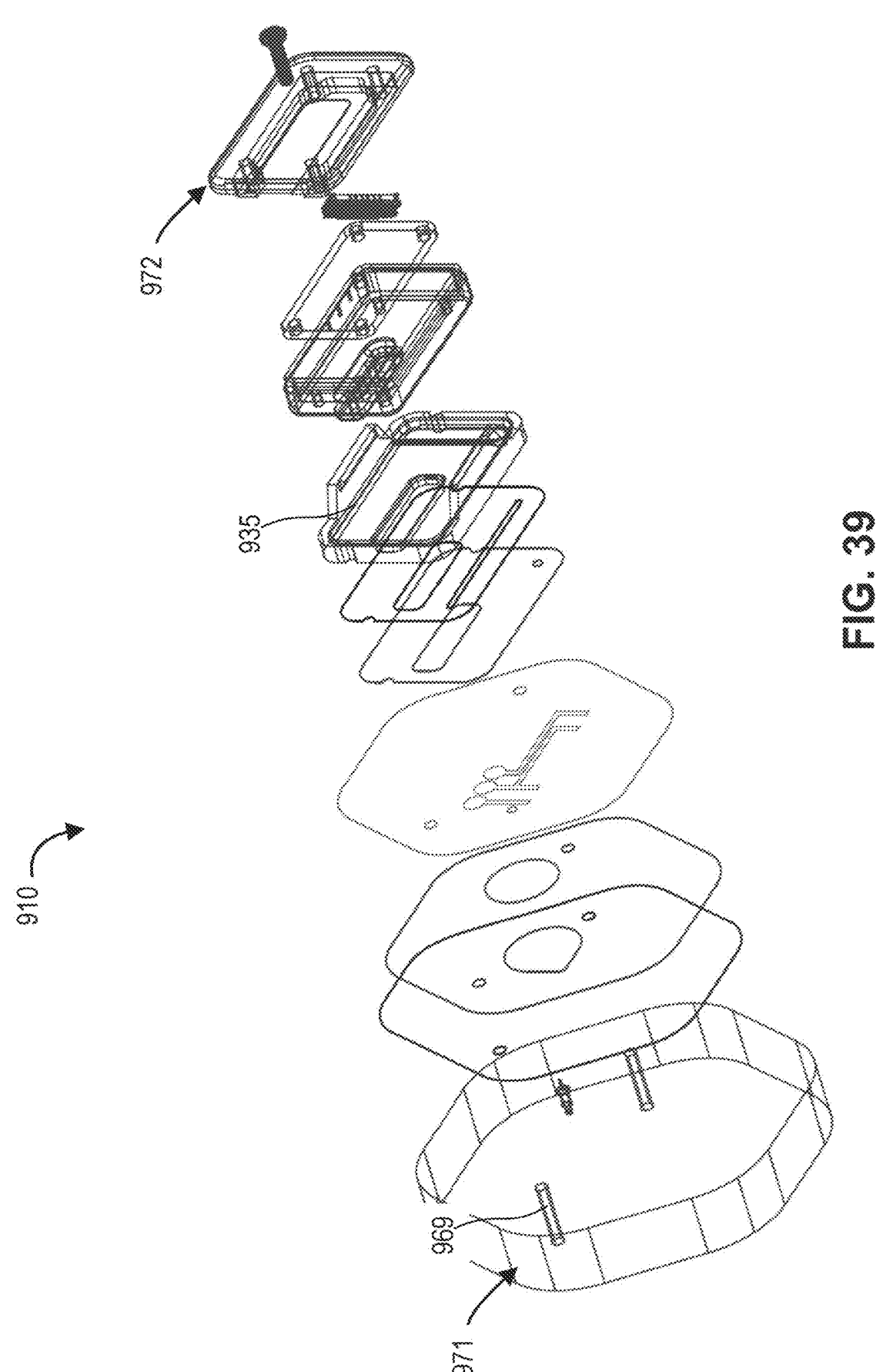
FIG. 39 is a schematic diagram of an exploded view of the sample handling device of FIG. 31, coupled to mounting interfaces, according to an implementation.
Figures 40A, 40B, 40C, 40D:
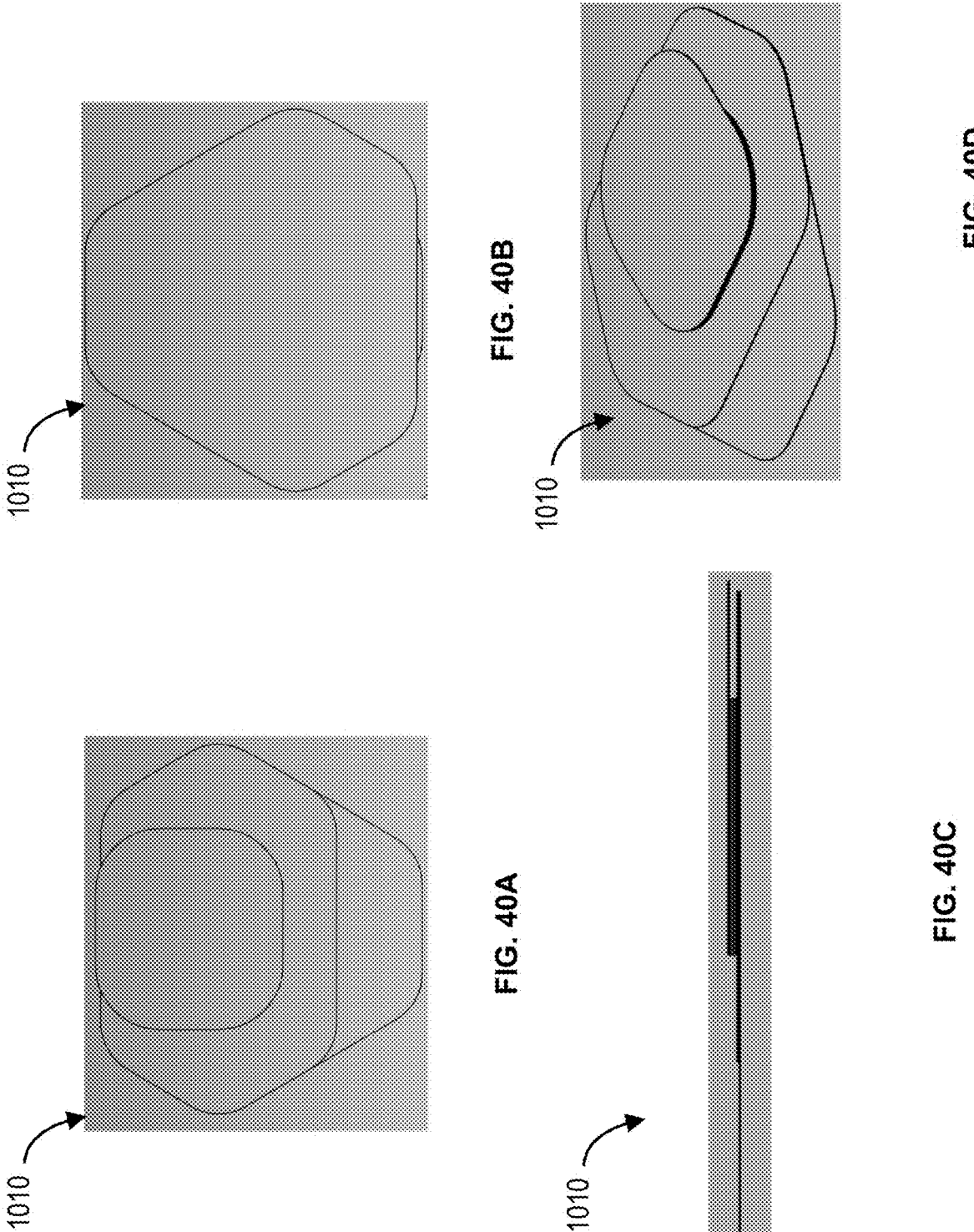
FIGS. 40A-40D are schematic illustrations of a bottom view, top view, side view and a perspective view of a sample handing device, according to an implementation.

FIGS. 37 and 38 illustrates two perspective exploded views of the sample handling device 910 mounted onto a snap ring interface 935, according to one implementation. FIG. 39 shows an exploded view of sample handlingdevicee 910 mounted onto a snap ring interface and set of mounting structures 971 using alignment structures 969 interfaced with the alignment aids 935, according to an example implementation.

Figure 41:
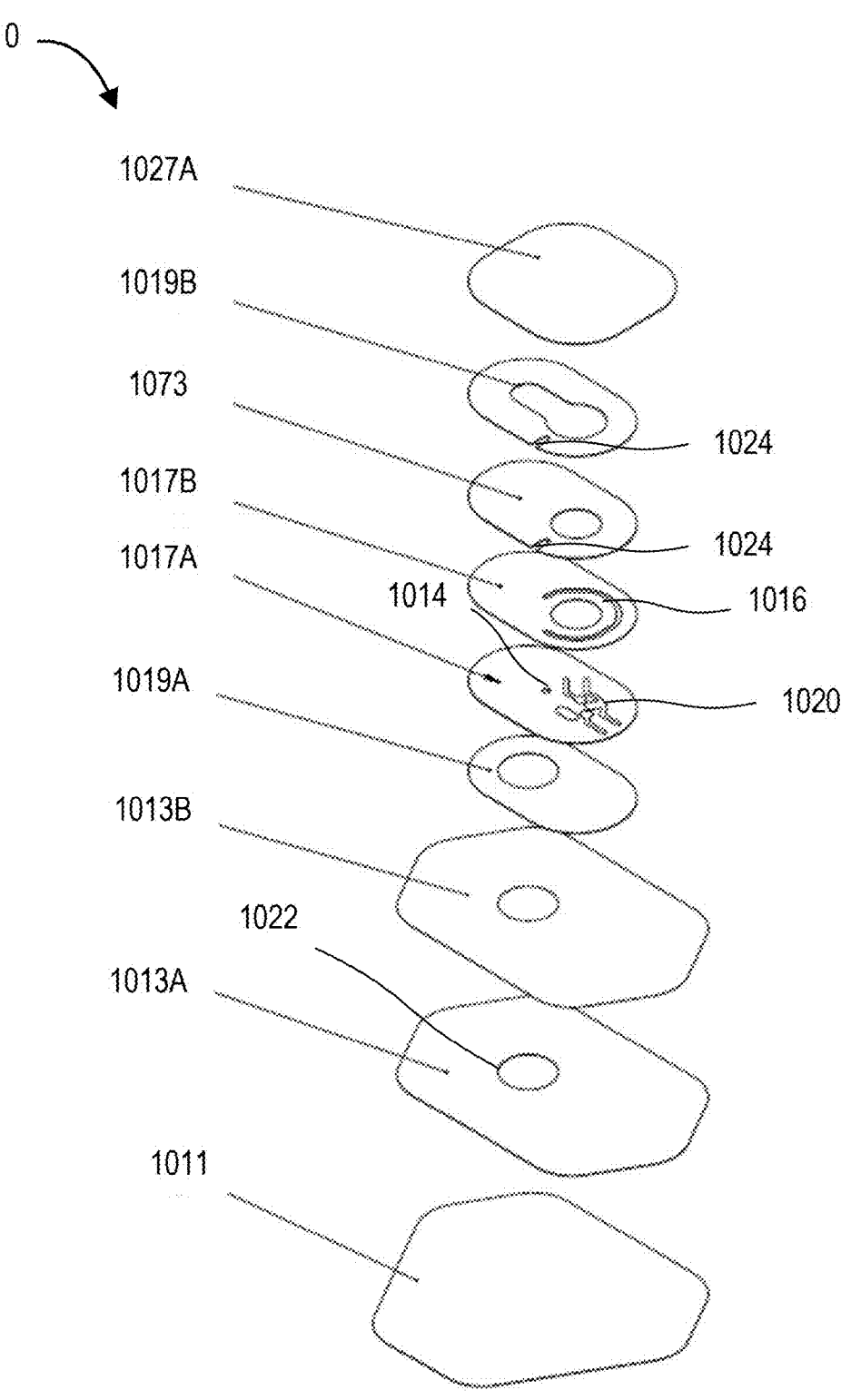
FIG. 41 is a schematic diagram of an exploded view of the sample handling device of FIGS. 40A-40D, according to an implementation.
Figure 42:
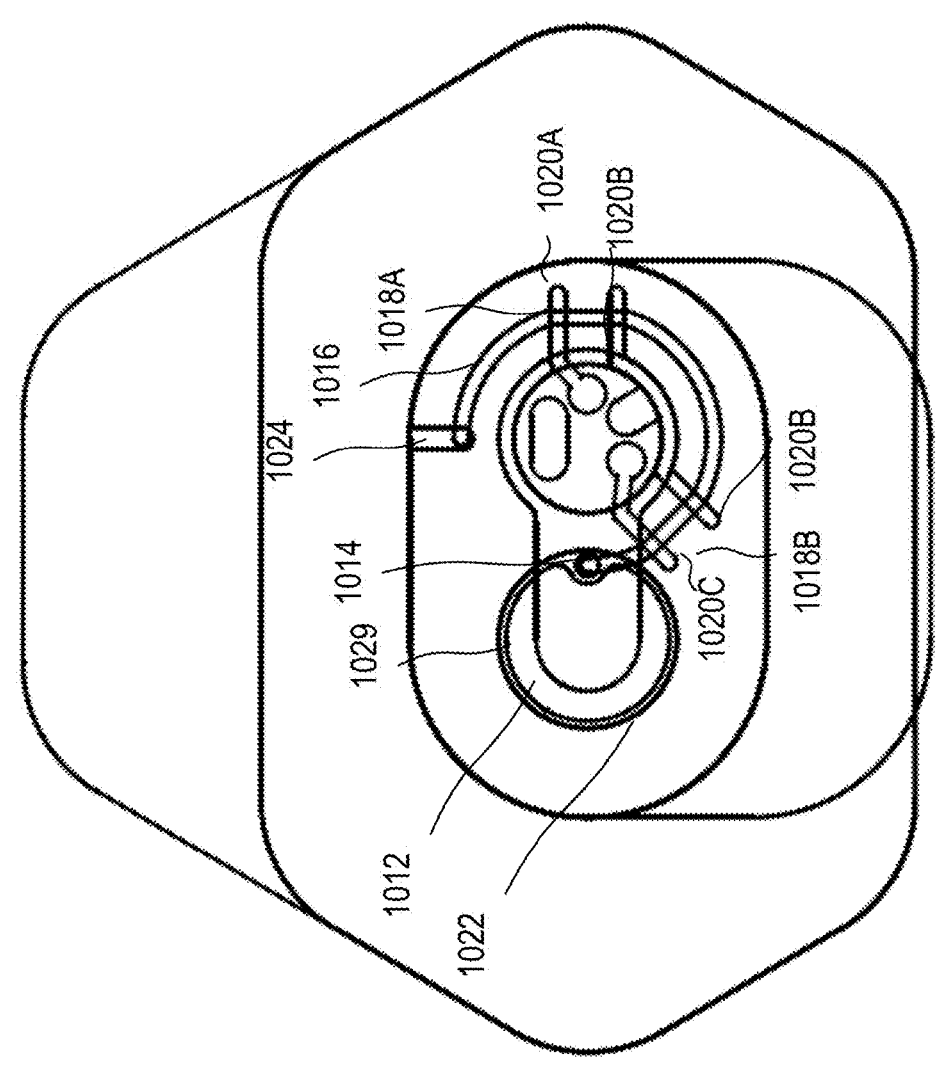
FIG. 42 is a schematic diagram of a top view of the sample handling device of FIG. 41, the layers being rendered transparent to show underlying features in the intermediate layers, according to an implementation.

FIGS. 40A-40D are schematic illustrations of a bottom view, top view, a side view and a perspective side view, respectively, of a sample handling device 1010, according to an embodiment. FIG. 41 is a schematic illustration of an exploded view of the sample handling device 1010, according to an example implementation. FIG. 42 is a schematic diagram of a top view of the sample handling device 1010, the layers being rendered transparent to show underlying features in the intermediate layers, according to an implementation.

The sample handling device 1010 can be substantially similar in structure and/or function to the sample handling devices, 110, 210, 310, 510, 710, 810, and/or 910 described herein. For example, the sample handling device 1010 can include a sample collection region 1012, an access port 1014, a flow channel 1016, a test regions 1018A and 1018B, and a set of electrodes 1020 that can be substantially similar in structure and/or function to that described with reference to the sample handling devices described above. In some embodiments, the sample handling device 1010 can include a temperature sensor (not shown). In some embodiments the temperature sensor can be included in the sample processing device to be coupled with the sample handling device 1010, and the temperature sensor can be configured such that a temperature of the sample fluid being tested at the one or more test regions 1018A, 1018B can be measured.

FIG. 41 is a schematic illustration of an exploded view of the sample handling device 1010, according to one implementation. In some implementations, the sample handling device 1010 can be constructed similar to the sample handling devices 210, 310,710, 810, and/or the sample handling device 910. For example, the sample handling device 1010 includes an interface layer 1011 which can be a release liner, and interface and adhesive layers 1013A and 1013B. The adhesive layer 1013A can be configured to be released and adhered to the skin of a user. The adhesive layers 1013A and 1013B include openings 1022 of the sample collection region 1012. The sample handling device 1010 includes an additional electrode layer adhesive 1019A to attach the electrode layer 1017A to the distal layers (e.g., the interface layer 1011, adhesive layers 1013A, 1013B, etc.). The sample handling device 1010 includes an access port layer defining the access port 1014 combined with the electrode layer 1017A as described with reference to the sample handling devices 210, 310, 710, 810, and/or 910. Accordingly, such similar portions and/or aspects are not described in further detail herein.

The interface layer 1011 and/or the adhesive layer 1013A, 1013B can be substantially similar to the interface layers and/or the adhesive layers described herein (e.g., interface layers 211, 711, 811, 911, etc. and adhesive layers 213, 713, 813, 913, etc.). In some embodiments, the access port 1014 can be formed at a suitably defined location on the electrode layer 1017A (also serving as the access port layer) and with respect to the opening 1022 of the sample collection region 1012 as shown in FIGS. 41 and 42. For example the access port 1014 can be positioned at an off center location with respect to the opening 1022 of the sample collection region 1012 to reduce, flush, and/or prevent formation of air bubbles in the collected sample of bodily fluid and/or to prime the flow of bodily fluid during use.

In some embodiments, an electrode layer 1017A defines the access port 1014, defined as a through opening. In some embodiments, the electrode layer 1017A can be substantially similar in structure and/or function to the electrode layers described herein (e.g., electrode layer 917A). Accordingly similar aspects of the electrode layer 1017A are not described in further detail.

The sample handling device 1010 can include a channel layer 1017B that is of a precise predefined thickness and determines a cross sectional size and volume of a portion of the flow channel 1016. In some embodiments, the sample handling device 1010 can include a vent layer 1073 configured to define a vent 1024. In some implementations, the vent layer 1073 can be adjoining a vent layer adhesive 1019B also defining the vent 1024 and with the adhesive surface that can be configured to attach to a portion of a sample processing device (e.g., sample processing device 130, 330, etc.). In some implementations, the sample handling device 1010 can be a disposable portion to be used with a durable portion with the adhesive surface of channel layer 1017B used to attached the sample handling device 1010 to the durable portion (e.g., attached to a plastic portion). In some implementations, the sample handling device 1010 can be used with and attached to a plastic portion or surface of a disposable sample processing device through the adhesive surface of channel layer 1017B.

In some embodiments, the adhesive surface of the channel layer 1017B can be configured to attach to a release liner layer 1027A. The release liner layer 1027A can be made of any suitable material to be released before attaching the sample handling device 1010 to a sample processing device (e.g., sample processing device 130, 330, etc.). In some embodiments, the flow channel 1016 can be defined by a curvilinear portion in the channel layer 1017B which extends to the vent 1024 defined by the vent layer 1073.

As described previously with reference to the device 910, the channel layer 1017B can include the test regions 1018A, and 1018B defined at specified portions along the flow path 1016. The electrode tracks and the sample ends of the electrodes 1020A, 1020B and 1020C can be defined on the proximal side of the electrode layer 1017A and the test regions 1018A, and 1018B. The flow path 1016 can be defined by the distal surface of the electrode layer 1017A and the channel layer 1017B such that as a sample of bodily fluid flows though the flow path 1016 and flows through each of the test regions an excitation signal applied by the excitation electrode 1020B (shared between the test regions 1018A and 1018B) can be delivered to the sample of fluid at the test region and can elicit a response from the sample of bodily fluid which can be sensed by the sensing electrode 1020A, 1020C located at that test region 1018A, 1018B, respectively. In some embodiments, a temperature sensor can be configured to be housed in the sample processing device and to measure the temperature of the sample of fluid being tested at one or more of the test regions 1018A and 1018B defined on the channel layer 1017B.

In some embodiments of the sample handling device, the electrodes 1020 can be configured such that multiple electrode pairs can share one or more electrodes. The multiple electrode pairs can be directed to multiple test regions such that the shared electrode can have a common terminal end and multiple sample ends that are located at or near the multiple test regions. For example, the electrodes 1020 can be configured such that two or more electrode pairs share an excitation electrode instead of one excitation electrode per pair of electrodes. The sample handling device 1010 can include two test regions 1018A, and 1018B, at predefined, as shown in FIG. 35A. The test region 1018A includes a set of electrodes 1020A, and 1020B and the test region 1018B includes the electrodes 1020B and 1020C respectively, with electrode 1020B serving both test regions. The test regions 1018A, and 1018B, are positioned at increasing distances from the access port 1014 and at a known distance between each other along the flow path 1016 before the sample of bodily fluid is ejected at 1024.

The sample handling device 1010 can include the top release liner layer 1027A configured to be released before attaching the device to a sample processing device as described herein.

In some embodiments, the electrode 1020B can be a common excitation electrode serving both test regions 1018A and 1018B, and the electrodes 1020A and 1020C can be configured to be sensing electrodes operating in combination with the electrode 1020B. Excitation signals can be applied via electrode 1020B and electrodes 1020A and 1020C can receive a response signal from the sample of fluid being tested at each test region. In some embodiments, the electrodes can be configured to operate as bipolar electrodes to excite and sense responses from a sample bodily fluid being tested. The electrodes 1020A, 1020B, and 1020C and the electrodes tracks can be printed using any suitable conductive and/or electrode ink as described previously. The terminal ends of the electrodes can be any suitable configuration to be electrically connected to a portion of a sample processing device. For example, the terminal ends can be configured to be connected via pogo pins, spring-loaded pins, flexible electrical connects, and/or the like.

In some implementations, the sample handling device 1010 can include a spacer portion 1029 incorporated to occupy space in the sample collection region 1012 as described previously with reference to spacer portion 729, 829, and/or 929. The spacer regions 1029 can be formed by printing thickening ink as described previously. The device 1010 can include additional adhesive layer (not shown), in some implementations, to aid with adhering to an alignment and/or mounting interface (e.g., a snap ring interface).

CONCLUSION

In summary, systems and methods are described herein for use in the instantaneous measurement and analysis of samples of bodily fluids to assess a property of the bodily fluid and/or a health parameter (e.g., degree of hydration, electrolyte losses, perspiration rate, etc.) of the user.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. Any portion of the apparatus and/or methods described herein may be combined in any combination, except mutually exclusive combinations. The embodiments described herein can include various combinations and/or sub-combinations of the functions, components, and/or features of the different embodiments described Where methods described above indicate certain events occurring in certain order, the ordering of certain events may be modified. Additionally, certain of the events may be performed concurrently in a parallel process when possible, as well as performed sequentially as described above.

The invention claimed is:

1. A wearable apparatus, comprising:
a processor;
a sample collection region having an inlet and configured to receive, via the inlet, an initial volume of bodily fluid of a user;
an access port in fluidic communication with the sample collection region;
a flow channel, in fluid communication with the access port and configured to direct a portion of the initial volume of bodily fluid towards a set of electrodes,
the set of electrodes including an excitation electrode and a sensing electrode, the excitation electrode configured to apply an excitation signal to the portion of the initial volume of bodily fluid, and the sensing electrode configured to receive a response signal from the portion of the initial volume of bodily fluid in response to the excitation signal, the sensing electrode configured to transmit the response signal to the processor to calculate an impedance associated with the portion of the initial volume of bodily fluid; and
a temperature sensor configured to measure a temperature associated with the portion of the initial volume of bodily fluid, the temperature sensor configured to transmit the measured temperature to the processor, the processor configured to estimate (a) a core body temperature of the user based on the measured temperature, and (b) a rate of loss of hydration of the user based on a correlation between the impedance and a salinity of the bodily fluid.

2. The wearable apparatus of claim 1, wherein the flow channel is further configured to direct the portion of initial volume of bodily fluid to an outlet.

3. The wearable apparatus of claim 1, wherein the set of electrodes includes two pairs of electrodes, each pair of the two pairs of electrodes including at least one excitation electrode and at least one sensing electrode, the two pairs of electrodes being positioned at a predefined distance from each other.

4. The wearable apparatus of claim 3, wherein the flow channel is further configured to direct the portion of initial volume of bodily fluid to each pair of the two pairs of electrodes such that the portion of initial volume of bodily fluid passes through the two pairs of electrodes in a sequential manner.

5. The wearable apparatus of claim 1, wherein at least a portion of the flow channel is defined to include at least one of a linear, curvilinear, looped, planar, non-planar, serpentine, or tortuous shape.

6. The wearable apparatus of claim 1, wherein at least one of the flow channel or the set of electrodes includes a hydrophilic coating configured to encourage the flow of the bodily fluid.

7. The wearable apparatus of claim 1, wherein the flow channel has a cross-sectional area of between about 0.2 mm and about 5.0 mm.

8. The wearable apparatus of claim 1, wherein at least a portion of the set of electrodes includes about 80% silver, by weight, and about 20% silver chloride by weight.

9. The wearable apparatus of claim 1, wherein the set of electrodes includes bipolar electrodes configured to supply a current to the portion of the initial volume of bodily fluid and to sense a voltage associated with the portion of the initial volume of bodily fluid.

10. The wearable apparatus of claim 1, wherein the sample collection region is configured such that the portion of the initial volume of bodily fluid is urged from the sample collection region to the flow channel via the access port in a continuous manner upon the initial volume of bodily fluid collected exceeding a threshold volume.

11. The wearable apparatus of claim 10, the threshold volume is a first threshold volume, further comprising a spacer portion defined in the sample collection region and configured to reduce a fluid capacity of the sample collection region such that the portion of the initial volume of bodily fluid is urged from the sample collection region via the access port and via the flow channel upon the initial volume of bodily fluid collected exceeding a second threshold volume smaller than the first threshold volume.

12. The wearable apparatus of claim 1, wherein the set of electrodes are configured to sense a signal indicating a presence of a quantity of at least one of $Na^+$, $Cl^-$, $Ca^{2+}$, $K^+$, or $Mg^{2+}$ ions in the portion of the initial volume of bodily fluid.

13. The wearable apparatus of claim 1, wherein at least one electrode of the set of electrodes includes a carbon coating configured to reduce corrosive of the set of electrodes.

14. The wearable apparatus of claim 1, wherein the set of electrodes are configured to sense a signal indicating a presence of a quantity of at least one of lactase, glucose, lactates, or pyruvates in the portion of the initial volume of bodily fluid.

15. A system, comprising:
a memory storing a set of instructions;
a processor coupled to the memory, and configured to execute the instructions stored in the memory; and
a wearable device including
a sample collection region configured to receive an initial volume of bodily fluid of a user;
an access port in fluidic communication with the sample collection region;

a flow channel, in fluid communication with the access port and configured to direct a portion of the initial volume of bodily fluid towards a set of electrodes;
the set of electrodes, including an excitation electrode and a sensing electrode, the excitation electrode configured to apply an excitation signal to the portion of the initial volume of bodily fluid, and the sensing electrode configured to receive a response signal from the portion of the initial volume of bodily fluid and in response to the excitation signal; and
a temperature sensor configured to measure a temperature associated with the portion of the initial volume of bodily fluid;
wherein the instructions, when executed, are configured to cause the processor to:
send the excitation signal to the excitation electrode;
receive the response signal from the sensing electrode;
calculate, based on the response signal, an impedance associated with the portion of the initial volume of bodily fluid;
receive, from the temperature sensor, a signal associated with the measured temperature, and
calculate, (a) a core body temperature of the user based on the measured temperature, and (b) a rate of loss of hydration of the user based on a correlation between the impedance and a salinity of the bodily fluid.

16. The system of claim 15, the portion of the initial volume of bodily fluid being a first portion, wherein the flow channel is further configured to direct the first portion to an outlet and sequentially urge a second portion of the initial volume of bodily fluid to flow towards the set of electrodes.

17. The system of claim 15, wherein the instructions, when executed, are further configured to cause the processor to:
determine an osmolality of the initial volume of bodily fluid, and a state of hydration associated with a source of the bodily fluid; and
indicate, via the wearable device, a signal representing a state of hydration of the user.

18. The system of claim 17, wherein the instructions, when executed, are further configured to cause the processor to:
identify the state of hydration to be lesser than a predefined value, and
produce, based on the identification and via the wearable device, an alert advising replenishment of the source of bodily fluid.

19. The system of claim 17, further comprising:
an accelerometer wherein the instructions, when executed, are further configured to cause the processor to:
identify a state of acceleration of the system, and
estimate, based on the state of acceleration, a predicted optimal rate of replenishment of the source of bodily fluid.

* * * * *